United States Patent [19]
Klaus et al.

[11] Patent Number: 6,030,946
[45] Date of Patent: *Feb. 29, 2000

[54] REVERSIBLE CYSTEINE PROTEASE INHIBITORS

[75] Inventors: Jeffrey L. Klaus, Redwood City; David Rasnick, San Francisco; James T. Palmer, San Ramon; Elaine Yee-Lin Kuo, San Francisco, all of Calif.

[73] Assignee: Axys Pharmaceuticals, Inc., South San Francisco, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/657,103

[22] Filed: Jun. 3, 1996

Related U.S. Application Data

[63] Continuation-in-part of application No. 08/474,993, Jun. 7, 1995, abandoned.

[51] Int. Cl.⁷ .............................. A61K 38/00; C07K 2/00
[52] U.S. Cl. .................................. 514/12; 514/16; 514/17; 514/18; 514/19; 514/37; 530/328; 530/329; 530/330; 530/331; 435/4; 435/23; 435/24; 435/94.63; 435/94.65; 435/212; 544/121; 564/511
[58] Field of Search .................................. 514/12, 16–19, 514/37; 530/328–331; 435/4, 23, 24, 94.63, 99.65, 212; 544/121; 564/511

[56] References Cited

U.S. PATENT DOCUMENTS

| | | | |
|---|---|---|---|
| 3,859,337 | 1/1975 | Herz et al. | 260/500.5 |
| 4,381,305 | 4/1983 | Casagrande et al. | 424/263 |
| 5,607,937 | 3/1997 | Stuerzebecher et al. | 514/255 |

FOREIGN PATENT DOCUMENTS

| | | |
|---|---|---|
| 63-275575 | 11/1988 | Japan . |
| 92/08709 | 5/1992 | WIPO . |
| 92/16549 | 10/1992 | WIPO . |
| 94/18185 | 8/1994 | WIPO . |

OTHER PUBLICATIONS

Hara, K., et al. "Inhibition of Calcium–Activated Neutral Protease of Monkey Cardiac Muscle by Epoxysuccinic Acid Derivatives," *Biomedical Research*, 4(1):121–124 (1983).

Westmark et al., "Photoregulation of Enzyme Activity. Photochromic, Transition–State–Analogue Inhibitors of Cysteine and Serine Proteases," *J. Am. Chem. Soc.*, 115:3416–3419 (1993).

Turk et al., "The Cystatins: Protein Inhibitors of Cysteine Proteinases," *FEBS*, 285(2):213–219 (1991).

Giordano et al., "Synthesis and Properties of D–glucosamine N–peptidyl Derivatives as Substrate Analog Inhibitors of Papain and Cathepsin B," *Eur. J. Med. Chem.* 26:753:762 (1991).

*Primary Examiner*—Bennett Celsa
*Attorney, Agent, or Firm*—Flehr Hohbach Test Albritton & Herbert LLP; David J. Brezner; Robin M. Silva

[57] ABSTRACT

Cysteine protease inhibitors are provided.

21 Claims, 11 Drawing Sheets

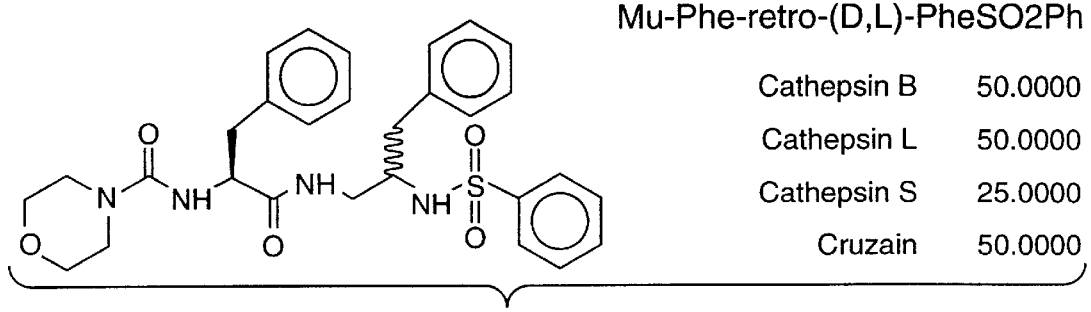
Mu-Phe-retro-(D,L)-PheSO2Ph
| Cathepsin B | 50.0000 |
| Cathepsin L | 50.0000 |
| Cathepsin S | 25.0000 |
| Cruzain | 50.0000 |
FIG._1A
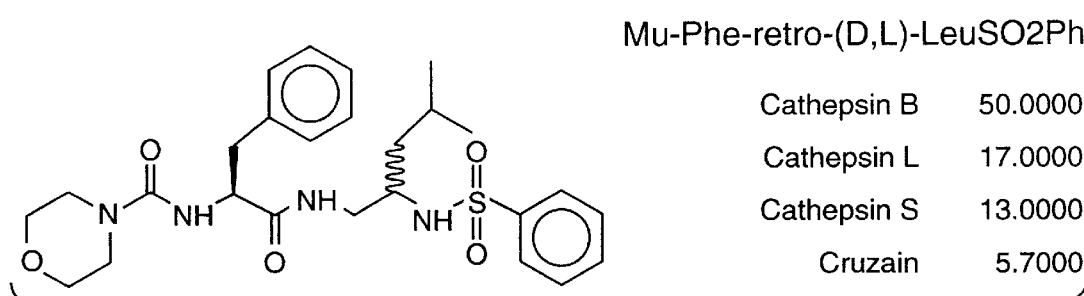
Mu-Phe-retro-(D,L)-LeuSO2Ph
| Cathepsin B | 50.0000 |
| Cathepsin L | 17.0000 |
| Cathepsin S | 13.0000 |
| Cruzain | 5.7000 |
FIG._1B
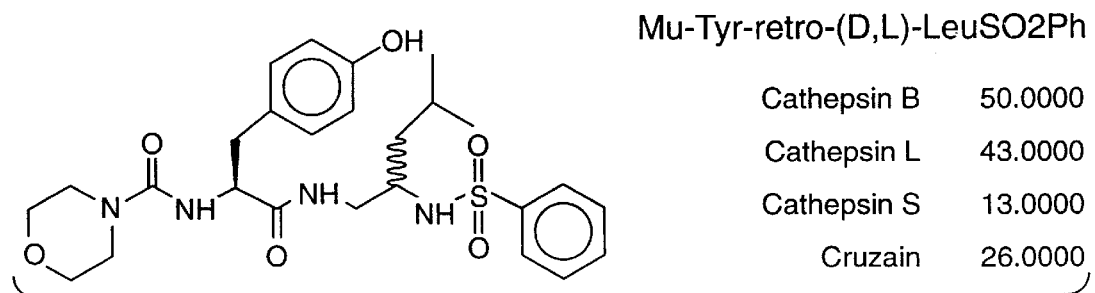
Mu-Tyr-retro-(D,L)-LeuSO2Ph
| Cathepsin B | 50.0000 |
| Cathepsin L | 43.0000 |
| Cathepsin S | 13.0000 |
| Cruzain | 26.0000 |
FIG._1C
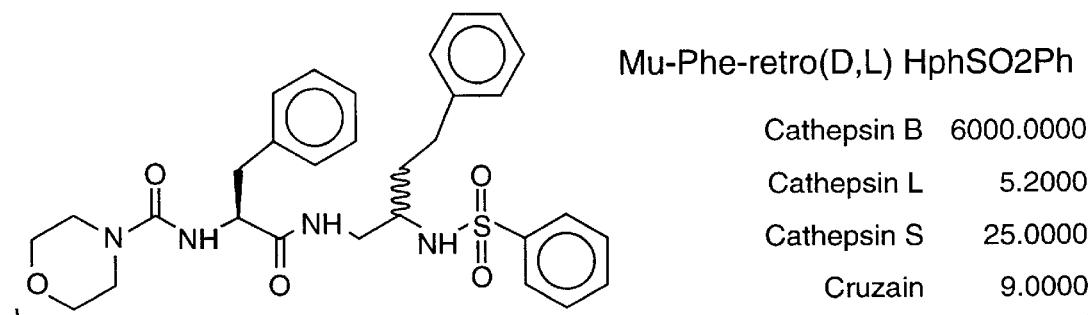
Mu-Phe-retro(D,L) HphSO2Ph
| Cathepsin B | 6000.0000 |
| Cathepsin L | 5.2000 |
| Cathepsin S | 25.0000 |
| Cruzain | 9.0000 |
FIG._1D

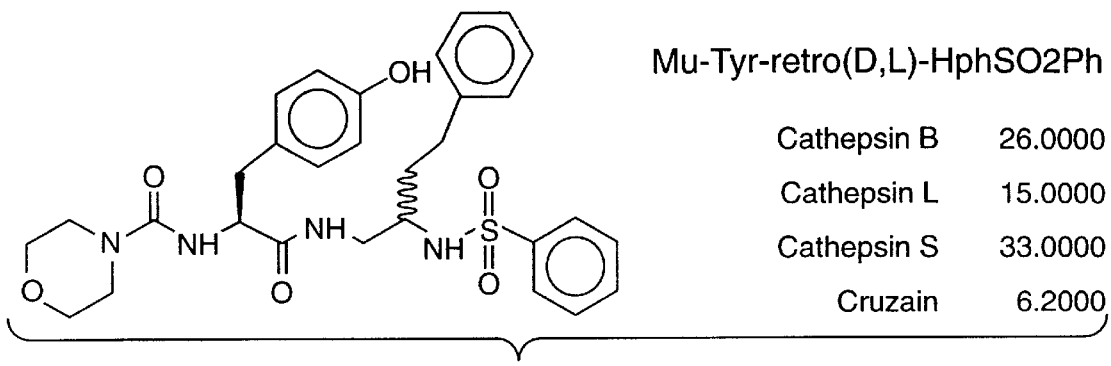
Mu-Tyr-retro(D,L)-HphSO2Ph
| | |
|---|---|
| Cathepsin B | 26.0000 |
| Cathepsin L | 15.0000 |
| Cathepsin S | 33.0000 |
| Cruzain | 6.2000 |
FIG._1E
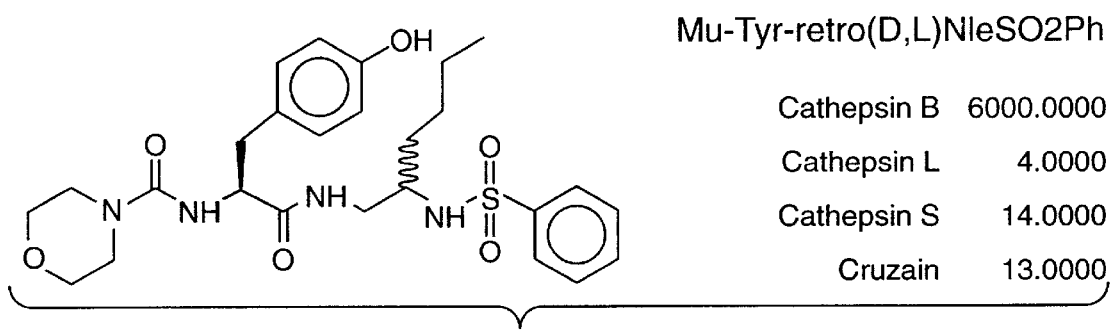
Mu-Tyr-retro(D,L)NleSO2Ph
| | |
|---|---|
| Cathepsin B | 6000.0000 |
| Cathepsin L | 4.0000 |
| Cathepsin S | 14.0000 |
| Cruzain | 13.0000 |
FIG._1F
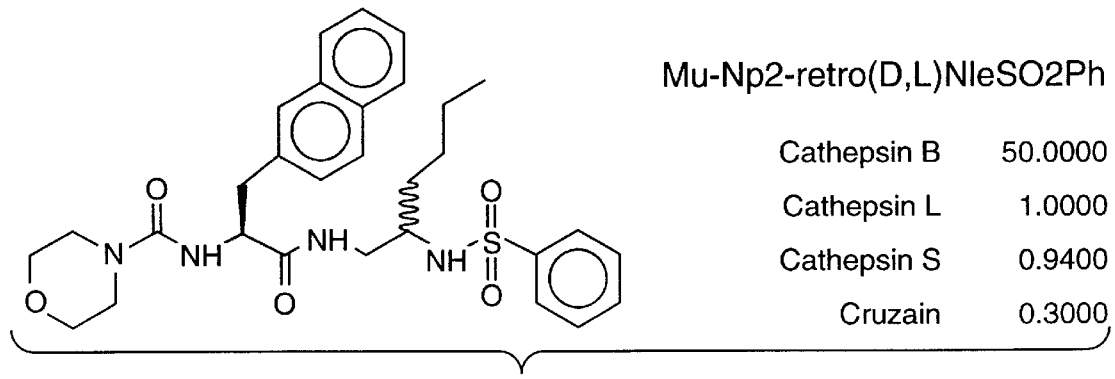
Mu-Np2-retro(D,L)NleSO2Ph
| | |
|---|---|
| Cathepsin B | 50.0000 |
| Cathepsin L | 1.0000 |
| Cathepsin S | 0.9400 |
| Cruzain | 0.3000 |
FIG._1G
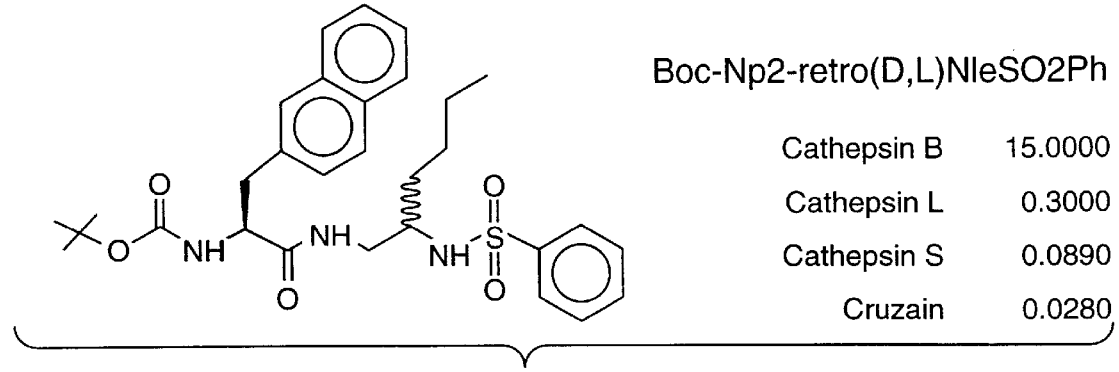
Boc-Np2-retro(D,L)NleSO2Ph
| | |
|---|---|
| Cathepsin B | 15.0000 |
| Cathepsin L | 0.3000 |
| Cathepsin S | 0.0890 |
| Cruzain | 0.0280 |
FIG._1H

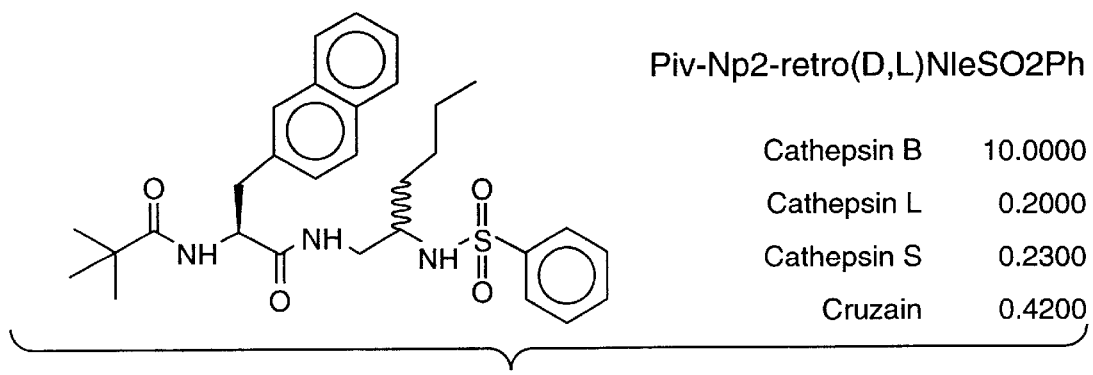
Piv-Np2-retro(D,L)NleSO2Ph
| Cathepsin B | 10.0000 |
|---|---|
| Cathepsin L | 0.2000 |
| Cathepsin S | 0.2300 |
| Cruzain | 0.4200 |
*FIG._1I*
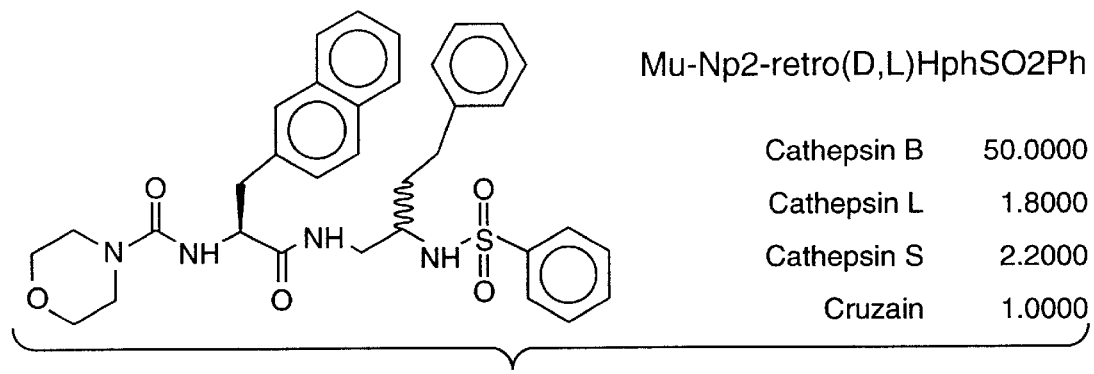
Mu-Np2-retro(D,L)HphSO2Ph
| Cathepsin B | 50.0000 |
|---|---|
| Cathepsin L | 1.8000 |
| Cathepsin S | 2.2000 |
| Cruzain | 1.0000 |
*FIG._1J*
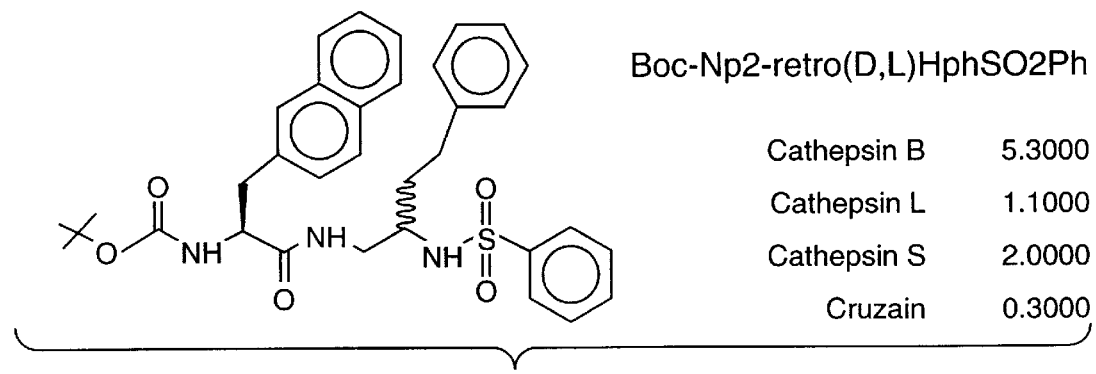
Boc-Np2-retro(D,L)HphSO2Ph
| Cathepsin B | 5.3000 |
|---|---|
| Cathepsin L | 1.1000 |
| Cathepsin S | 2.0000 |
| Cruzain | 0.3000 |
*FIG._1K*
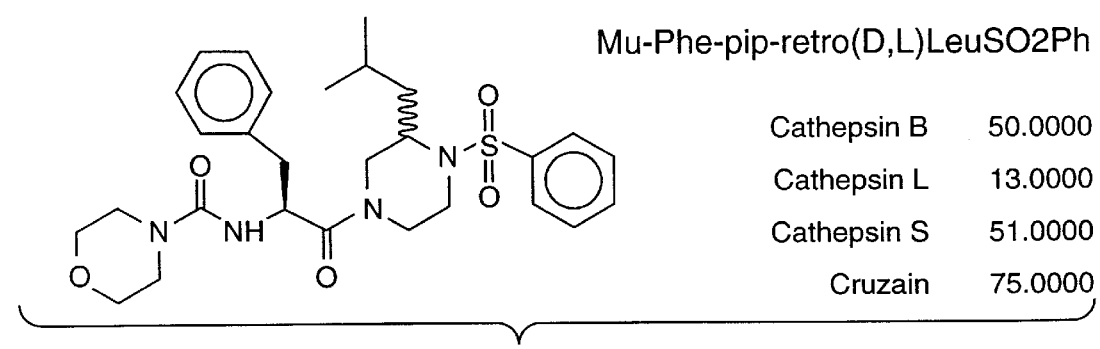
Mu-Phe-pip-retro(D,L)LeuSO2Ph
| Cathepsin B | 50.0000 |
|---|---|
| Cathepsin L | 13.0000 |
| Cathepsin S | 51.0000 |
| Cruzain | 75.0000 |
*FIG._1L*

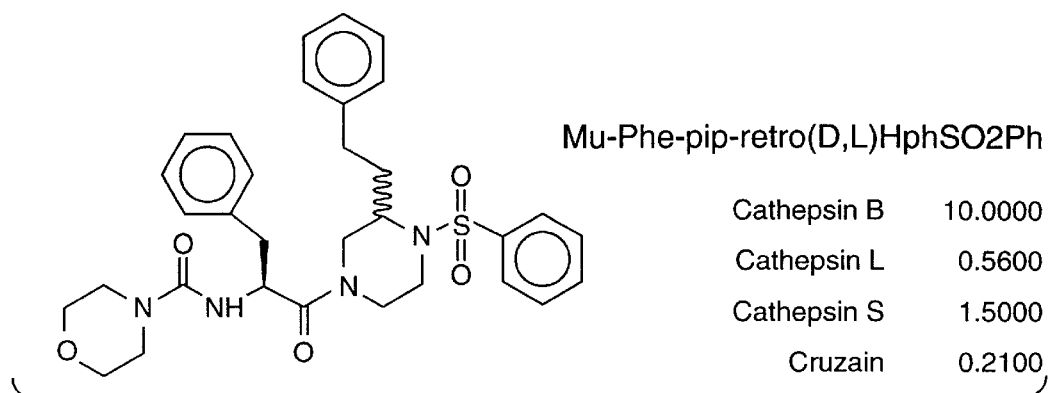
Mu-Phe-pip-retro(D,L)HphSO2Ph
| | |
|---|---|
| Cathepsin B | 10.0000 |
| Cathepsin L | 0.5600 |
| Cathepsin S | 1.5000 |
| Cruzain | 0.2100 |
*FIG._1M*
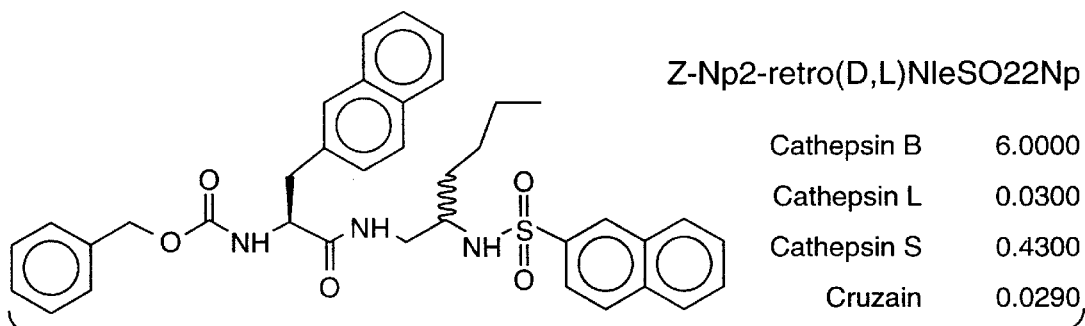
Z-Np2-retro(D,L)NleSO22Np
| | |
|---|---|
| Cathepsin B | 6.0000 |
| Cathepsin L | 0.0300 |
| Cathepsin S | 0.4300 |
| Cruzain | 0.0290 |
*FIG._1N*
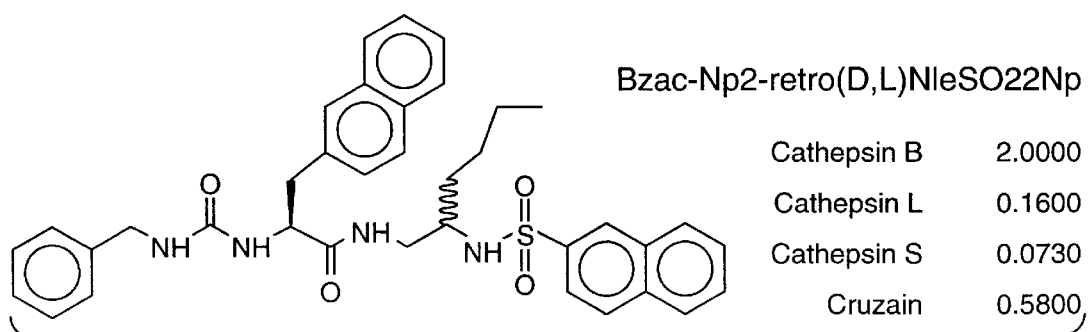
Bzac-Np2-retro(D,L)NleSO22Np
| | |
|---|---|
| Cathepsin B | 2.0000 |
| Cathepsin L | 0.1600 |
| Cathepsin S | 0.0730 |
| Cruzain | 0.5800 |
*FIG._1O*
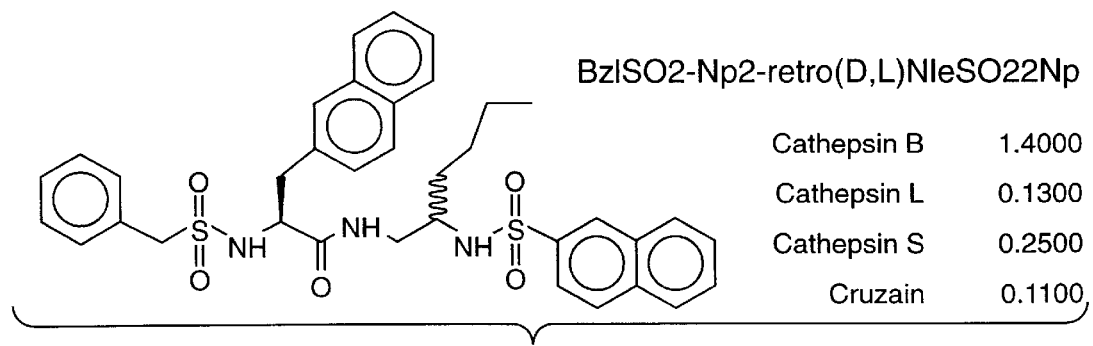
BzlSO2-Np2-retro(D,L)NleSO22Np
| | |
|---|---|
| Cathepsin B | 1.4000 |
| Cathepsin L | 0.1300 |
| Cathepsin S | 0.2500 |
| Cruzain | 0.1100 |
*FIG._1P*

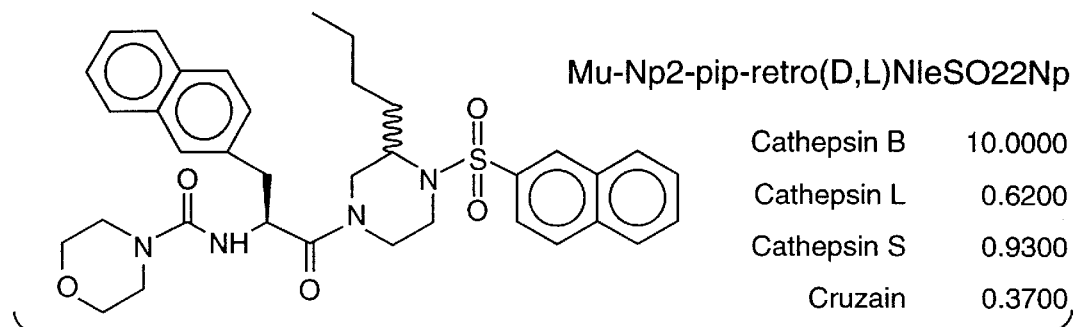
FIG._1Q
Mu-Np2-pip-retro(D,L)NleSO22Np
| | |
|---|---|
| Cathepsin B | 10.0000 |
| Cathepsin L | 0.6200 |
| Cathepsin S | 0.9300 |
| Cruzain | 0.3700 |
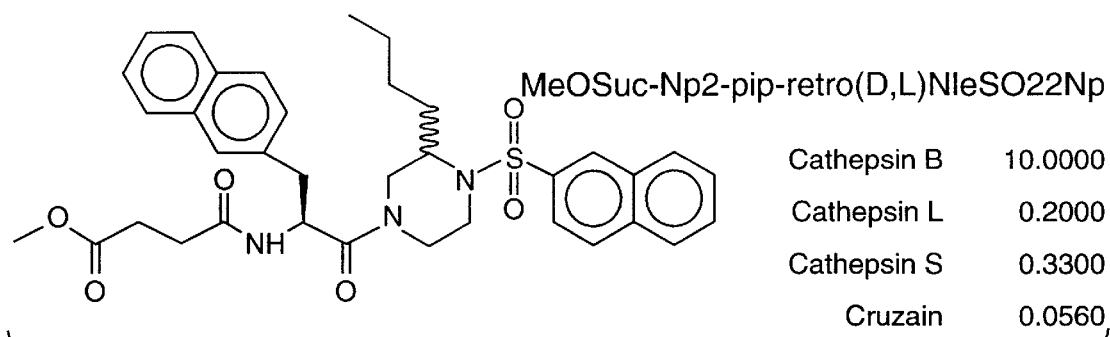
FIG._1R
MeOSuc-Np2-pip-retro(D,L)NleSO22Np
| | |
|---|---|
| Cathepsin B | 10.0000 |
| Cathepsin L | 0.2000 |
| Cathepsin S | 0.3300 |
| Cruzain | 0.0560 |
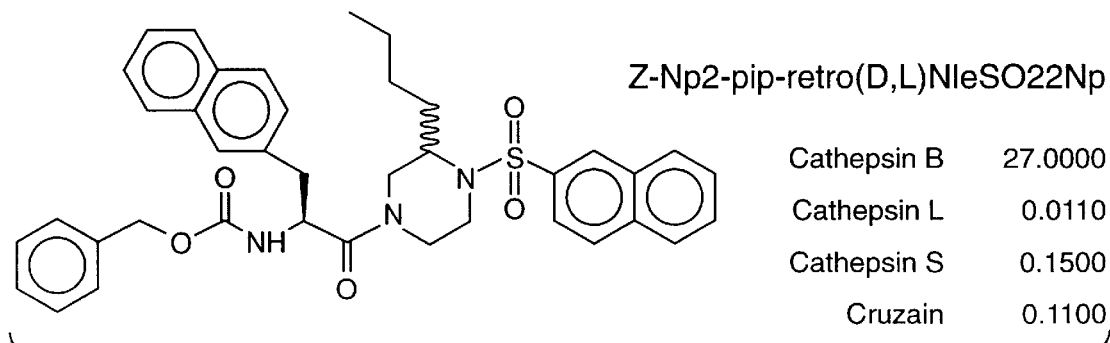
FIG._1S
Z-Np2-pip-retro(D,L)NleSO22Np
| | |
|---|---|
| Cathepsin B | 27.0000 |
| Cathepsin L | 0.0110 |
| Cathepsin S | 0.1500 |
| Cruzain | 0.1100 |
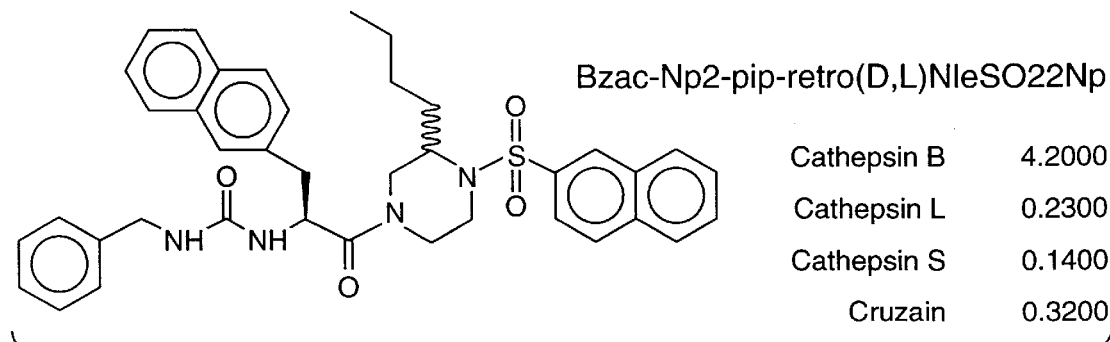
FIG._1T
Bzac-Np2-pip-retro(D,L)NleSO22Np
| | |
|---|---|
| Cathepsin B | 4.2000 |
| Cathepsin L | 0.2300 |
| Cathepsin S | 0.1400 |
| Cruzain | 0.3200 |

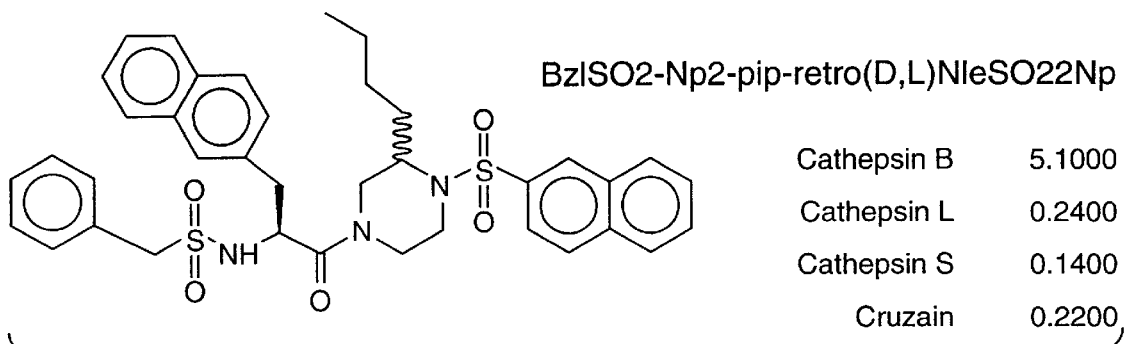
BzlSO2-Np2-pip-retro(D,L)NleSO22Np
| | |
|---|---:|
| Cathepsin B | 5.1000 |
| Cathepsin L | 0.2400 |
| Cathepsin S | 0.1400 |
| Cruzain | 0.2200 |
*FIG._1U*
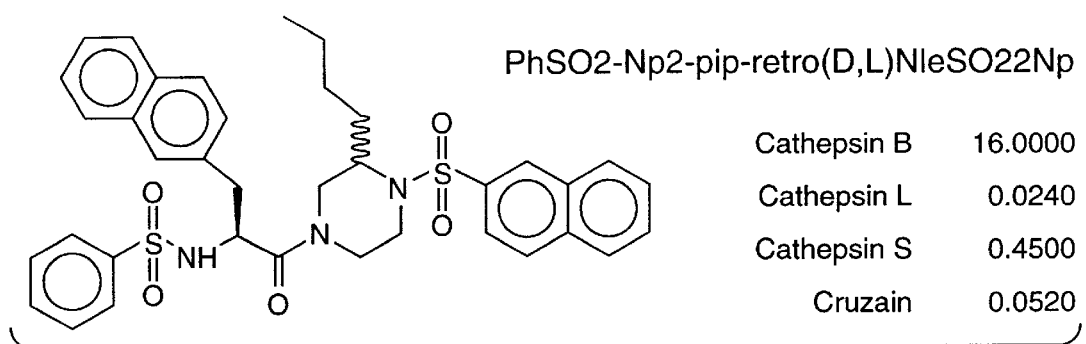
PhSO2-Np2-pip-retro(D,L)NleSO22Np
| | |
|---|---:|
| Cathepsin B | 16.0000 |
| Cathepsin L | 0.0240 |
| Cathepsin S | 0.4500 |
| Cruzain | 0.0520 |
*FIG._1V*
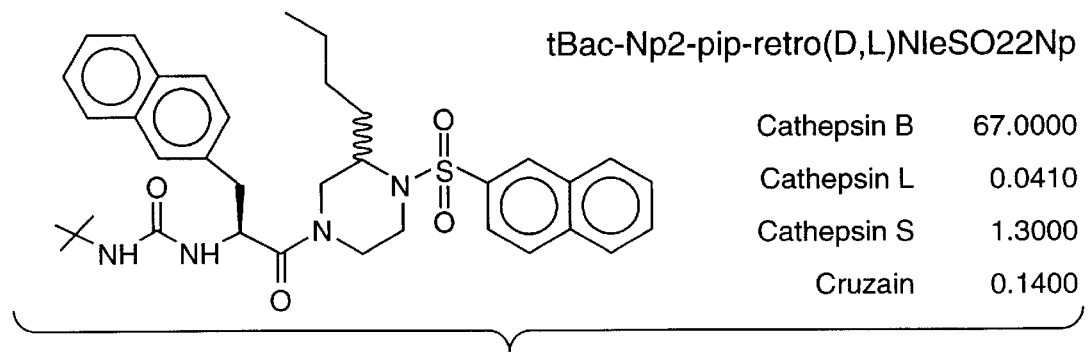
tBac-Np2-pip-retro(D,L)NleSO22Np
| | |
|---|---:|
| Cathepsin B | 67.0000 |
| Cathepsin L | 0.0410 |
| Cathepsin S | 1.3000 |
| Cruzain | 0.1400 |
*FIG._1W*
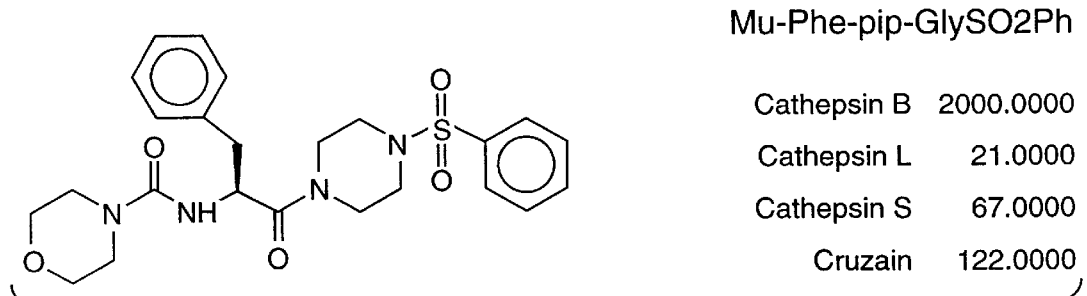
Mu-Phe-pip-GlySO2Ph
| | |
|---|---:|
| Cathepsin B | 2000.0000 |
| Cathepsin L | 21.0000 |
| Cathepsin S | 67.0000 |
| Cruzain | 122.0000 |
*FIG._1X*

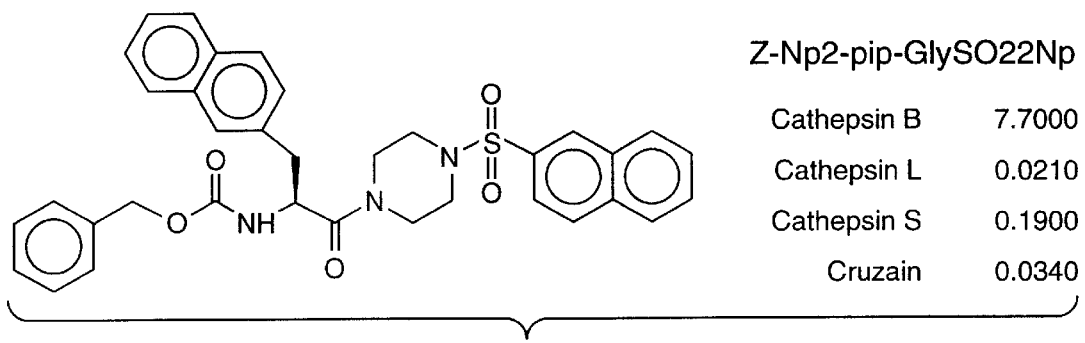
FIG._1Y
Z-Np2-pip-GlySO22Np
| | |
|---|---|
| Cathepsin B | 7.7000 |
| Cathepsin L | 0.0210 |
| Cathepsin S | 0.1900 |
| Cruzain | 0.0340 |
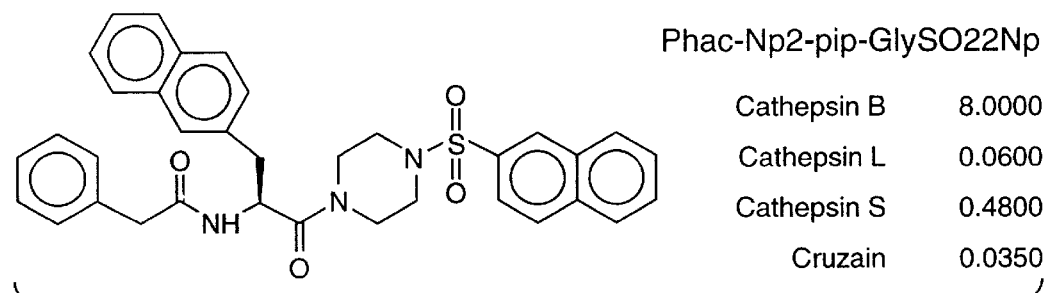
FIG._1Z
Phac-Np2-pip-GlySO22Np
| | |
|---|---|
| Cathepsin B | 8.0000 |
| Cathepsin L | 0.0600 |
| Cathepsin S | 0.4800 |
| Cruzain | 0.0350 |
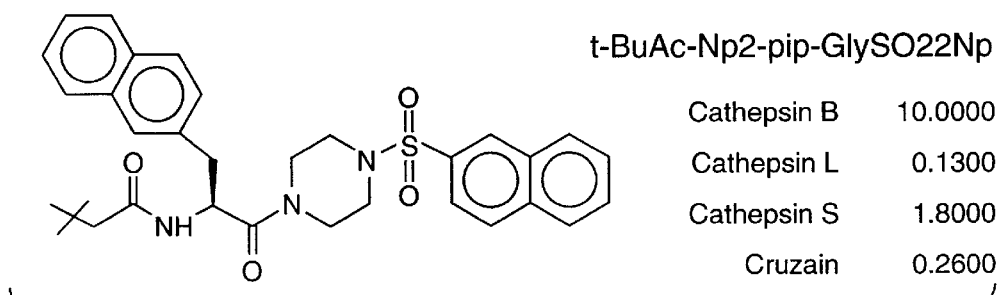
FIG._1AA
t-BuAc-Np2-pip-GlySO22Np
| | |
|---|---|
| Cathepsin B | 10.0000 |
| Cathepsin L | 0.1300 |
| Cathepsin S | 1.8000 |
| Cruzain | 0.2600 |
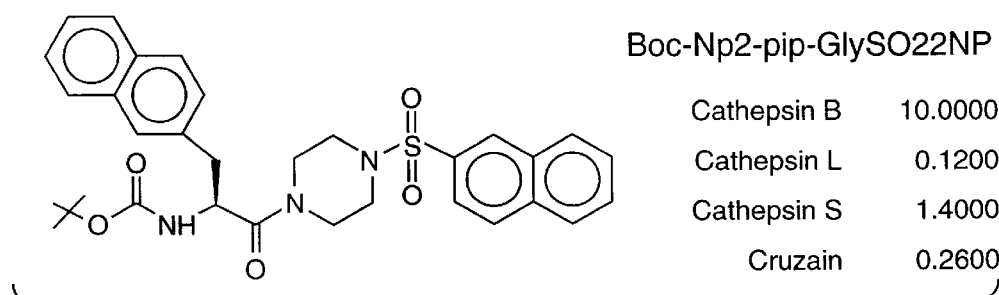
FIG._1BB
Boc-Np2-pip-GlySO22NP
| | |
|---|---|
| Cathepsin B | 10.0000 |
| Cathepsin L | 0.1200 |
| Cathepsin S | 1.4000 |
| Cruzain | 0.2600 |

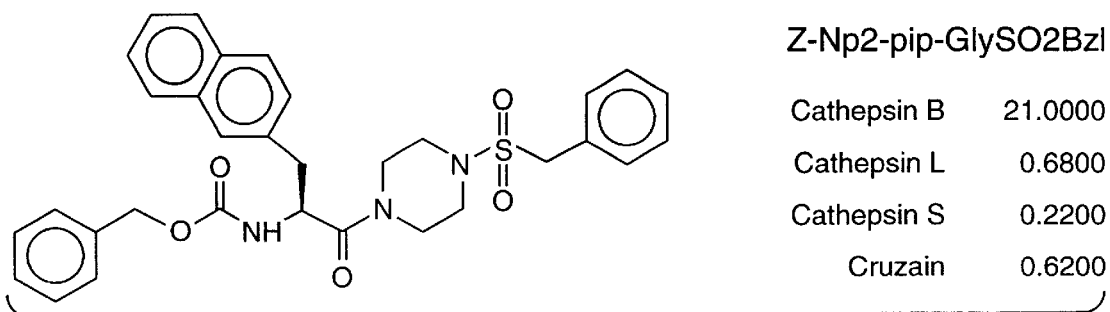
Z-Np2-pip-GlySO2Bzl
| | |
|---|---|
| Cathepsin B | 21.0000 |
| Cathepsin L | 0.6800 |
| Cathepsin S | 0.2200 |
| Cruzain | 0.6200 |
FIG._1CC
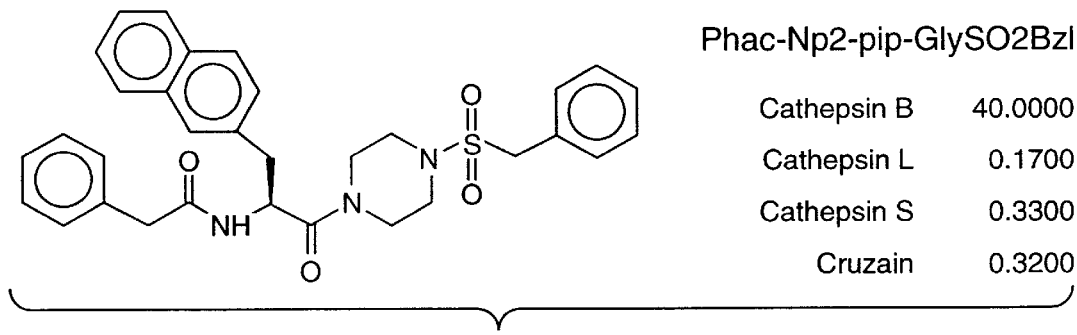
Phac-Np2-pip-GlySO2Bzl
| | |
|---|---|
| Cathepsin B | 40.0000 |
| Cathepsin L | 0.1700 |
| Cathepsin S | 0.3300 |
| Cruzain | 0.3200 |
FIG._1DD

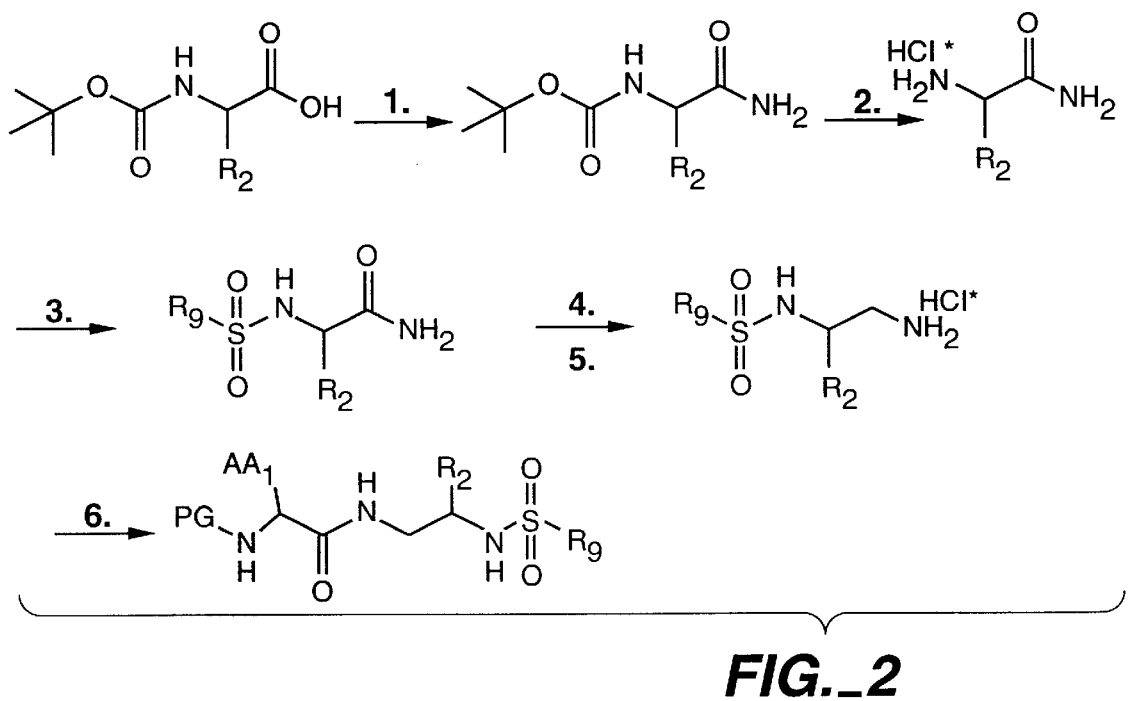
FIG._2
FIG._3
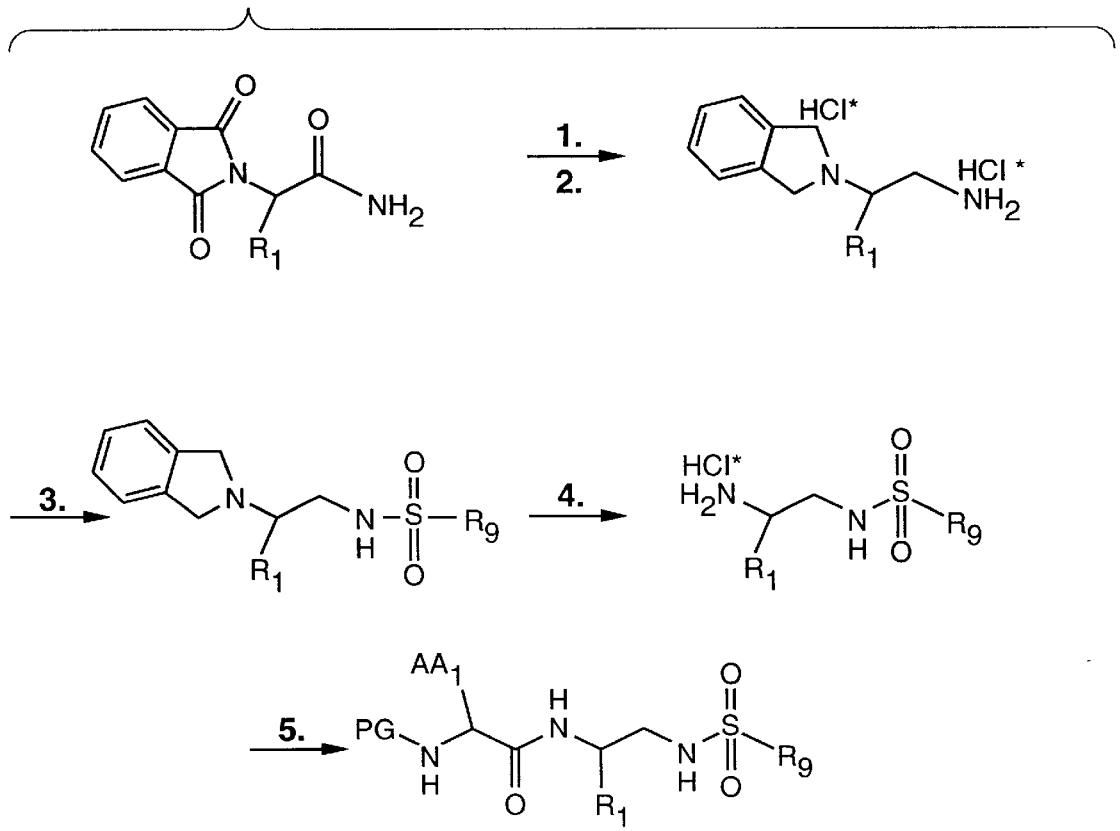

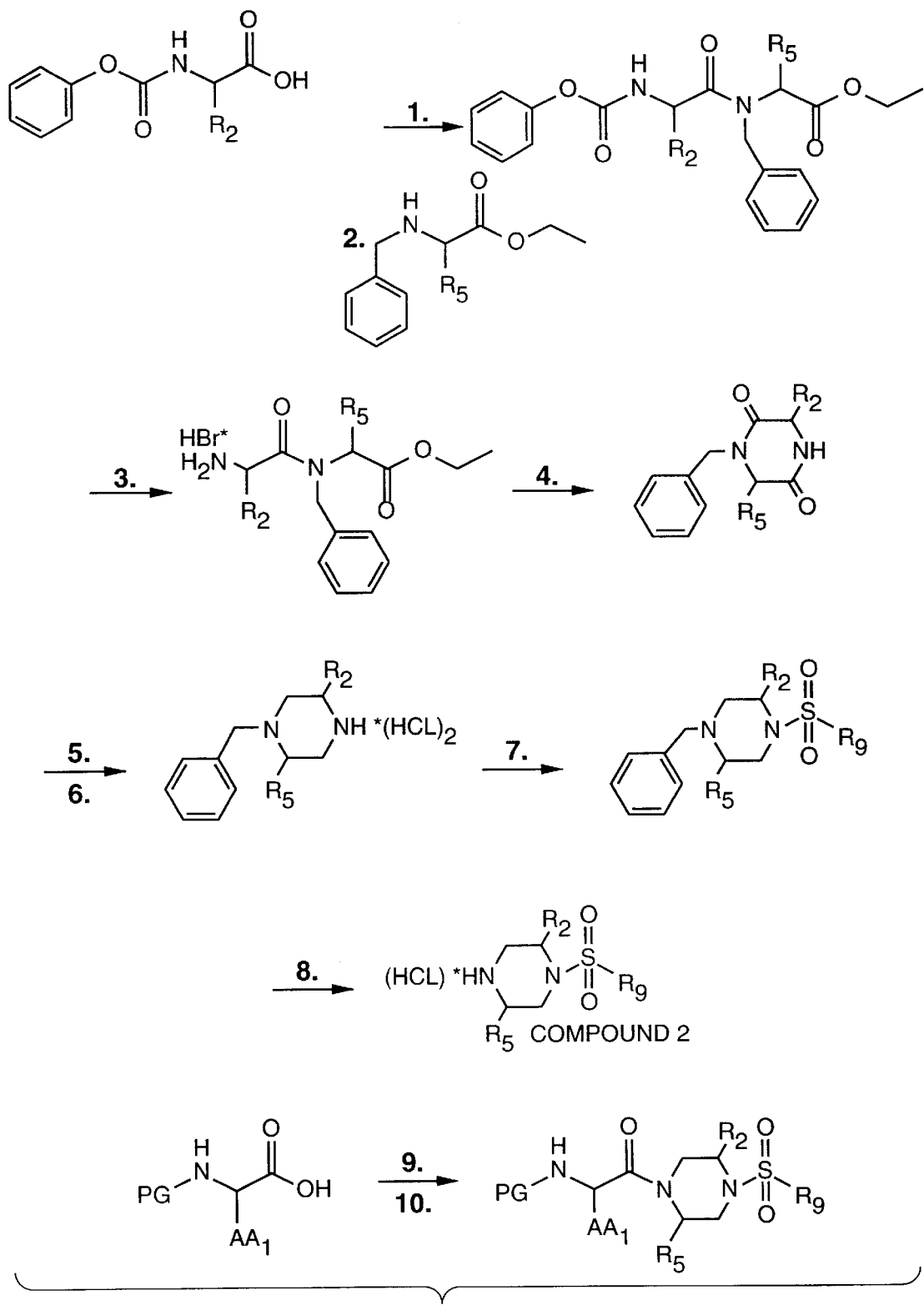
FIG._4

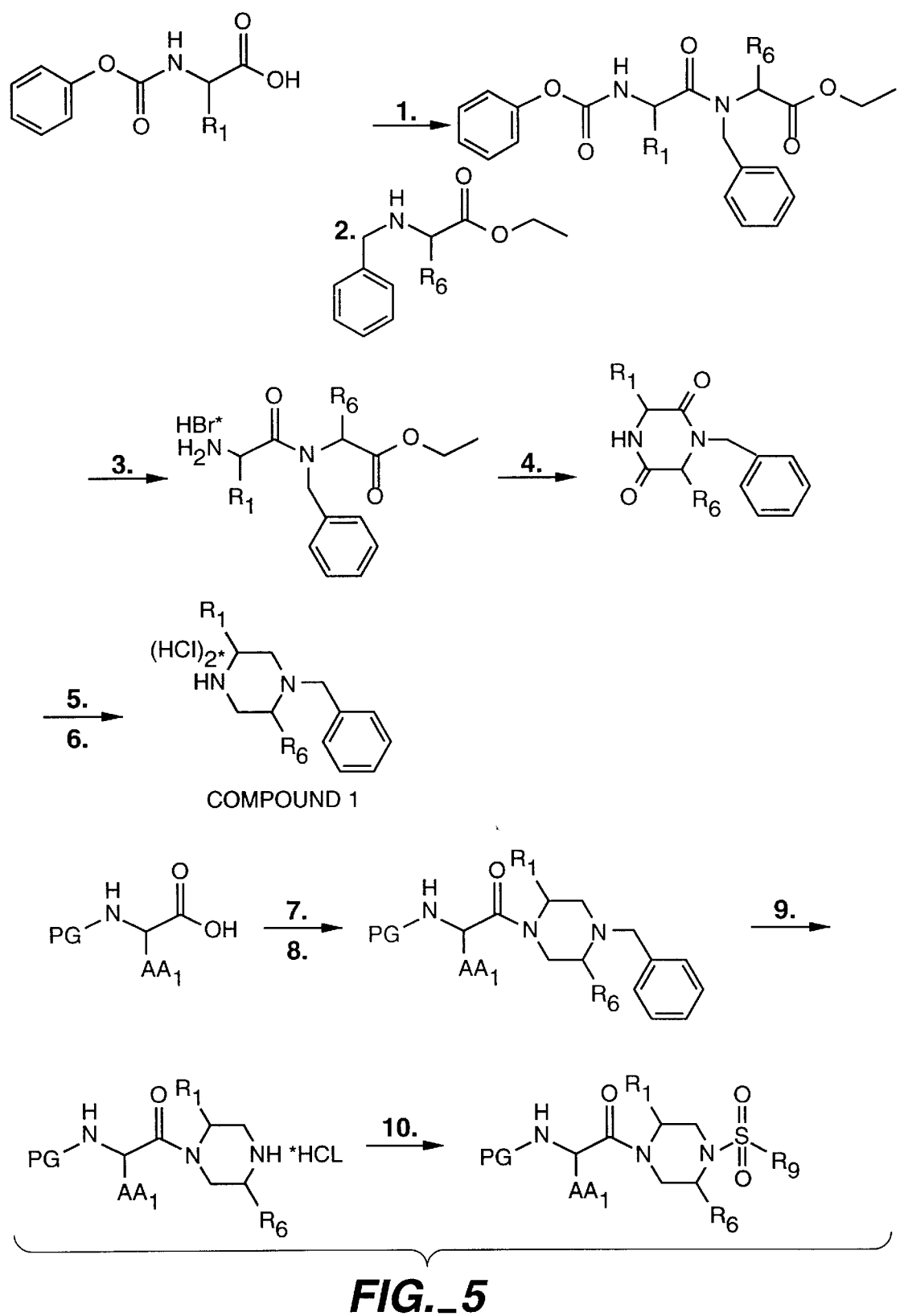
FIG._5

REVERSIBLE CYSTEINE PROTEASE INHIBITORS

This is a continuation-in-part of application Ser. No. 08/474,993, filed Jun. 7, 1995, abandoned.

FIELD OF THE INVENTION

The invention relates to novel reversible protease inhibitors. The inhibitors are selective for cysteine proteases.

BACKGROUND OF THE INVENTION

Cysteine or thiol proteases contain a cysteine residue at the active site responsible for proteolysis. Since cysteine proteases have been implicated in a number of diseases, including arthritis, muscular dystrophy, inflammation, tumor invasion, glomerulonephritis, malaria, and other parasite-borne infections, methods for selectively and irreversibly inactivating them provide opportunities for new drug candidates. See, for example, Esser, R. E. et al., Arthritis & Rheumatism (1994) 37, 236; Meijers, M. H. M. et al., Agents Actions (1993), 39 (Special Conference Issue), C219; Machleidt, W. et al, Fibrinolysis (1992), 6 Suppl. 4,125; Sloane, B. F. et al., Biomed. Biochim. Acta (1991), 50, 549; Duffy, M. J., Clin. Exp. Metastasis (1992), 10, 145; Rosenthal, P. J., Wollish, W. S., Palmer, J. T., Rasnick, D., J. Clin. Investigations (1991), 88, 1467; Baricos, W. H. et al, Arch. Biochem. Biophys. (1991), 288, 468; Thornberry, N. A. et al., Nature (1992), 356, 768.

Low molecular weight inhibitors of cysteine proteases have been described by Rich, Proteinase Inhibitors (Chapter 4, "Inhibitors of Cysteine Proteinases"), Elsevier Science Publishers (1986). Such inhibitors include peptide aldehydes, which form hemithioacetals with the cysteine of the protease active site. See, for instance, Cheng, H., Keitz, P., and Jones, J. B., J. Org. Chem. (1994), 59, 7671. The disadvantage of aldehydes is their in vivo and chemical instabilities.

Methods for selectively and irreversibly inhibiting cysteine proteases have relied upon alkylation by peptide α-fluoromethyl ketones (Rasnick, D., Anal. Biochem. (1985), 149, 416), diazomethyl-ketones (Kirschke, H., Shaw, E. Biochem. Biphys. Res. Commun. (1981), 101, 454), acyloxymethyl ketones (Krantz, A. etal., Biochemistry, (1991), 30, 4678; Krantz, A. et al., U.S. Pat. No. 5,055,451, issued Oct. 8, 1991), and ketosulfonium salts (Walker, B., Shaw, E., Fed. Proc. Fed. Am. Soc. Exp. Biol., (1985), 44, 1433).

Other families of cysteine protease inhibitors include epoxysuccinyl peptides, including E-64 and its analogs (Hanada, K. et al., Agric. Biol. Chem (1978), 42, 523; Sumiya, S. etal., Chem. Pharm. Bull. ((1992), 40, 299 Gour-Salin, B. J. et al., J. Med. Chem., (1993), 36, 720), α-dicarbonyl compounds, reviewed by Mehdi, S., Bioorganic Chemistry, (1993), 21, 249, and N-peptidyl-O-acyl hydroxamates (Bromme, D., Neumann, U., Kirschke, H., Demuth, H- U., Biochim. Biophys. Acta, (1993), 1202, 271. An additional summary of methods for reversibly and irreversibly inhibiting cysteine proteases has recently been compiled; see Shaw, E., Advances in Enzymology and Related Areas of Molecular Biology (1990), 63, 271.

SUMMARY OF THE INVENTION

It is an object of the present invention to provide novel cysteine protease inhibitors that function reversibly, resulting in tight binding (low dissociation constants) between inhibitor and target enzyme. It is a further object to provide these novel cysteine protease inhibitors for use in a variety of therapeutic applications.

In accordance with the foregoing objects, one embodiment of the present invention provides reversible cysteine protease inhibitors comprising two N-substituents linked via an ethylenediamine or a substituted ethylenediamine, wherein the dissociation constant for inhibition, $K_I$, of a protease with the inhibitor, is no greater than about 100 µM, and wherein said N-substituents are selected from the group consisting of acyl, acyl peptidyl, alkyloxycarbonyl, alkyloxycarbonyl peptidyl, sulfonyl, sulfonyl peptidyl, peptidyl, sulfamoyl, sulfamoyl peptidyl, sulfinyl, sulfinyl peptidyl, carbamoyl, and carbamoyl peptidyl.

Also provided are reversible cysteine protease inhibitor having the formula comprising:

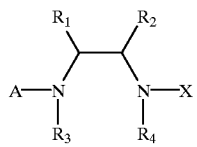

In this aspect, A and X are N-substituents selected from the group consisting of acyl, acyl peptidyl, alkyloxycarbonyl, alkyloxycarbonyl peptidyl, sulfonyl, sulfonyl peptidyl, peptidyl, sulfamoyl, sulfamoyl peptidyl, sulfinyl, sulfinyl peptidy, carbamoyl, and carbamoyl peptidyl. $R_1$ is either hydrogen or an amino acid side chain, and $R_2$ is either hydrogen or an amino acid side chain. However, either both $R_1$ and $R_2$ are hydrogen, or one of $R_1$ or $R_2$ is an amino acid side chain and the other one of $R_1$ and $R_2$ is hydrogen. $R_3$ amd $R_4$ are hydrogen, or are bonded together to form ethylene or substituted ethylene. Additionally, the dissociation constant for inhibition, $K_I$, of a protease with the inhibitor, is no greater than about 100 µM.

Also provided are reversible cysteine protease inhibitors having the formula comprising:

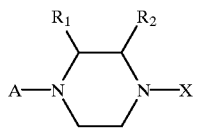

Further provided are reversible cysteine protease inhibitors having the formula comprising:

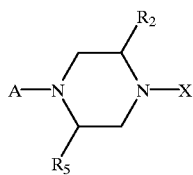

Additionally provided are reversible cysteine protease inhibitors having the formula comprising:

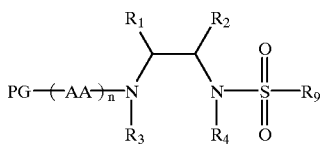

In this aspect, n is from 1 to 10, PG is a protecting group, and AA is an amino acid. $R_1$ is either hydrogen or an amino acid side chain, and $R_2$ is either hydrogen or an amino acid side chain. However, either both $R_1$ and $R_2$ are hydrogen, or one of $R_1$ or $R_2$ is an amino acid side chain and the other one of $R_1$ and $R_2$ is hydrogen. $R_3$ and $R_4$ are hydrogen, or are bonded together to form ethylene or substituted ethylene. —$SO_2R_9$ is a sulfonyl moiety. Additionally, the dissociation constant for inhibition, $K_I$, of a protease with the inhibitor, is no greater than about 100 µM.

Further provided are reversible cysteine protease inhibitor having a formula comprising:

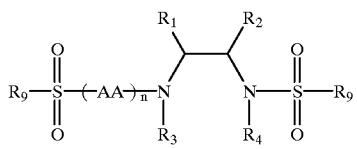

In this aspect, n is from 1 to 10 and AA is an amino acid. $R_1$ is either hydrogen or an amino acid side chain, and $R_2$ is either hydrogen or an amino acid side chain. However, either both $R_1$ and $R_2$ are hydrogen, or one of $R_1$ or $R_2$ is an amino acid side chain and the other one of $R_1$ and $R_2$ is hydrogen. $R_3$ and $R_4$ are hydrogen, or are bonded together to form ethylene or substituted ethylene. —$SO_2R_9$ is a sulfonyl moiety. Additionally, the dissociation constant for inhibition, $K_I$, of a protease with the inhibitor, is no greater than about 100 µM.

An additional aspect of the invention provides reversible cysteine protease inhibitors having a formula comprising:

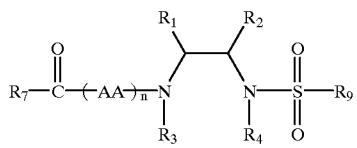

In this aspect, n is from 1 to 10, PG is a protecting group and M is an amino acid. $R_1$ is either hydrogen or an amino acid side chain, and $R_2$ is either hydrogen or an amino acid side chain. However, either both $R_1$ and $R_2$ are hydrogen, or one of $R_1$ or $R_2$ is an amino acid side chain and the other one of $R_1$ and $R_2$ is hydrogen. $R_3$ and $R_4$ are hydrogen, or are bonded together to form ethylene or substituted ethylene. —$SO_2R_9$ is a sulfonyl moiety. Additionally, the dissociation constant for inhibition, $K_I$, of a protease with the inhibitor, is no greater than about 100 µM.

A further aspect of the invention provides methods of inhibiting a cysteine protease inhibitor comprising reversibly binding a cysteine protease inhibitor of the invention to a cysteine protease.

An additional aspect provides cysteine proteases inhibited by the cysteine protease inhibitors of the invention.

Further, the invention provides methods of treating cysteine protease associated disorders comprising administering to a patient a therapeutically effective dose of cysteine protease inhibitor of the invention, and pharmaceutical compositions comprising the cysteine protease inhibitors of the invention.

Additionally, the invention provides methods of detecting a cysteine protease in a sample comprising assaying the sample for protease activity using a protease substrate. The sample is then assayed for protease activity in the presence of a known concentration of a cysteine protease inhibitor of the invention, and determining the amount of cysteine protease.

BRIEF DESCRIPTION OF THE DRAWINGS

FIGS. 1A, 1B, 1C, 1D, 1E, 1F, 1G, 1H, 1I, 1J, 1K, 1L, 1M, 1N, 1O, 1P, 1Q, 1R, 1S, 1T, 1U, 1V, 1W, 1X, 1Y, 1Z, 1AA, 1B, 1CC, and 1DD depict the structures of some of the cysteine protease inhibitors of the invention. The structures, abbreviated names, and kinetic data are shown, as described more fully in the Examples. The kinetic data are in micromolar units.

FIG. 2 depicts a schematic synthesis for cysteine protease inhibitors with $R_2$ substituent groups on ethylenediamine moieties. 1. Carbonyldiimidazole, $NH_3$/THF; 2. HCl/dioxane, $CH_2Cl_2$/ether; 3. $R_9SO_2Cl$, triethyl amine (TEA), THF; 4. LAH or suitable reducing agent, THF, reflux; 5. HCl/dioxane, $CH_2Cl_2$/ether; 6. PG-$M_1$-OH, NMM, IBCF, THF at –10° C.

FIG. 3 depicts a schematic synthesis for cysteine protease inhibitors with R. substituent groups on ethylenediamine moieties. 1. $LiAlH_4$ (LAH) or suitable reducing agent, THF, reflux; 2. HCl/dioxane, $CH_2Cl_2$/ether; 3. $R_9SO_2Cl$, TEA, THF, –10° C.; 4. $H_2$/Pd/C or suitable catalyst, HCl/dioxane, EtOH; 5. PG-$AA_1$-OH, 4-methyl morpholine (NMM); isobutyl chloroformate (IBCF), THF, –10° C.

FIG. 4 depicts a schematic synthesis for cysteine protease inhibitors with $R_2$ and $R_5$ substituent groups on piperazine moieties. 1. Activation of acid: pyr, TC, THF, –10° C.; 2. bis(trimethylsilyl)acetamide (BSA), TEA, THF; 3. HBr/AcOH; 4. TEA, EtOH; 5. LAH or suitable reducing agent, THF, reflux; 6. HCl/dioxane, $CH_2Cl_2$/ether; 7. $R_9SO_2Cl$, TEA, THF; 8. $H_2$/Pd/C or suitable catalyst, EtOH; 9. pyr, TC, THF, –10° C.; 10. compound 2, BSA, TEA, THF.

FIG. 5 depicts a schematic synthesis for cysteine protease inhibitors with $R_1$ and $R_6$ substituent groups on piperazine moieties. Step 1 is the activation of the acid: pyridine (pyr), thionyl chloride (TC), THF, at –10° C.; 2. bis (trimethylsilyl) acetamide (BSA), TEA, THF; 3. HBr/AcOH; 4. TEA, EtOH; 5. LAH or suitable reducing agent, THF, reflux; 6. HCl/dioxane, $CH_2Cl_2$/ether; 7. pyr, TC, THF; 8. compound 1, BSA, TEA, THF; 9. $H_2$/Pd/C or suitable catalyst, HCl/dioxane, $Et_2O$; 10. $R_9SO_2Cl$, TEA, THF.

DETAILED DESCRIPTION OF THE INVENTION

The present invention relates to novel cysteine protease inhibitors. It is believed that the enzyme is reversibly inhibited by means of interactions between the N-blocking groups and the $R_1$ or $R_2$ group of the inhibitor and the surface of the binding sites of the enzyme, via hydrogen bonding and hydrophobic interactions.

Generally, the inhibitors of the present invention inhibit cysteine proteases and do not inhibit serine, aspartyl, and zinc proteases. The mechanisms of serine protease action have been described by Walsh, C., in "Enzymatic Reaction Mechanisms" pp. 94–97, W.H. Freeman and Co., San Francisco, 1979. The serine at the active site reacts with the carbonyl of the substrate, forming a tetrahedral intermediate. The inhibitors of this invention have no carbonyl at the site of nucleophilic attack, and are not susceptible to attack by serine proteases.

However, in some embodiments, the protease inhibitors of the present invention may have activity against other types of proteases, such as serine, aspartyl or other metalloproteases, but to a lesser extent. In particular, the protease inhibitors of the invention may have activity against serine proteases, for example, they may have activity against chymotrypsin.

Cysteine proteases are a family of proteases that bear a thiol group at the active site. These proteases are found in bacteria, viruses, eukaryotic microorganisms, plants, and animals. Cysteine proteases may be generally classified as belonging to one of four or more distinct superfamilies. Examples of cysteine proteases that may be inhibited by the novel cysteine protease inhibitors of the present invention include, but are not limited to, the plant cysteine proteases such as papain, ficin, aleurain, oryzain and actinidin; mammalian cysteine proteases such as cathepsins B, H, J, L, N, S, T, O, O2 and C, (cathepsin C is also known as dipeptidyl peptidase I), interleukin converting enzyme (ICE), calcium-activated neutral proteases, calpain I and II; bleomycin hydrolase, viral cysteine proteases such as picomian 2A and 3C, aphthovirus endopeptidase, cardiovirus endopeptidase, comovirus endopeptidase, potyvirus endopeptidases I and II, adenovirus endopeptidase, the two endopeptidases from chestnut blight virus, togavirus cysteine endopeptidase, as well as cysteine proteases of the polio and rhinoviruses; and cysteine proteases known to be essential for parasite lifecycles, such as the proteases from species of Plasmodia, Entamoeba, Onchocera, Trypansoma, Leishmania, Haemonchus, Dictyostelium, Therileria, and Schistosoma, such as those associated with malaria (*P. falciparium*), trypanosomes (*T. cruzi*, the enzyme is also known as cruzain or cruzipain), murine *P. vinckei*, and the *C. elegans* cysteine protease. For an extensive listing of cysteine proteases that may be inhibited by the cysteine protease inhibitors of the present invention, see Rawlings et al., Biochem. J. 290:205–218 (1993), hereby expressly incorporated by reference.

Accordingly, inhibitors of cysteine proteases are useful in a wide variety of applications. For example, the inhibitors of the present invention are used to quantify the amount of cysteine protease present in a sample, and thus are used in assays and diagnostic kits for the quantification of cysteine proteases in blood, lymph, saliva, or other tissue samples, in addition to bacterial, fungal, plant, yeast, viral or mammalian cell cultures. Thus in a preferred embodiment, the sample is assayed using a standard protease substrate. A known concentration of cysteine protease inhibitor is added, and allowed to bind to a particular cysteine protease present. The protease assay is then rerun, and the loss of activity is correlated to cysteine protease activity using techniques well known to those skilled in the art.

Thus, methods of inhibiting a protease are provided, wherein the cysteine protease inhibitors of the invention may be added to a sample of cysteine protease, to form a cysteine protease/cysteine protease inhibitor complex.

Additionally, the cysteine protease inhibitors are also useful to remove, identify or inhibit contaminating cysteine proteases in a sample. For example, the cysteine protease inhibitors of the present invention are added to samples where proteolytic degradation by contaminating cysteine proteases is undesirable. Alternatively, the cysteine protease inhibitors of the present invention may be bound to a chromatographic support, using techniques well known in the art, to form an affinity chromatography column. A sample containing an undesirable cysteine protease is run through the column to remove the protease. Alternatively, the same methods may be used to identify new proteases.

In a preferred embodiment, the cysteine protease inhibitors are useful for inhibiting cysteine proteases implicated in a number of diseases. In particular, cathepsins B, L, and S, cruzain, calpains I and II, and interleukin 1β converting enzyme are inhibited. These enzymes are examples of lysosomal cysteine proteases implicated in a wide spectrum of diseases characterized by tissue degradation. Such diseases include, but are not limited to, arthritis, muscular dystrophy, inflammation, tumor invasion, glomerulonephritis, parasite-borne infections, Atlzheimer's disease, periodontal disease, and cancer metastasis. For example, mammalian lysosomal thiol proteases play an important role in intracellular degradation of proteins and in the processing of some peptide hormones. Enzymes similar to cathepsins B and L are released from tumors and may be involved in tumor metastasis. Cathepsin L is present in diseased human synovial fluid and transformed tissues. Similarly, the release of cathepsin B and other lysosomal proteases from polymorphonuclear granulocytes and macrophages is observed in trauma and inflammation.

The cysteine protease inhibitors also find application in a multitude of other diseases, including, but not limited to, gingivitis, malaria, leishmaniasis, filariasis, osteoporosis and osteoarthritis, and other bacterial and parasite-borne infections. The compounds also offer application in viral diseases, based on the approach of inhibiting proteases necessary for viral replication. For example, many picornoviruses including poliovirus, foot and mouth disease virus, and rhinovirus encode for cysteine proteases that are essential for cleavage of viral polyproteins.

Additionally, these compounds offer application in disorders involving interleukin-1β converting enzyme (ICE), a cysteine protease responsible for processing interleukin 1β; for example, in the treatment of inflammation and immune based disorders of the lung, airways, central nervous system and surrounding membranes, eyes, ears, joints, bones, connective tissues, cardiovascular system including the pericardium, gastrointestinal and urogenital systems, the skin and the mucosal membranes. These conditions include infectious diseases where active infection exists at any body site, such as meningitis and salpingitis; complications of infections including septic shock, disseminated intravascular coagulation, and/or adult respiratory distress syndrome; acute or chronic inflammation due to antigen, antibody and/or complement deposition; inflammatory conditions including arthritis, chalangitis, colitis, encephalitis, endocarditis, glomerulonephritis, hepatitis, myocarditis, pancreatitis, pericarditis, reperfusion injury and vasculitis. Immune-based diseases include but are not limited to conditions involving T-cells and/or macrophages such as acute and delayed hypersensitivity, graft rejection, and graft-versus-host disease; auto-immune diseases including Type I diabetes mellitus and multiple sclerosis. Bone and cartilage reabsorption as well as diseases resulting in excessive deposition of extracellular matrix such as interstitial pulmonary fibrosis, cirrhosis, systemic sclerosis, and keloid formation may also be treated with the inhibitors of the present invention. The inhibitors may also be useful in the treatment of certain tumors that produce IL 1 as an autocrine growth factor and in preventing the cachexia associated with certain tumors. Apoptosis and cell death are also associated with ICE and ICE-like activities and may be treated with the inhibitors of the present invention.

Furthermore, the cysteine protease inhibitors of the present invention find use in drug potentiation applications. For example, therapeutic agents such as antibiotics or antitumor drugs can be inactivated through proteolysis by endogeneous cysteine proteases, thus rendering the administered drug less effective or inactive. For example, it has been shown that bleomycin, an antitumor drug, can be hydrolyzed by bleomycin hydrolase, a cysteine protease (see Sebti et al., Cancer Res. January 1991, pages 227–232). Accordingly, the cysteine protease inhibitors of the invention may be administered to a patient in conjunction with a therapeutic agent in order to potentiate or increase the activity of the drug. This co-administration may be by simultaneous administration, such as a mixture of the cysteine protease inhibitor and the drug, or by separate simultaneous or sequential administration.

In addition, cysteine protease inhibitors have been shown to inhibit the growth of bacteria, particularly human pathogenic bacteria (see Bjorck et al., Nature 337:385 (1989)). Accordingly, the cysteine protease inhibitors of the present invention may be used as antibacterial agents to retard or inhibit the growth of certain bacteria.

The cysteine protease inhibitors of the invention also find use as agents to reduce the damage of bacterial cysteine proteases to host organisms. For example, *staphylococcus* produces a very active extracellular cysteine protease which degrades insoluble elastin, possibly contributing to the connective tissue destruction seen in bacterial infections such as septicemia, septic arthritis and otitis. See Potempa et al., J. Biol. Chem. 263(6):2664–2667 (1988). Accordingly, the cysteine protease inhibitors of the invention may be used to treat bacterial infections to prevent tissue damage.

The present invention generally provides new peptide-based and peptidomimetic cysteine protease inhibitors for use as reversible cysteine protease inhibitors. By "cysteine protease inhibitor" herein is meant an inhibitor which inhibits cysteine proteases. In a preferred embodiment, the cysteine protease inhibitors are specific to cysteine proteases; that is, they do not inhibit other types of protease such as setnne, aspartyl, or other metalloproteases. However, in alternative embodiments, the cysteine protease inhibitors of the invention may inhibit other types of proteases as well; for example, they may have activity against serine proteases.

By "reversible" herein is meant that the inhibitor binds non-covalently to the enzyme, and is to be distinguished from irreversible inhibition. See Walsh, Enzymatic Reaction Mechanisms, Freeman & Co., N.Y., 1979. "Reversible" in this context is a term understood by those skilled in the art. In addition, the reversible cysteine protease inhibitors are competitive inhibitors, that is, they compete with substrate in binding reversibly to the enzyme, with the binding of inhibitor and substrate being mutually exclusive. In addition, the stoichiometry of inhibition is 1:1; that is, a single inhibitor molecule is sufficient to inhibit a single enzyme molecule.

Unless otherwise stated, the following terms used in the specification and claims are defined for the purposes of this application and have the meanings given below:

"Alkyl", as in alkyl, alkyloxy, alkylthio, alkylsulfonyl, alkylcarbamoyl, dialkylcarbamoyl, heteroarylalkyl, arylalkyl, and the like, means a straight or branched, saturated or unsaturated hydrocarbon radical having from 1 to 10 carbon atoms or the number of carbon atoms indicated (e.g., methyl, ethyl, prop-yl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, etc.).

"Cycloalkyl", as in cycloalkyl and cycloalkylalkyl, means a saturated or unsaturated, monocyclic or polycyclic hydrocarbon radical containing 3 to 20 carbon atoms or the number of carbon atoms indicated, wherein the carbon atom with the free valence is a member of a non-aromatic ring, and any carbocyclic ketone and thioketone derivative thereof (e.g., the term cycloalkyl is meant to include cyclopropyl, cyclobutyl, cyclopentyl, cyclohexyl, cyclohexenyl, bicyclo[2.2.2]octyl, 1,2,3,4-tetrahydro-1-naphthyl, oxocyclohexyl, dioxocyclohexyl, thiocyclohexyl, 9-fluorenyl, etc.).

"Heterocycloalkyl", as in heterocycloalkyl, heterocycloalkylalkanoylamino, heterocycloalkylcarbonyl, heterocycloalkylcarbonyl, and the like, means cycloalkyl as defined above wherein 1 to 5 of the indicated carbon atoms is replaced by a heteroatom chosen from N, O, S, P or As, wherein the atom with the free valence is a member of a non-aromatic ring, and any heterocyclic ketone, thioketone, sulfone or sulfoxide derivative thereof, (e.g., the term heterocycloalkyl is meant to include piperidyl, pyrrolidinyl, pyrrolinyl, imidazolidinyl, indolinyl, quinuclidinyl, morpholinyl, piperazinyl, N-methylpiperazinyl, piperadinyl, 4,4-dioxo-4-thiapiperidinyl, 1,2,3,4-tetrahydro-3-isoquinolyl, 2,4-diaza-3-oxo-7-thia-6-bicyclo[3.3.0]octyl, etc.). Thus, hetero($C_6$)cycloalkyl includes the radicals morpholinyl, piperazinyl, piperidinyl and the like.

"Aryl" means an aromatic monocyclic or polycyclic hydrocarbon radical containing 6 to 14 carbon atoms or the number of carbon atoms indicated and any carbocyclic ketone or thioketone derivative thereof, wherein the carbon atom with the free valence is a member of an aromatic ring, (e.g., aryl includes phenyl, naphthyl, anthracenyl, phenanthrenyl, 1,2,3,4-tetrahydro-5-naphthyl, 1-oxo-1,2-dihydro-5-naphthyl, 1-thioxo-1,2-dihydro-5-naphthyl, etc.). For the purposes of this application aryl includes heteroaryl. "Heteroaryl" means an aromatic monocyclic or polycyclic hydrocarbon radical containing overall from 5 to 14 atoms or the number of atoms indicated, wherein 1 to 5 of the indicated carbon atoms are replaced by a heteroatom chosen from N, O, S, P or As, wherein the atom with the free valence is a member of an aromatic ring, and any heterocyclic ketone and thioketone derivative thereof (e.g., the term heteroaryl is meant to include thienyl, furyl, pyrrolyl, pyrimidinyl, isoxazolyl, oxaxolyl, indolyl, benzo[b]thienyl, isobenzofuranyl, purinyl, isoquinolyl, pterdinyl, pyrimidinyl, imidazolyl, pyridyl, pyrazolyl, pyrazinyl, 4-oxo-1,2-dihydro-1-naphthyl, 4-thioxo-1,2-dihydro-1-naphthyl, etc.). Thus, hetero($C_6$)aryl includes the radicals pyridyl, pyrimidinyl, and the like.

"1,2-Phenylenedimethylene" means a divalent radical of the formula —$CH_2C_6H_4CH_2$—. For example, the group $R_{13}$—Y—Z—$X_3$— in which Y is —$N(R_{14})$, Z is —CH($R_{16}$)—, $X_3$ is carbonyl and $R_{14}$ together with $R_{16}$ forms 1,2-diphenylenedimethylene" is 1,2,3,4-tetrahydro-3-isoquinolylcarbonyl and substituted derivatives and individual stereoisomers and mixture of stereoisomers thereof. Substituted derivatives of the 1,2-phenylenedimethylene divalent radical may contain a hydroxy group on any carbon within the ring system or an oxo group on either of the unsaturated ring carbon atoms.

"Methylene" as in "($C_{3-4}$)methylene" and "($C_{3-7}$) methylene" mean a straight, saturated divalent radical having the number of carbon atoms indicated. For example, "(C$_{3-4}$)methylene" includes trimethylene (—(CH$_2$)$_3$—) and tetramethylene (—(CH$_2$)$_4$—). Thus, the group R$_{13}$—Y—Z—X$_3$— in which Y is —N(R$_{14}$), Z is —CH(R$_{16}$)—, X$_3$ is carbonyl and R$_{14}$ together with R$_{16}$ forms trimethylene is 2-pyrrolidinylcarbonyl and the individual stereoisomers and mixtures of stereoisomers thereof. Substituted derivatives of the trimethylene and tetramethylene divalent radicals may contain a hydroxy group, or a protected derivative thereof, or an oxo group on any of the ring carbon atoms. Suitable hydroxy protective groups are defined below.

"Oxa(C$_{3-7}$)methylene" and "aza(C$_{3-7}$)methylene" mean methylene as defined above wherein one of the indicated carbon atoms is replaced by an oxygen or nitrogen atom, respectively. For example, "oxa(C$_5$)methylene" includes 3-oxapentamethylene (—CH$_2$CH$_2$OCH$_2$CH$_2$—) and 2-oxapentamethylene (—CH$_2$OCH$_2$CH$_2$CH$_2$—). Thus, —C(O)NR$_{10}$R$_{11}$ means the radical 4-morpholinylcarbonyl when R$_{10}$ and R$_{11}$ together form 3-oxapentamethylene and the radical 1-piperazinylcarbanoyl when R$_{10}$ and R$_{11}$ together form 3-azapentamethylene.

"Adjacent", as use in the phrase "R$_{16}$ together with an adjacent R$_{14}$", means that the atoms to which the R$_{16}$ and R$_{14}$ groups are respectively attached are in turn attached to one another.

In the broadest embodiment, the cysteine protease inhibitors of the present invention comprise two N-substituents linked via an ethylenediamine or piperazine group.

Suitable N-substituents include, but are not limited to, acyl, alkyloxycarbonyl, sulfonyl, sulfamoyl, peptidyl, carbamoyl, sulfinyl, aralkyl, or hydrogen, or combinations thereof, including, but not limited to, acyl peptidyl, alkyloxycarbonyl peptidyl, sulfonyl peptidyl, sulfamoyl peptidyl, carbamoyl peptidyl and sulfinyl peptidyl.

In a preferred embodiment, the reversible cysteine protease inhibitors of the present invention comprise compositions having the formula depicted in Formula 1:

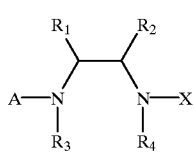

Formula 1

In this embodiment, A and X are N-substituents selected from the group consisting of acyl, acyl peptidyl, alkyloxycarbonyl, alkyloxycarbonyl peptidyl, sulfonyl, sulfonyl peptidyl, peptidyl, sulfamoyl, sulfamoyl peptidyl, carbamoyl, carbamoyl peptidyl, sulfinyl, and sulfinyl peptidyl. R$_1$ and R$_2$ are hydrogen or an amino acid side, wherein only 1 of R$_1$ or R$_2$ is an amino acid side chain and the other one of R$_1$ or R$_2$ is hydrogen. R$_3$ and R$_4$ are hydrogen, or are bonded together to form ethylene or substituted ethylene.

By "acyl" herein is meant a —COR$_7$ group. Suitable R$_7$ groups include, but not limited to, an alkyl (forming alkanoyl), a cycloalkyl (forming cycloalkylcarbonyl), a cycloalkylalkyl, a cycloalkylalkenyl, an aryl (forming aroyl), or an aralkyl. In such an instance, alkyl is preferably of 1 to 5 carbon atoms, especially ethyl. Cycloalkyl preferably is of 3 to 7 carbon atoms, preferably cyclopentyl or cyclohexyl. Cycloalkylalkyl or cycloalkylalkenyl preferably is of 3 to 7 carbon atoms in the cycloalkyl, particularly 5 or 6 carbon atoms, and of 1 to 5 carbon atoms, particularly 1 carbon atom, in the alkyl or alkylene moieties thereof.

Heterocycloalkyl (forming heterocycloalkylcarbonyl) is also preferred, optionally substituted with a radical selected from hydroxy, alkyl, heterocycloalkyl, alkanoyl, alkyloxycarbonyl, arylalkyloxycarbonyl and heterocycloalkylcarbonyl. Aryl preferably is phenyl. Aralkyl preferably is phenylalkyl of 7 to 12 carbon atoms, particularly benzyl. The optional substituents of an aryl or aralkyl moiety preferably are one or two groups alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, nitro, alkyl or arylsulfonyl, or halogen-substituted alkyl of 1 to 5 carbon atoms, particularly trifluoromethyl. Also included are perfluoro groups, such as perfluoro alkyl, aryl, and aralkyl.

Particularly preferred in regards to R$_7$ are: (1) (C1–C5) alkyl, preferably ethyl; (2) (C3–C7)cycloalkyl, preferably cyclopentyl or cyclohexyl; (3) (C3–C7)cycloalkyl-(C1–C5) alkyl, especially (C5–C6)cycloalkyl-methyl; (4) (C3–C7) cycloalkyl-(C1–C5)alkenyl, especially (C5–C6)cycloalkyl-methylene; (5) phenyl; (6) (C7–C12)phenylalkyl, especially benzyl; (7) aryl or aralkyl substituted by one or two groups of C1–C5 alkyl, C1–C5 alkoxy, halogen, hydroxy or amino, with one or two groups of methyl, methoxy, chlorine, bromine, fluorine, hydroxy or amino being preferred and hydroxy, amino, chlorine, bromine or fluorine being particularly preferred; (11) aryl or aralkyl substituted by one or two groups of halogen-substituted C1–C5 alkyl, especially trifluoromethyl; nitro; sulfonyl; or arylsulfonyl, in protected form where appropriate; (12) perfluoro groups, such as perfluoro alkyl, aryl, and aralkyl. Most preferred R$_7$ acyl groups include phenyl and 4-morpholinyl.

Thus, preferred acyl groups are alkyloxycarbonylalkanoyl, arylalkanoyl, aroyl and alkanoyl groups (optionally substituted with a radical selected from carboxy, alkyloxycarbonyl and heterocycloalkylalkanoylamino), cycloalkylcarbonyl, heterocycloalkylcarbonyl (optionally substituted with a radical selected from hydroxy, alkyl, heterocycloalkyl, alkanoyl, alkyloxycarbonyl, arylalkyloxycarbonyl and heterocycloalkylcarbonyl), arylalkanoyl, and aroyl.

By "acyl peptidyl" or "peptidyl acyl" herein is meant a peptidyl group linked to an acyl group. It is to be understood that the peptidyl group is linked to one of the nitrogens of the ethylenediamine or piperazine moieties, and the acyl group is linked to the peptidyl group. Thus, the free terminal functionality of an acyl peptidyl group is the R$_7$ group. Accordingly, the order of the functionalities differs depending on whether it is the A group or the X group which is the acyl peptidyl; the group is called an acyl peptidyl moiety when describing the A group and a peptidyl acyl moiety when describing the X group. Formula 2 shows a cysteine protease inhibitor with an acyl peptidyl group at the A and a peptidyl acyl group at the X position, wherein n is from 1 to 10.

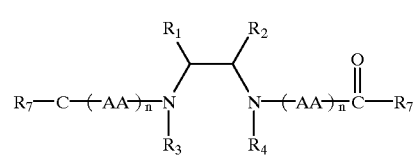

Formula 2

As is described below, the choice of the peptidyl groups will depend on the protease to be inhibited.

By "peptidyl" herein is meant a peptide or peptidomimetic structure. In some embodiments, peptidyl is a single amino acid; in other embodiments, the peptidyl group comprises at least two amino acids linked via a peptide bond or isostere. The peptidyl group may include up to about 10 amino acids, with 1 to 7 being preferred, although cysteine protease inhibitors are generally from about 1 to about 4 amino acids in length, since smaller inhibitors are usually desired in therapeutic applications.

The peptidyl group may comprise naturally occurring amino acids and peptide bonds, or synthetic peptidomimetic structures, i.e. "analogs". Thus "amino acid", "peptide residue", or "peptidyl" as used herein means both naturally occurring and synthetic amino acids, i.e. amino acid analogs. For example, homo-phenylalanine is considered an amino acid for the purposes of the invention. "Amino acid" also includes imino acid residues such as proline and hydroxyproline. The term as used herein also refers to portions of an amino acid, such as an amino acid side chain. Thus, $R_1$, $R_2$, $R_5$, $R_6$ and $R_{16}$, for example, may be amino acid side chains, which includes naturally occurring amino acid side chains as well as non-naturally occurring side chain analogs as described herein. The side chains may be in either the (R) or the (S) configuration. In a preferred embodiment, the amino acids are in the (S) or L-configuration.

If non-naturally occurring side chains are used, i.e. amino acid analogs, non-amino acid substituents may be used, for example to prevent or retard in vivo degradations. Such non-amino acid substituents will normally include, but are not limited to, an alkyl (optionally substituted with a radical selected from hydroxy, alkyloxy, amino, alkylamino, dialkylamino, uriedo, alkyluriedo, mercapto, alkylthio, carboxy, carbamoyl, alkylcarbamoyl, dialkylcarbamoyl, alkylsulfinyl, alkylsulfonyl, guanidino, —P(O)(OR$_{12}$)$_2$, —OP(O)(OR$_{12}$)$_2$ or —OP(O)(R$_{12}$)$_2$, wherein each $R_{12}$ is independently hydrogen or alkyl, or a protected derivative thereof), cycloalkyl, cycloalkylalkyl, cycloalkylalkenyl, a group selected from aryl (including heteroaryl) and arylalkyl (including heteroarylalkyl and heteroarylalkenyl), (which group is optionally substituted at its aryl ring with one to three radicals selected from hydroxy, amino, guanidino, halo, optionally halo-substituted alkyl, alkyloxy and aryl, or a protected derivative thereof), alkoxy, cyano, carboxy, alkyloxycarbonyl, alkanoyl, carbamoyl, alkylcarbamoyl, dialkylcarbamoyl, alkyloxy(alkyl)carbamoyl, or aminoalkylcarbamoyl. In such an instance, alkyl is preferably of 1 to 5 carbon atoms, preferably branched, particularly isobutyl. Cycloalkyl preferably is of 3 to 7 carbon atoms, preferably cyclopentyl or cyclohexyl. Cycloalkylalkyl or cycloalkylalkenyl preferably is of 3 to 7 carbon atoms in the cycloalkyl, particularly 5 or 6 carbon atoms, and of 1 to 5 carbon atoms, particularly 1 carbon atom, in the alkyl or alkylene moieties thereof. Aryl preferably is phenyl or naphthyl, especially 2-naphthyl. Heteroaryl preferably is pyridinyl, thienyl, especially 2-thienyl, or furyl, especially 2-furyl. Heteroarylalkyl and heteroalkenyl preferably has 1 to 6 carbon atoms, especially 1 carbon atom in the alkyl or alkylene moieties thereof. The heteroaryl moiety of heteroarylalkyl and heteroarylakylene preferably has the significances indicated above as preferred for heteroaryl. Aralkyl preferably is phenylalkyl of 7 to 12 carbon atoms, particularly naphthylmethyl, benzyl and phenylethyl. Alkoxy preferably is of 1 to 5 carbon atoms, preferably methoxy. Acyloxy preferably is of 2 to 6 carbon atoms, preferably acetoxy. The optional substituents of an aryl or aralkyl moiety preferably are one to three radicals of alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, halogen-substituted alkyl of 1 to 5 carbon atoms, particularly trifluoromethyl.

Specifically excluded from the definition of amino acid side chain is oxo. Thus, the ethylenediamine does not contain peptide bonds.

The peptidyl functionality may also be depicted as shown in Formulae (a) and (b):

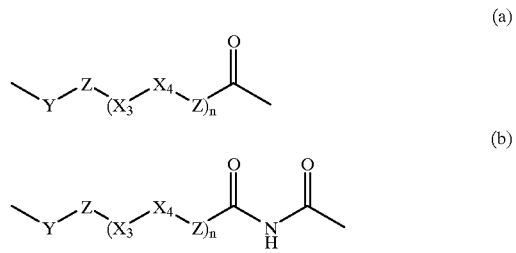

in which n is 0 to 9; $X_3$–$X_4$ represents a linkage selected from —C(O)NR$_{14}$—, —CH$_2$NR$_{14}$—, —C(O)CH$_2$— and —NR$_{14}$C(O)—; Y is —CH(R$_{14}$)— or —NR$_{14}$—; and Z is —(CH$_2$)$_2$—, —C(R$_{15}$)(R$_{16}$)— or —N(R$_{16}$)—; wherein $R_{14}$ is hydrogen or as defined below, $R_{15}$ is hydrogen or methyl and each $R_{16}$ is an amino acid side chain. Thus each $R_{16}$ is independently hydrogen, alkyl (optionally substituted with a radical selected from hydroxy, alkyloxy, amino, alkylamino, dialkylamino, uriedo, alkyluriedo, mercapto, alkylthio, carboxy, carbamoyl, alkylcarbamoyl, dialkylcarbamoyl, alkylsulfinyl, alkylsulfonyl, guanidino, —P(O)(OR$_{12}$)$_2$, —OP(O)(OR$_{12}$)$_2$ or —OP(O)(R$_{12}$)$_2$, wherein each $R_{12}$ is independently hydrogen or alkyl, or a protected derivative thereof), cycloalkyl. cycloalkylalkyl, a group selected from aryl and arylalkyl (which group is optionally substituted at its aryl ring with one to three radicals selected from hydroxy, amino, guanidino, halo, optionally halo-substituted alkyl, alkyloxy and aryl, or a protected derivative thereof) or together with an adjacent $R_{14}$ forms a divalent radical selected from (C$_{3-4}$)methylene and 1,2-phenylenedimethylene (which radical is optionally substituted with hydroxy, or a protected derivative thereof, or oxo).

The peptidyl group may also contain additional functional groups, as depicted by "PG" of Formula 3 below. Thus, the protecting group, "PG", of Formula 3 may be a peptide amino end blocking group or a label, as these terms are defined below. By the term "peptide amino end blocking group" herein is meant, for example, groups including, but not limited to alkyloxycarbonylalkanoyl (preferably of overall 2 to 10 carbon atoms), alkyloxycarbonyl (preferably of overall 2 to 10 carbon atoms and particularly tert-butoxycarbonyl (BOC) or benzyloxycarbonyl (CBZ, Z)), alkanoyl (preferably of overall 2 to 10 carbon atoms and optionally substituted with a radical selected from carboxy, alkyloxycarbonyl and heterocycloalkylalkanoylamino), cycloalkylcarbonyl (preferably of overall 4 to 8 carbon atoms), heterocycloalkylcarbonyl (preferably of overall 6 to 10 atoms and optionally substituted with a radical selected from hydroxy, alkyl, heterocycloalkyl, alkanoyl, alkyloxycarbonyl, arylalkyloxycarbonyl and heterocycloalkylcarbonyl and particularly a heterocycloalkylcarbonyl group of the formula —C(O)NR$_{10}$OR$_{11}$ wherein $R_{10}$ and $R_{11}$ together form aza(C$_{2-6}$)methylene, oxa(C$_{2-6}$)methylene or ($C_{3-7}$)methylene, particularly oxapentamethylene to form 4-morpholinylcarbonyl (Mu)), arylalkyloxycarbonyl (preferably comprising aryl of 6 to 10 carbon atoms and alkyloxy of 1 to 5 carbon atoms), carbamoyl, alkylcarbamoyl (preferably of overall 2 to 6 carbon atoms), dialkylcarbamoyl (preferably of overall 2 to 11 carbon atoms, arylcarbamoyl (preferably of overall 7 to 11 carbon atoms), arylalkylcarbamoyl (preferably comprising aryl of 6 to 10 carbon atoms and alkyl of 1 to 5 carbon atoms), arylalkanoyl (preferably comprising aryl of 6 to 10 carbon atoms and alkanoyl of overall 1 to 6 carbon atoms), aroyl (preferably of overall 7 to 11 carbon atoms and particularly benzoyl), alkylsulfonyl (preferably of 1 to 10 carbon atoms), arylalkylsulfonyl (preferably comprising aryl of 6 to 10 carbon atoms and alkyl of 1 to 5 carbon atoms), alkylsulfamoyl (preferably of 1 to 5 carbon atoms), dialkylsulfamoyl (preferably of 2 to 10 carbon atoms), arylsulfonyl (of 6 to 10 carbon atoms, including heteroarylsulfonyl, preferably comprising heteroaryl of overall 4 to 8 atoms), arylsulfamoyl (preferably of 6 to 10 carbon atoms, including heteroarylsulfamoyl preferably comprising heteroaryl of 4 to 8 atoms), alkylsulfinyl (preferably of 1 to 5 carbon atoms), dialkylaminosulfinyl (preferably of 2 to 10 carbon atoms), arylsulfinyl (preferably comprising aryl of 6 to 10 carbon atoms including heteroarylsulfinyl, preferably comprising heteroaryl of 4 to 8 atoms). Temporary protecting groups are known in the art, see Greene, Protective Groups in Organic Synthesis, John Wiley & Sons, 1991, hereby incorporated by reference.

Formula 3 depicts a cysteine protease inhibitor with peptidyl groups in both the A and X positions, wherein n is from 1 to 5:

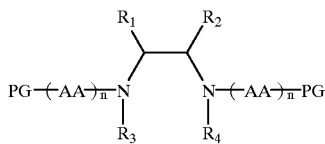

Formula 3

The amino acids, or peptide residues, are normally linked via a peptide bond or linkage, i.e. a peptidic carbamoyl group, i.e. —CONH—. In a preferred embodiment, the bond between the nitrogens of the ethylenediamine or piperazine moiety and the A and X group is a peptide bond. Similarly, when the peptidyl group contains two or more amino acids, the bond between the two is preferably a peptide bond. However, the bond between the amino acids of the peptidyl group may be a peptide isosteric or peptidomimetic bond such as CO—$CH_2$, $CH_2$—NH, azapeptide and retro-inverso bonds, as is depicted by $X_3$–$X_4$ in Formulae (a) and (b).

will be appreciated, additional amino acids may be added in the same manner. Similarly, it should be understood that these structures do not accurately reflect the situation where one or more of the amino acids is a proline.

In general, suitable amino acids of the peptidyl groups of the invention are initially chosen on the basis of the rules governing substrate specificity in cysteine proteases. That is, combinations of amino acids that confer specificity to the enzyme to be inhibited will be used.

It is to be understood that the order of the amino acid side chains within the inhibitor is significant in conferring inhibitor targeting. Thus, as is additionally described below, the amino acid side chain attached to the ethylenediamine or piperazine structure of the inhibitor, generally referred to herein as "$R_1$" or "$R_2$", will occupy the $S_1$ position of the enzyme's substrate binding site when the inhibitor is bound to the enzyme. That is, for example, the "$R_2$" amino acid side chain of the targeting group is the $P_1$ residue of the inhibitor. Similarly, if there is a peptidyl group in the A position, the amino acid side chain of the peptidyl group which is closest to the ethylenediamine moiety will occupy the $S_2$ position of the enzyme's substrate binding site when the inhibitor is bound to the enzyme, and thus is the $P_2$ residue. If present, additional amino acid side chains of the peptidyl will occupy the $P_3$, $P_4$, etc. positions.

Conversely, if the peptidyl group occupies the X position, the amino acid side chains occupy the $S_1'$, $S_2'$, etc. position of the enzyme's substrate binding site. These amino acid side chains are considered the $P_1'$, $P_2'$ etc. residues of the inhibitor. As will be appreciated by those in the art, it is possible to have peptidyl groups at both the A and X positions, to confer increased specificity on the inhibitor for the particular cysteine protease to be inhibited.

It should be understood that the inhibitors of the present invention potentially have a certain symmetry which could effect nomenclature. Thus, for example, if the A and the X groups are identical, the inhibitor can be thought of as having an $R_1$ group in one conformation or an $R_2$ group in the opposite conformation. Without being bound by theory, the A group is assumed to be binding in the P positions, and the X group to be binding to the P' positions of the enzyme.

The choice of the amino acid side chains of the $R_1$, $R_2$, $R_5$, $R_6$ and $R_{16}$ group, and the amino acids of the A and X groups will be made using the available information about the substrate specificity of the protease, and is routine to those skilled in the art using commercially available substrates. For example, interleukin-1β converting enzyme displays the greatest specificity demonstrated for a cysteine protease toward a substrate, requiring an aspartyl side chain in the $P_1$ position. The papain superfamily of cysteine proteases have an extended specificity site containing five to seven significant subsites, with the dominant one being $S_2$, which is a hydrophobic pocket that binds phenylalanyl-like sidechains

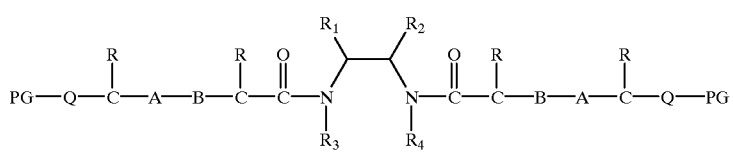

Formula 4

Formula 4 depicts a cysteine protease inhibitor with peptidyl groups comprising two amino acids as both the A and the X group. Thus, in formula 4, the A-B linkage is a peptide or peptidomimetic bond. PG is a protecting group, as defined herein, and Q may be either carbon or nitrogen. As very well. Cathepsin B, similar to papain, accepts a phenylalanine side chain in $S_2$, as well as an arginyl sidechain. For a general review, see "Proteinase Inhibitors", in Research Monographs in Cell and Tissue Physiology (1986), ed. Barrett et al., Vol. 12, Chapter 4: Inhibitors of Cysteine Proteinases, Daniel Rich, Elsevier, New York, hereby expressly incorporated by reference. In addition, the specificity of the interleukin 1β converting enzyme (ICE), was explored in Thornberry et al., supra, also expressly incorporated by reference herein. Table 1 lists some of the favored amino acid side chains for the $P_1$ and $P_2$ ($R_1$ or $R_2$) positions for a number of cysteine proteases.

TABLE 1

| enzyme | $P_2$ | $P_1(R_1$ or $R_2)$ |
|---|---|---|
| papain | Phe, Tyr, 2-napthyl, Leu, Nle, Ile, Ala | Arg, Lys, Lys(ε-Z), guanidino-phenylalanine, Hph, Nle |
| cathepsin B | Phe, Tyr, Tyr(I$_2$), 2-napthyl, Arg, guanidino-phenylalanine, Cit* | Arg, Lys, Lys(ε-Z), guanidino-phenylalanaine, Hph, Cit, Nle |
| cathepsin L or cruzain | Phe, Tyr, 2-napthyl | Arg, Lys, Lys(ε-Z), guanidino-phenylalanaine, Hph, Cit, Nle |
| cathepsin S | Phe, Tyr, 2-napthyl, Val, Leu, Nle, Ile, Ala | Arg, Lys, Lys(ε-Z), guanidino-phenylalanaine, Hph, Cit, Nle |
| DPP-1 | Gly, Ala | Phe, Tyr |
| calpain | Val, Leu, Nle, Ile, Phe | Tyr, Phe, Met, Met(O$_2$), Val |
| ICE | Ala, Val, His | Asp |
| cathepsin O2 | Leu, Met, Nle | Arg, Lys, Lys(ε-Z), guanidino-phenylalanine, Hph, Nle |

*citrulline

As will be appreciated by those in the art, when non-naturally occuring amino acid side chain analogs are used, they will be chosen initially by steric and biochemical similarities to the naturally occuring side chains.

By "alkyloxycarbonyl" herein is meant a —COOR$_8$ group, wherein C is carbon and O is oxygen. In this embodiment, suitable R$_8$ groups include, but are not limited to, an alkyl, a cycloalkyl, a cycloalkylalkyl, an aryl, or an aralkyl (forming an arylalkyloxycarbonyl). In such an instance, alkyl is preferably of 1 to 5 carbon atoms, especially ethyl. Cycloalkyl preferably is of 3 to 7 carbon atoms, preferably cyclopentyl or cyclohexyl. Cycloalkylalkyl preferably is of 3 to 7 carbon atoms in the cycloalkyl, particularly 5 or 6 carbon atoms, and of 1 to 5 carbon atoms, particularly 1 carbon atom, in the alkyl moieties thereof. Aryl preferably is phenyl. Aralkyl preferably is phenylalkyl of 7 to 12 carbon atoms, particularly benzyl. The optional substituents of an aryl or aralkyl moiety preferably are one or two groups independently selected from: alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, nitro, alkyl or arylsulfonyl, or halogen-substituted alkyl of 1 to 5 carbon atoms, particularly trifluoromethyl.

Particularly preferred are: (1) C1–C5 alkyl, especially ethyl; (2) C3–C7 cycloalkyl, preferably cyclopentyl or cycolhexyl; (3) C3–C7(cycloalkyl)-C1–C5 alkyl, preferably C5–C6(cycloalkyl)methyl; (4) C3–C7(cycloalkyl-alkenyl)-C1–C5 alkyl, preferably C5–C6(cycloalkylalkenyl)methyl; (5) phenyl; (6) C7–C12 phenylalkyl, preferably benzyl; (7) C1–C5 alkyl substituted by C1–C5 alkyoxy, halogen, hydroxy or amino, with C1–C5 alkyl preferably substituted by one or two groups selected from methyl, methoxy, chlorine, bromine, fluorine, hydroxy or amino, with hydroxy, amino, chlorine, bromine or fluorine being most preferred; (8) C1–C5 alkyl substituted with nitro, alkyl or arylsufonyl, optionally protected where appropriate; (9) C1–C5 alkyl substituted with halogen, preferably trifluoromethyl; (10) aryl or aralkyl substituted by one or two groups of C1–C5 alkyl, C1–C5 alkoxy, halogen, hydroxy or amino, with one or two groups of methyl, methoxy, chlorine, bromine, fluorine, hydroxy or amino being preferred and hydroxy, amino, chlorine, bromine or fluorine being particularly preferred; (11) aryl or aralkyl substituted by one or two groups of halogen-substituted C1–C5 alkyl, especially trifluoromethyl; nitro; sulfonyl; or arylsulfonyl, in protected form where appropriate.

Preferred alkyloxycarbonyls include, but are not limited to, Boc, CBZ and Z.

By "peptidyl alkyloxycarbonyl" or "alkyloxycarbonyl peptidyl" herein is meant a peptidyl group linked to a alkyloxycarbonyl group. It is to be understood that the peptidyl group is linked to one of the nitrogens of the ethylenediamine or piperazine moieties, and the alkyloxycarbonyl group is linked to the peptidyl group. Thus, the free terminal functionality of a alkyloxycarbonyl peptidyl group is the R$_8$ group of Formula 5. As described above for acyl peptidyl, the order of the functionalities differs depending on whether it is the A group or the X group which is the alkyloxycarbonyl peptidyl; the group may be called a alkyloxycarbonyl peptidyl moiety when describing the A group and a peptidyl alkyloxycarbonyl moiety when describing the X group. Formula 5 shows a cysteine protease inhibitor with alkyloxycarbonyl peptidyl groups at both the A and X positions, wherein n is from 1 to 5, and AA is an amino acid:

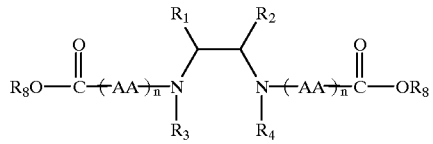

Formula 5

By "sulfonyl" herein is meant an —SO$_2$R$_9$ group, wherein S is sulfur, and O is oxygen. The sulfur atom is attached to one of the nitrogens of the ethylenediamine or piperazine moieties, and thus the sulfonyl group is also a sulfonamide because of the attachment to the nitrogen group. The R$_9$ moiety of the sulfonyl group may include, but is not limited to, an alkyl (forming alkylsulfonyl), a substituted alkyl, a cycloalkyl, a cycloalkylalkyl, a cycloalkylalkenyl, an aryl (forming arylsulfonyl, including heteroaryl (forming heteroarylsulfonyl)), or an aralkyl (forming arylalkylsulfonyl). In such an instance, alkyl is preferably of 1 to 5 carbon atoms, especially methyl. Substituted alkyl is preferably of 1 to 5 carbon atoms, bearing substitutions of alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, nitro, alkyl or arylsulfonyl, or halogen-substituted alkyl of 1 to 5 carbon atoms, particularly trifluoromethyl. Cycloalkyl preferably is of 3 to 7 carbon atoms, preferably cyclopentyl or cyclohexyl. Cycloalkylalkyl or cycloalkylalkenyl preferably is of 3 to 7 carbon atoms in the cycloalkyl, particularly 5 or 6 carbon atoms, and of 1 to 5 carbon atoms, particularly 1 carbon atom, in the alkyl or alkylene moieties thereof. Aryl preferably is phenyl, pentafluorophenyl or naphthyl. Aralkyl preferably is phenylalkyl of 7 to 12 carbon atoms, particularly benzyl and phenethyl. The optional substituents of an aryl or aralkyl moiety preferably are one or two groups alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, nitro, alkyl or arylsulfonyl, or halogen-substituted alkyl of 1 to 5 carbon atoms, particularly trifluoromethyl.

Particularly preferred $R_9$ moieties of the sulfonyl group include (1) C1–C5 alkyl, especially methyl; (2) C3–C7 cycloalkyl, preferably cyclopentyl or cyclolhexyl; (3) C3–C7(cycloalkyl)-C1–C5 alkyl, preferably C5–C6 (cycloalkyl)methyl; (4) C3–C7(cycloalkylalkenyl)-C1–C5 alkyl, preferably C5–C6(cycloalkylalkenyl)-methyl; (5) phenyl, preferably pentafluorophenyl or naphthyl; (6) C7–C12 phenylalkyl, preferably benzyl; (7) C1–C5 alkyl substituted by C1–C5 alkyoxy, halogen, hydroxy or amino, with C1–C5 alkyl preferably substituted by one or two groups selected from methyl, methoxy, chlorine, bromine, fluorine, hydroxy or amino, with hydroxy, amino, chlorine, bromine or fluorine being most preferred; (8) C1–C5 alkyl substituted with nitro, alkyl or arylsulfonyl, optionally protected where appropriate; (9) C1–C5 alkyl substituted with halogen, preferably trifluoromethyl; (10) aryl or aralkyl substituted by one or two groups of C1–C5 alkyl, C1–C5 alkoxy, halogen, hydroxy or amino, with one or two groups of methyl, methoxy, chlorine, bromine, fluorine, hydroxy or amino being preferred and hydroxy, amino, chlorine, bromine or fluorine being particularly preferred; (11) aryl or aralkyl substituted by one or two groups of halogen-substituted C1–C5 alkyl, especially trifluoromethyl; nitro; sulfonyl; or arylsulfonyl, in protected form where appropriate.

Especially preferred are phenyl, naphthyl, and benzyl.

By "peptidyl sulfonyl" or "sulfonyl peptidyl" herein is meant a peptidyl group linked to a sulfonyl group. As above, the peptidyl group is linked to one of the nitrogens of the ethylenediamine or piperazine moieties, and the sulfonyl group is linked to the peptidyl group. Thus, the free terminal functionality of a sulfonyl peptidyl group is the $R_9$ group. As described above for acyl peptidyl, the order of the functionalities differs depending on whether it is the A group or the X group which is the sulfonyl peptidyl; the group may be called a sulfonyl peptidyl moiety when describing the A group and a peptidyl sulfonyl moiety when describing the X group. Formula 6 shows a cysteine protease inhibitor with sulfonyl peptidyl groups at both the A and X positions, wherein n is from 1 to 5, and AA is an amino acid.

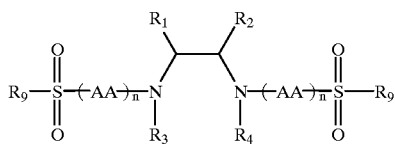

Formula 6

By "sulfamoyl" herein is meant an —$SO_2NR_{10}R_{11}$ group, wherein S is sulfur, O is oxygen, and N is nitrogen. The sulfur atom of the sulfone is linked to one of the nitrogens of the ethylenediamine or piperazine moieties. In some embodiments, the sulfamoyl comprises an —$SO_2NHR_{10}$ group, wherein H is hydrogen, and in other embodiments it comprises an —$SO_2NR_{10}R_{11}$, group.

Suitable —$NHR_{10}$ and —$NR_{10}R_{11}$ groups include, but are not limited to, an $NH_2$, or an NH-alkyl (forming alkylsulfamoyl), an NH-cycloalkyl, an NH-cycloalkylalkyl, an NH-aryl (forming arylsulfamoyl or heteroarylsulfamoyl), an NH-aralkyl, N-dialkyl (forming dialkylsulfamoyl) and N-alkylaralkyl. Cycloalkyl preferably is of 3 to 7 carbon atoms, preferably cyclopentyl or cyclohexyl. Cycloalkylalkyl preferably is of 3 to 7 carbon atoms in the cycloalkyl, particularly 5 or 6 carbon atoms, and of 1 to 5 carbon atoms, particularly 1 carbon atom, in the alkyl moieties thereof. Aryl preferably is phenyl or heteroaryl. Aralkyl preferably is phenylalkyl of 7 to 12 carbon atoms, particularly benzyl. The optional substituents of an aryl or aralkyl moiety preferably are one or two groups alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, nitro, alkyl or arylsulfonyl, or halogen-substituted alkyl of 1 to 5 carbon atoms, particularly trifluoromethyl. Especially preferred is when both $R_{10}$ and $R_{11}$ are methyl.

In a preferred embodiment, the $R_{10}$ and $R_{11}$ groups of a —$NR_{10}R_{11}$, are bonded together to form 5 or 6 membered alicyclic or heteroalicyclic ring moieties. Preferred are piperidine, morpholine, pyrrolidine, piperazine, or substituted piperazine.

By "peptidyl sulfamoyl" herein is meant a peptidyl group linked to a sulfamoyl group. As above, the peptidyl group is linked to one of the nitrogens of the ethylenediamine or piperazine moieties, and the sulfamoyl group is linked to the peptidyl group. Thus, the free terminal functionality of a sulfamoyl peptidyl group is the $R_{10}$ group. As described above for acyl peptidyl, the order of the functionalities differs depending on whether it is the A group or the X group which is the sulfamoyl peptidyl; the group may be called a sulfamoyl peptidyl moiety when describing the A group and a peptidyl sulfamoyl moiety when describing the X group. Formula 7 shows a cysteine protease inhibitor with a sulfamoyl peptidyl group at the A position and a peptidyl sulfamoyl at the X position, wherein n is from 1 to 10, and AA is an amino acid.

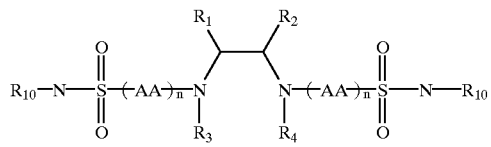

Formula 7

By "sutffinyl" herein is meant a —$SOR$, group, where S is sulfur, O is oxygen, and $R_9$ is a group as defined herein. The sulfur and oxygen atoms are double bonded together. The sulfur atom is attached to one of the nitrogens of the ethylenediamine or piperazine moieties. Preferred sulfinyl groups include alkylsulfinyl, dialkylaminosulfinyl, and arylsulfinyl, including heteroarylsulfinyl.

By "sulfinyl peptidyl" herein is meant a peptidyl group linked to a sulfinyl group. As above, the peptidyl group is linked to one of the nitrogens of the ethylenediamine or piperazine moieties, and the sulfinyl group is linked to the peptidyl group. Thus, the free terminal functionality of a sulfinyl peptidyl group is the $R_9$ moiety. As described above, the order of the functionalities differs depending on whether it is the A group or the X group which is the sulfinyl peptidyl;

the group may be called a sulfinyl peptidyl group when describing the A moiety, and a peptidyl sulfinyl when describing the X group. Formula 8 depicts a cysteine protease inhibitor with a sulfinyl peptidyl group at the A position and a peptidyl sulfinyl at the X position, wherein n is from 1 to 10, and M is an amino acid.

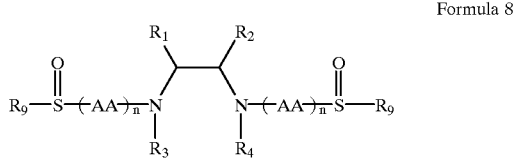

Formula 8

By "carbamoyl" herein is meant an —CONR$_{10}$R$_{11}$ group, H is hydrogen, C is carbon and O is oxygen. R$_{10}$ and R$_{11}$ are defined as above.

By "carbamoyl peptidyl" herein is meant a carbamoyl group linked to a peptidyl group. The term "carbamoyl peptidyl" includes both "carbamoyl peptidyl" and "peptidyl carbamoyl". That is, in one embodiment the carbamoyl is attached to one of the nitrogens of the ethylenediamine or piperazine moieties, and the peptidyl moiety is attached to the carbamoyl. In this embodiment, the terminal functionality is the peptidyl. Alternatively, the peptidyl moiety may be attached to the ethylenediamine or piperazine moiety and the carbamoyl moiety attached to the peptidyl. In this embodiment, the terminal functionality is the carbamoyl. These two embodiments are depicted below in Formulas 9 (carbamoyl peptidyl) and 10 (peptidyl carbamoyl) as comprising the X moiety. It should be understood that Formulas 9 and 10 do not accurately reflect the structure where one of the amino acids is a proline.

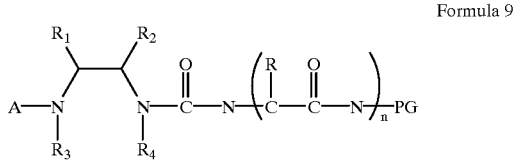

Formula 9

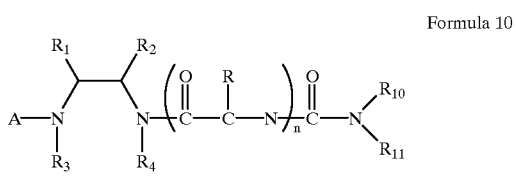

Formula 10

The two N-substituents of the invention are linked via an ethylenediamine or substituted ethylenediamine group. By "ethylenediamine group" herein is meant a —NH—CH$_2$—CH$_2$—NH— group, wherein N is nitrogen, C is carbon, and H is hydrogen. The two N-substituents, depicted herein as "A" and "X", are each linked to one of the nitrogens of the ethylenediamine. "Linked" herein means a covalent attachment. Thus, in one embodiment, the cysteine protease inhibitors of the invention have the structure shown in Formula 11:

Formula 11

It should be understood that the depiction of the ethylenediamine group in Formula 11 and others as having a certain conformation is merely pictorial. Thus, Formula 11, and the other ethylenediamine moieties may be depicted as shown in Formula 11A:

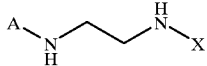

Formula 11A

In a preferred embodiment, the N-substituents are linked via a substituted ethylenediamine moiety. By "substituted ethylenediamine" herein is meant an ethylenediamine group which has one or more of the hydrogen atoms replaced by a substituent group. It should be understood that the substituted ethylenediamine does not contain a peptide bond; that is, neither the R$_1$ or the R$_2$ positions may be a carbonyl.

In a preferred embodiment, the ethylenediamine is substituted with an R group on either one of the carbons of the ethylene. Thus, as shown in Formula 12, R$_1$ and R$_2$ are either hydrogen or an amino acid side chain. It is to be understood that only one of R$_1$ and R$_2$ is an amino acid side, and the other one of R$_1$ and R$_2$ is hydrogen. Preferably, R$_2$ is an amino acid side chain and R$_1$ is hydrogen.

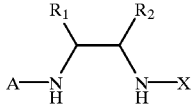

Formula 12

As will be appreciated by those in the art, there are a large number of possible A and X combinations which can be made. Any A group may be combined with any X group. In one embodiment, the A and the X group are the same; for example, the A group may be a sulfonyl peptidyl group and the X group may be a peptidyl sulfonyl group. However, it should be understood that even if both the A and X groups are sulfonyls, for example, the R$_9$ groups of each sulfonyl need not be the same. This is similarly true for the other embodiments. In an alternative embodiment, the A group and the X group are different.

When R$_2$ is an amino acid side chain and R. is hydrogen, preferred A and X group combinations are depicted in Table 2:

TABLE 2

| Preferred A group | Preferred X group |
|---|---|
| PAEBG-amino acid* | sulfonyl |
| PAEBG-peptidyl | sulfonyl |
| alkyloxycarbonyl peptidyl | sulfonyl |
| sulfonyl peptidyl | sulfonyl |
| carbamoyl peptidyl | sulfonyl |
| sulfamoyl peptidyl | sulfonyl |
| acyl peptidyl | sulfonyl |
| sulfinyl peptidyl | sulfonyl |
| PG-amino acid | peptidyl-PAEBG |
| alkyloxycarbonyl peptidyl | peptidyl-PAEBG |

TABLE 2-continued

| Preferred A group | Preferred X group |
| --- | --- |
| sulfonyl peptidyl | peptidyl-PAEBG |
| carbamoyl peptidyl | peptidyl-PAEBG |
| sulfamoyl peptidyl | peptidyl-PAEBG |
| acyl peptidyl | peptidyl-PAEBG |
| sulfinyl peptidyl | peptidyl-PAEBG |

*PAEBG = peptide amino end blocking group; or PG

When $R_1$ is an amino acid side chain and $R_2$ is hydrogen, preferred A and X group combinations are depicted in Table 3:

TABLE 3

| Preferred A group | Preferred X group |
| --- | --- |
| sulfonyl | peptidyl-PAEBG |
| sulfonyl | peptidyl alkyloxycarbonyl |
| sulfonyl | peptidyl sulfonyl |
| sulfonyl | peptidyl carbamoyl |
| sulfonyl | peptidyl sulfamoyl |
| sulfonyl | peptidyl acyl |
| sulfonyl | peptidyl sulfinyl |
| PAEBG peptidyl | amino acid-PG |
| PAEBG peptidyl | peptidyl alkyloxycarbonyl |
| PAEBG peptidyl | peptidyl sulfonyl |
| PAEBG peptidyl | peptidyl carbamoyl |
| PAEBG peptidyl | peptidyl sulfamoyl |
| PAEBG peptidyl | peptidyl acyl |
| PAEBG peptidyl | peptidyl sulfinyl |

The preferred A and X groups listed in Tables 2 and 3 apply to the piperazine moieties described below as well.

In a preferred embodiment, the ethylenediamine is substituted on the nitrogens of the ethylenediamine, as shown in Formula 1. In this embodiment, $R_3$ and $R_4$ are either both hydrogen or are bonded together to form ethylene or substituted ethylene. By "ethylene" or "ethylene group" herein is meant a (—CH$_2$CH$_2$—) group, i.e. a saturated carbon—carbon bond, serving to connect two sp$^3$-hybridized carbon atoms; that is, the two carbons of the ethylene group are not double bonded together. By "substituted ethylene" herein is meant an ethylene group which has one of the hydrogens of the ethylene replaced by a substitutent group, i.e. a (—CH$_2$CHR—) group, where R is $R_5$ or $R_6$, as depicted below. When $R_3$ and $R_4$ form ethylene or substituted ethylene, the substituted ethylenediamine moiety is a piperazine moiety, which in turn may be substituted or unsubstituted. That is, the carbon atoms of the piperazine moiety may have no substituent groups, i.e. only hydrogen, as shown in Formula 13, an $R_1$ or $R_2$ group as shown in Formula 14, an $R_5$ or $R_6$ group as shown in Formula 15, or both an $R_1$ and $R_6$ or an $R_2$ and $R_5$ group (Formulas 16 and 17).

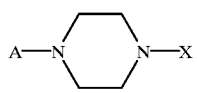

Formula 13

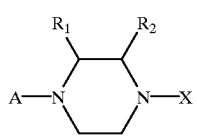

Formula 14

In a preferred embodiment, $R_2$ is an amino acid side chain and $R_1$ is hydrogen.

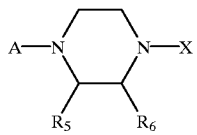

Formula 15

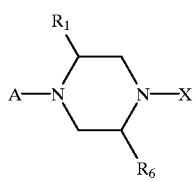

Formula 16

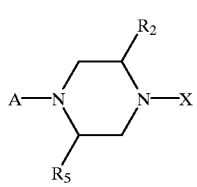

Formula 17

In Formulas 16 and 17, it is to be understood that the two substitution groups of the six-membered heterocyclic ring of piperazine are in para position to each other; that is, there may be substitution groups at $R_1$ and $R_6$ or $R_2$ and $R_5$. $R_1$, $R_2$, $R_5$ and $R_6$ are independently hydrogen or an amino acid side chain.

In a preferred embodiment, the cysteine protease inhibitors of the present invention have a peptidyl moiety as the "A" group and a sulfonyl moiety as the "X" group, and an $R_2$ group, and thus have the general formula shown in Formula 18 and Formula 18A. As will be appreciated by those in the art, Formula 18 does not accurately represent the structure when one or more of the amino acids of the peptidyl group are proline.

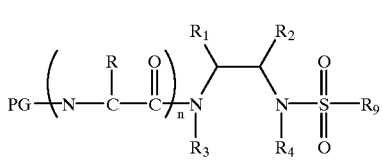

Formula 18

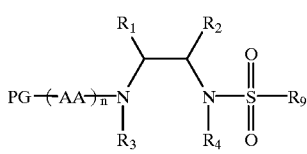

Formula 18A

When the cysteine protease inhibitors have the formula depicted in Formulas 18 and 18A, preferably the inhibitors have an $R_2$ group. In addition, preferably n=1 or 2. In one preferred embodiment, $R_3$ and $R_4$ are hydrogen; in an alternate preferred embodiment, $R_3$ and $R_4$ together form unsubstituted ethylene, to form a piperazine which has a single substituent group at $R_2$.

In a preferred embodiment, the cysteine protease inhibitors have a sulfonyl peptidyl moiety as the "A" group and a sulfonyl moiety as the "X" group, and an $R_2$ group, and thus have the general formula shown in Formula 19 and 19A (where the amino acid is not proline):

Formula 19

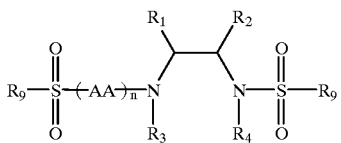

Formula 19A

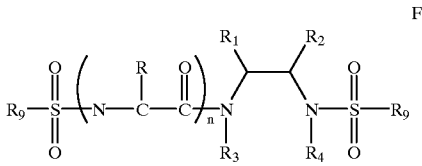

When the cysteine protease inhibitors have the formula depicted in Formula 19 and 19A, preferably the inhibitors have an $R_2$ group. In addition, preferably n=1 or 2. As above, this structure is not accurate when one or more of the amino acids of the peptidyl are proline. In one embodiment, $R_3$ and $R_4$ are hydrogen; in a preferred embodiment, $R_3$ and $R_4$ together form unsubstituted ethylene, to form a piperazine which has a single substituent group at $R_2$.

In a preferred embodiment, the cysteine protease inhibitors of the invention have an acyl peptidyl moiety as the "A" group and a sulfonyl moiety as the "X" group as depicted as Formula 20 and Formula 20A (when the amino acid is not proline):

Formula 20

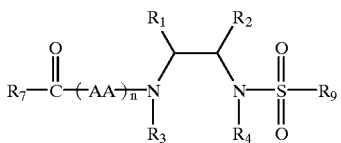

Formula 20A

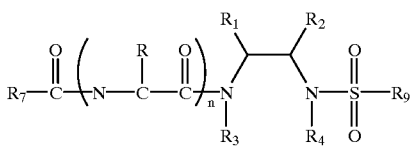

When the cysteine protease inhibitors have the formula depicted in Formula 20 and 20A, preferably the inhibitors have a $R_2$ group. Preferably n=1 or 2. In one embodiment, $R_3$ and $R_4$ are hydrogen; in an alternative embodiment $R_3$ and $R_4$ together form unsubstituted ethylene, to form a piperazine which has a single substituent group at $R_2$.

Thus, preferred embodiments include compounds of Formula I:

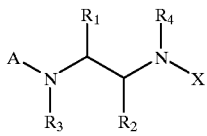

I in which:

A and X are independently $R_{13}$—$X_1$—, wherein $R_{13}$ is hydrogen, alkyloxycarbonylalkanoyl, alkyloxycarbonyl, alkanoyl (optionally substituted with a radical selected from carboxy, alkyloxycarbonyl and heterocycloalkylalkanoylamino), cycloalkylcarbonyl, heterocycloalkylcarbonyl (optionally substituted with a radical selected from hydroxy, alkyl, heterocycloalkyl, alkanoyl, alkyloxycarbonyl, arylalkyloxycarbonyl and heterocycloalkylcarbonyl), arylalkyloxycarbonyl, carbamoyl, alkylcarbamoyl, dialkylcarbamoyl, arylcarbamoyl, arylalkylcarbamoyl, arylalkanoyl, aroyl, alkylsulfonyl, arylsulfonyl, arylalkylsulfonyl, alkylsulfamoyl, dialkylsulfamoyl, arylsulfamoyl, heteroarylsulfamoyl, alkylsulfinyl, dialkylaminosulfinyl or arylsulfinyl and $X_1$ is a bond or a divalent radical of Formulae (a) or (b):

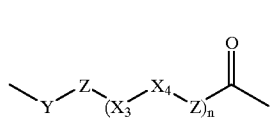

(a)

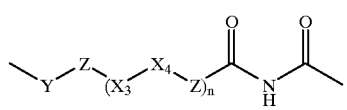

(b)

in which n is 0 to 9; $X_3$-$X_4$ represents a linkage selected from —C(O)$NR_{14}$—, —$CH_2NR_{14}$—, —C(O)$CH_2$— and —$NR_{14}$C(O)—; Y is —CH($R_{14}$)— or —$NR_{14}$—; and Z is —($CH_2$)$_2$—, —C($R_{15}$)($R_{16}$)— or —N($R_{16}$)—; wherein $R_{14}$ is hydrogen or as defined below, $R_{15}$ is hydrogen or methyl and each $R_{16}$ is independently hydrogen, alkyl (optionally substituted with a radical selected from hydroxy, alkyloxy, amino, alkylamino, dialkylamino, uriedo, alkyluriedo, mercapto, alkylthio, carboxy, carbamoyl, alkylcarbamoyl, dialkylcarbamoyl, alkylsulfinyl, alkylsulfonyl, guanidino, —P(O)(O$R_{12}$)$_2$, —OP(O)(O$R_{12}$)$_2$ and —OP(O)($R_{12}$)$_2$, wherein each $R_{12}$ is independently hydrogen or alkyl, or a protected derivative thereof), cycloalkyl, cycloalkylalkyl, a group selected from aryl and arylalkyl (which group is optionally substituted at its aryl ring with one to three radicals selected from hydroxy, amino, guanidino, halo, optionally halo-substituted alkyl, alkyloxy and aryl, or a protected derivative thereof) or together with an adjacent $R_{14}$ forms a divalent radical selected from ($C_{3-4}$)methylene and 1,2-phenylenedimethylene (which radical is optionally substituted with hydroxy, or a protected derivative thereof, or oxo), with the proviso X and A are not both hydrogen;

$R_1$ and $R_2$ are both hydrogen or one of $R_1$ or $R_2$ is cyano, carboxy, alkyloxycarbonyl, alkanoyl, carbamoyl, alkylcarbamoyl, dialkylcarbamoyl, alkyloxy(alkyl) carbamoyl, aminoalkylcarbamoyl, $R_{16}$, as defined above, or $R_{13}$—$X_2$—, wherein $R_{13}$ is as defined above and $X_2$ is a divalent radical of Formulae (a) or (b), as defined above; and $R_3$ and $R_4$ together form optionally substituted ethylene or are independently $R_{14}$, as defined above; and the pharmaceutically acceptable salts, individual isomers and mixtures of isomers thereof.

Preferred Formula I compounds include compounds wherein A is $R_{13}$—$X_1$—, wherein $R_{13}$ is hydrogen, alkyloxycarbonylalkanoyl of overall 3 to 10 carbon atoms, $(C_{1-9})$alkoxycarbonyl, $(C_{2-10})$alkanoyl (optionally substituted with a radical selected from carboxy, $(C_{1-9})$alkyloxycarbonyl and hetero$(C_{4-8})$cycloalkyl$(C_{2-10})$ alkanoylamino), $(C_{4-8})$cycloalkylcarbonyl, hetero$(C_{4-8})$ cycloalkylcarbonyl (optionally substituted with a radical selected from hydroxy, $(C_{1-5})$alkyl, hetero$(C_{4-8})$cycloalkyl, $(C_{1-5})$alkanoyl, $(C_{1-5})$alkyloxycarbonyl, $(C_{6-10})$aryl$(C_{1-5})$ alkyloxycarbonyl and hetero$(C_{4-8})$cycloalkylcarbonyl), $(C_{6-10})$aryl$(C_{1-5})$alkyloxycarbonyl, carbamoyl, $(C_{1-5})$ alkylcarbamoyl, di$(C_{1-5})$alkylcarbamoyl, $(C_{6-10})$ arylcarbamoyl, $(C_{6-10})$aryl$(C_{1-5})$alkylcarbamoyl, $(C_{6-10})$aryl $(C_{1-5})$alkanoyl, $(C_{7-11})$aroyl, $(C_{1-5})$alkylsulfonyl, di$(C_{1-5})$ alkylsulfamoyl, $(C_{6-10})$arylsulfonyl, $(C_{6-10})$aryl$(C_{1-5})$ alkylsulfonyl or hetero$(C_{4-8})$arylsulfonyl; and $X_1$ is a divalent radical of Formula (a), wherein n is 0 to 5; $X_1$–$X_2$ represents a linkage selected from —C(O)NR$_{14}$—; Y is —N(R$_{14}$)—; Z is —CH(R$_{16}$)—; R$_{14}$ is hydrogen or as defined below; and $R^{16}$ is $(C_{3-7})$cycloalkyl, $(C_{3-7})$cycloalkyl $(C_{1-5})$alkyl, pyridyl, thienyl, furyl, imidazolyl, indolyl, pyridyl$(C_{1-6})$alkyl, thienyl$(C_{1-6})$alkyl, furyl$(C_{1-6})$alkyl, imidazolyl$(C_{1-6})$alkyl, indolyl$(C_{1-6})$alkyl, $(C_{1-5})$alkyl (optionally substituted with a radical selected from mercapto, carboxy, amino, methylthio, methylsulfonyl, carbamoyl, dimethylcarbamoyl, guanidino and hydroxy, or a protected derivative thereof), a group selected from phenyl, naphthyl, phenyl$(C_{1-6})$alkyl, naphthyl$(C_{1-6})$alkyl, (which group is optionally substituted at its aryl ring with one to three radicals selected from amino, hydroxy, chloro, bromo, fluoro, iodo, methyl, trifluoromethyl, methoxy and phenyl, or a protected derivative thereof) or together with an adjacent $R_{14}$ forms a divalent radical selected from $(C_{3-4})$ methylene and 1,2-phenylenedimethylene (which radical is optionally substituted with hydroxy, or a protected derivative thereof, or oxo); X is —S(O)$_2$R$_9$, wherein R$_9$ is $(C_{1-5})$ alkyl (optionally substituted with one or two radicals selected from amino, chloro, bromo, fluoro, hydroxy and methoxy, or a protected derivative thereof), perhalo$(C_{1-5})$ alkylsulfonyl, $(C_{3-7})$cycloalkyl, $(C_{3-7})$cycloalkyl$(C_{1-5})$alkyl or a group selected from phenyl, pentafluorophenyl, naphthyl and phenyl$(C_{1-6})$alkyl (which group is optionally substituted at its aryl ring with one to two radicals selected from amino, chloro, bromo, fluoro, hydroxy, methoxy and optionally halo-substituted methyl, or a protected derivative thereof);

$R_1$ is hydrogen and $R_2$ is $R_{16}$, as defined above; and $R_3$ and $R_4$ are each hydrogen or together form optionally substituted ethylene.

Further preferred compounds of this embodiment include n is 0 to 2; $R_2$ is $R_{16}$, as defined below; $R_3$ and $R_4$ together form optionally substituted ethylene; $R_{13}$ is hydrogen, $(C_{4-8})$alkoxycarbonyl, $(C_{2-6})$alkanoyl (optionally substituted with a radical selected from carboxy, $(C_{1-5})$ alkyloxycarbonyl and hetero$(C_{4-8})$cycloalkyl-$(C_{4-6})$ alkanoylamino), —C(O)NR$_{10}$R$_{11}$, wherein R$_{10}$ and R$_{11}$ together form aza$(C_{2-6})$methylene, oxa$(C_{2-6})$methylene or $(C_{3-7})$methylene, $(C_{4-8})$cycloalkylcarbonyl, benzyloxycarbonyl, acetyl, benzoyl or dimethylsulfamoyl; $R_{16}$ is $(C_{5-6})$cycloalkyl, $(C_{5-6})$cycloalkylmethyl, 3-pyridyl, 2-thienyl, 2-furyl, 4-imidazolyl, 3-indolyl, 3-pyridylmethyl, 2-thienylmethyl, 2-furylmethyl, 4-imidazolylmethyl, 3-indolylmethyl, methoxy, acetoxy, $(C_{1-5})$alkyl (optionally substituted with a radical selected from mercapto, carboxy, amino, methylthio, methylsulfonyl, carbamoyl, dimethylcarbamoyl, guanidino and hydroxy, or a protected derivative thereoftl, a group selected from phenyl, 1-naphthyl, 2-naphthyl, benzyl, 1-naphthylmethyl, 2-naphthylmethyl and 2-phenylethyl (which group is optionally substituted at its aryl ring with one radical selected from hydroxy, amino, chloro, bromo and fluoro, or a protected form thereof) or together with an adjacent $R_{14}$ forms a divalent radical selected from $(C_{3-4})$methylene and 1,2-phenylenedimethylene (which radical is optionally substituted with hydroxy, or a protected derivative thereof, or oxo); and $R_9$ is $(C_{1-5})$alkyl (optionally substituted with one or two radicals selected from amino, chloro, bromo, fluoro and hydroxy, or a protected derivative thereof), perfluoro $(C_{1-5})$alkyl, $(C_{5-6})$cycloalkyl, $(C_{5-6})$cycloalkylmethyl or a group selected from phenyl, naphthyl and benzyl (which group is optionally substituted with one radical selected from amino hydroxy, chloro, bromo or fluoro, or a protected derivative thereof).

Particularly preferred compounds of this embodiment include n is 0 to 1; $R_2$ is butyl, 2-phenylethyl, 2-methylsulfonylethyl, 2-tert-butoxycarbonylethyl, 2-tert-butoxycarbonylmethyl, 4-tert-butoxycarbonylaminobutyl, 4-benzoylaminobutyl or benzyloxymethyl; $R_{13}$ is hydrogen, tert-butoxycarbonyl, benzyloxycarbonyl, acetyl, 3-carboxypropionyl, 3-methoxycarbonylpropionyl, biotinylaminohexanoyl, phenylacetyl, benzoyl, dimethylsulfamoyl, benzylsulfonyl, 1-piperizinylcarbonyl, 4-methyl-1-piperazinylcarbonyl or 4-morpholinylcarbonyl; $R_{16}$ is 3-pyridylmethyl, 2-thienylmethyl, 2-furylmethyl, 4-imidazolylmethyl, 3-indolylmethyl, $(C_{1-5})$alkyl (optionally substituted with a radical selected from mercapto, carboxy, amino, methylthio, methylsulfonyl, carbamoyl, dimethylcarbamoyl, guanidino and hydroxy, or a protected derivative thereof), a group selected from benzyl, 1-naphthylmethyl, 2-naphthylmethyl and 2-phenylethyl (which group is optionally substituted at its aryl ring with one radical selected from hydroxy, amino, chloro, bromo and fluoro, or a protected form thereof) or together with an adjacent $R_3$ or $R_{13}$ forms a divalent radical selected from $(C_{3-4})$methylene and 1,2-phenylenedimethylene (which radical is optionally substituted with hydroxy, or a protected derivative thereof, or oxo); and $R_9$ is methyl, trifluoromethyl, optionally substituted phenyl, 2-naphthyl or 2-phenylethyl.

Especially preferred embodiments include n is 0; $R_2$ is butyl, 2-phenylethyl or 2-methylsulfonylethyl; $R_{13}$ is hydrogen, tert-butxoycarbonyl, benzyloxycarbonyl, biotinylaminohexanoyl, benzoyl, 1-piperiziny-carbonyl, 4-methyl-1-piperazinylcarbonyl or 4-morpholinylcarbonyl; $R_{16}$ is $(C_{1-5})$alkyl, optionally substituted benzyl, 1-naphthylmethyl, 2-naphthylmethyl, 3-pyridinylmethyl or 2-methylsulfonylethyl; and $R_9$ is phenyl, 1-naphthyl or 2-phenylethyl.

As are depicted in FIG. 1, preferred inhibitors of the invention include (abbreviation first): Mu-Phe-retro-(D,L)-PheSO$_2$Ph: 2-benzyl-4-(morpholinecarbonylphenylalanyl)-1-phenylsulfonylethylenediamine; Mu-Phe-retro-(D,L)-LeuSO$_2$Ph: 2-isobutyl-4-(morpholinecarbonylphenylalanyl)-1-phenylsulfonylethylenediamine; Mu-Tyr-retro-(D,L)-LeuSO$_2$Ph: 2-isobutyl-4-(morpholinecarbonyltyrosyl)-1-phenylsulfonylethylenediamine; Mu-Phe-retro-(D,L)

HphSO₂Ph: 4-(morpholinecarbonylphenylalanyl)-2-phenethyl-1-phenylsulfonylethylenediamine; Mu-Tyr-retro-(D,L)Hph-SO₂Ph: 4-(morpholinecarbonyltyrosyl)-2-phenethyl-1-phenylsulfonylethylenediamine; Mu-Tyr-retro-(D,L)-NleSO₂Ph: 2-butyl-4-(morpholinecarbonyltyrosyl)-1-phenylsulfonylethylenediamine; Mu-Np2-retro-(D,L)-NleSO₂Ph: 2-butyl-4-(morpholinecarbonyl-2-naphthylalanyl)-1-phenylsulfonylethylenediamine; Boc-Np2-retro-(D,L)-NleSO₂Ph: 4-(tert-butoxycarbonyl-2-naphthylalanyl)-2-butyl-1-phenylsulfonylethylenediamine; Piv-Np2-retro-(D,L)-NleSO₂Ph: 2-butyl-4-(pivaloyl-2-naphthylalanyl)-1-phenylsulfonylethylenediamine; Mu-Np2-retro-(D,L)-HphSO₂Ph: 4-(morpholinecarbonyl-2-naphthylalanyl)-2-phenethyl-1-phenylsulfonylethylenediamine; Boc-Np2-retro-(D,L)-HphSO₂Ph: 4-(tert-butoxycarbonyl-2-naphthylalanyl)-2-phenethyl-1-phenylsulfonylethylenediamine; Mu-Phe-pip-retro-(D,L)-LeuSO₂Ph: 2-isobutyl-4-(morpholinecarbonylphenylalanyl)-1-phenylsulfonyl-1,4-piperazine; Mu-Phe-pip-retro-(D,L)-HphSO₂Ph: 4-(morpholinecarbonylphenylalanyl)-2-phenethyl-1-phenylsulfonyl-1,4-piperazine; Z-Np2-retro-(D,L)-NleSO₂2Np: 4-(benzyloxycarbonyl-2-naphthylalanyl)-2-butyl-1-(2-naphthylsulfonyl)-ethylenediamine; Bzac-Np2-retro-(D,L)-NleSO₂2Np: 4-(benzylaminocarbonyl-2-naphthylalanyl)-2-butyl-1-(2-naphthylsulfonyl)ethylenediamine; BzISO₂-Np2-retro-(D,L)-NleSO₂2Np: 4-(benzylsulfonyl-2-naphthylalanyl)-2-butyl-1-(2-naphthylsulfonyl)-ethylenediamine; Mu-Np2-pip-retro-(D,L)-NleSO₂2Np: 2-butyl-4-(morpholinecarbonyl-2-naphthylalanyl)-1-(2-naphthylsulfonyl)-1,4-piperazine; MeOSuc-Np2-pip-retro-(D,L)-NleSO₂2Np: 2-butyl-4-(methoxycarbonylpropionyl-2-naphthylalanyl)-1-(2-naphthylsulfonyl)-1,4-piperazine; Z-Np2-pip-retro-(D,L)-NleSO₂2Np: 4-(benzyloxycarbonyl-2-naphthylalanyl)-2-butyl-1-(2-naphthylsulfonyl)-1,4-piperazine; Bzac-Np2-pip-retro-(D,L)-NleSO₂2Np: 4-(benzylaminocarbonyl-2-naphthylalanyl)-2-butyl-1-(2-naphthylsulfonyl)-1,4-piperazine; BzISO₂-Np2-pip-retro-(D,L)-NleSO₂2Np: 4-(benzylsulfonyl-2-naphthylalanyl)-2-butyl-1-(2-naphthylsulfonyl)-1,4-piperazine; PhSO₂-Np2-pip-retro-(D,L)-NleSO₂2Np: 2-butyl-1-(2-naphthylsulfonyl)-4-(phenylsulfonyl-2-naphthylalanyl)-1,4-piperazine; tBac-Np2-pip-retro-(D,L)-NleSO₂2Np: 2-butyl-4-(tert-butylaminocarbonyl-2-naphthylalanyl)-1-(2-naphthylsulfonyl)-1,4-piperazine; Mu-Phe-pip-GlySO₂Ph: 4-(morpholine-carbonylphenylalanyl)-1-phenylsulfonyl-1,4-piperazine; Z-Np2-pip-GlySO₂2Np: 4-(benzyloxycarbonyl-2-naphthylalanyl)-1-(2-naphthylsulfonyl)-1,4-piperazine; Phac-Np2-pip-GlySO₂2Np: 1-(2-naphthylsulfonyl)-4-(phenylacetyl-2-naphthylalanyl)-1,4-piperazine; t-Buac-Np2-pip-GlySO₂2Np: 4-(tert-butylacetyl-2-naphthylalanyl)-1-(2-naphthylsulfonyl)-1,4-piperazine; Boc-Np2-pip-GlySO₂2Np: 4-(tert-butoxycarbonyl-2-naphthylalanyl)-1-(2-naphthylsulfonyl)-1,4-piperazine; Z-Np2-pip-GlySO₂Bzl: 4-(benzyloxycarbonyl-2-naphthylalanyl)-1-benzylsulfonyl-1,4-piperazine; and Phac-Np2-pip-GlySO₂Bzl: 1-benzylsulfonyl-4-(phenylacetyl-2-naphthylalanyl)-1,4-piperazine.

Additionally preferred compounds (not pictured in FIG. 1) include: Z-leu-pip-GlySO₂Np2: 4-(benzyloxylcarbonylleucyl)-1-(2-naphthylsulfonyl)-1,4-piperazine; Z-ala-pip-glySO₂Np2: 4-(benzyloxycarbonylalanyl)-1-(2-naphthylsulfonyl)-1,4-piperazine; Np1SO₂-leu-pip-GlySO₂Np2: 4-(1-naphthylsulfonylleucyl)-1-(2-naphthylsulfonyl)-1,4-piperazine; Np2SO₂-leu-pip-GlySO₂Np2: 4-(2-naphthylsulfonylleucyl)-1-(2-naphthylsulfonyl)-1,4-piperazine; PP-leu-pip-GlySO₂Np2: 4-[4-(1-piperidyl)-1-piperidoylleucyl]-1-(2-naphthylsulfonyl)-1,4-piperazine; Np2-arg-pip-GlyZ: 4-(2-naphthylsulfonylarginyl)-1-benyloxycarbonyl-1,4-piperazine; Np2-tyr-Z-le-pip-GlySO₂Np2: 4-(2-naphthylsulfonyltyrosyl)-1-(2-naphthylsulfonyl)-1,4-piperazine; MP-leu-pip-retro-(D,L)-HphSO₂Np2: 4-(4-methylpiperazinoylleucyl)-1-(2-naphthylsulfonyl)-2-(2-phenylethyl)-1,4-piperazine; iBoc-nap2-pip-Z-le-pip-GlySO₂Np2: 4-[isobutoxycarbonyl-(2-naphthyl)alanyl]-1-(2-naphthylsulfonyl)-1,4-piperazine; PM-nap2-pip-GlySO₂Np2: 4-[4-piperidylmethoxycarbonyl-(2-naphthyl)alanyl]-1-(2-naphthylsulfonyl)-1,4-piperazine; BI-nap2-pip-SO₂Np2: 4-[6-benzimidazoloyl-(2-naphthyl)alanyl]-1-(2-naphthylsulfonyl)-1,4-piperazine; and MP-leu-pip-retro-(D,L)-NleSO₂Np2: 2-butyl-4-(4-methylpiperazinoylleucyl)-1-(2-naphthylsulfonyl)-1,4-piperazine.

Additional preferred compounds of the invention include: tBoc-leu-pip-(D,L)-(MeO)(Me)NCOGlySO₂Np2: 4-(tert-butoxylcarbonylleucyl)-3-(N-methoxy)(N-methyl)carbamoyl-1-(2-naphthylsulfonyl)-1,4-piperazine; Z-leu-pip-retro-(D,L)-MeOCOGlySO₂Np2: 4-(benzyloxycarbonylleucyl)-2-methoxycarbonyl-1-(2-naphthylsulfonyl)-1,4-piperazine; Z-leu-pip-retro-(D,L)-HOCOGlySO₂Np2: 4-(benzyloxycarbonylleucyl)-2-carboxy-1-(2-naphthylsulfonyl)-1,4-piperazine; Z-leu-pip-retrot-D,L)-EtACOGlySO₂Np2: 4t-benzyloxycarbonylleucyl)-2-ethylcarbamoyl-1-(2-naphthylsulfonyl)-1,4-piperazine; and Z-leu-pip-retro-(D,L)-AEtACOGlySO₂Np2: 4-(benzyloxycarbonylleucyl)-2-(2-aminoethylcarbamoyl)-1-(2-naphthylsulfonyl)-1,4-piperazine.

In some embodiments, the stereochemistry of the amino acid side chains at positions $R_1$, $R_2$, $R_5$ and $R_6$ is important. That is, the amino acid side chains may be in either the (D) or (R) configuration, or the (L) or (S)configuration.

In a preferred embodiment, the dissociation constant for inhibition of a protease with the inhibitor, generally referred to by those in the art as $K_I$, is at most about 100 μM. By the term "binding constant" or "dissociation constant" or grammatical equivalents herein is meant the equilibrium dissociation constant for the reversible association of inhibitor with enzyme. The dissociation constants are defined and determined as below.

The determination of dissociation constants is known in the art. For example, for reversible inhibition reactions such as those of the present invention, the reaction scheme is as follows:

Equation 1

The enzyme and the inhibitor combine to give an enzyme-inhibitor complex, E·I. This step is assumed to be rapid and reversible, with no chemical changes taking place; the enzyme and the inhibitor are held together by non-covalent forces. In this reaction, $k_1$ is the second order rate constant for the formation of the E·I reversible complex. $k_2$ is the first order rate constant for the disassociation of the reversible E·I complex. In this reaction, $K_I = k_2/k_1$.

The measurement of the equilibrium constant $K_I$ proceeds according to techniques well known in the art, as described in the examples. For example, assays generally use synthetic chromogenic or fluorogenic substrates.

The respective $K_I$ values may be estimated using the Dixon plot as described by Irwin Segel in Enzyme Kinetics:

Behavior and analysis of rapid equilibrium and steady-state enzyme systems, 1975, Wiley-lnterscience Publication, John Wiley & Sons, New York, or for competitive binding inhibitors from the following calculation:

$$1-(v_i/v_o)=[I]/([I]+K_I(1+([S]/K_M)))$$  Equation 2 wherein v$_o$ is the rate of substrate hydrolysis in the absence of inhibitor, and v$_i$ is the rate in the presence of competitive inhibitor.

It is to be understood that dissociation constants are a particularly useful way of quantifying the efficiency of an enzyme with a particular substrate or inhibitor, and are frequently used in the art as such. If an inhibitor exhibits a very low K$_I$, it is an efficient inhibitor. Accordingly, the cysteine protease inhibitors of the present invention have dissociation constants, K$_I$, of at most about 100 μM. Preferred embodiments have inhibitors that exhibit dissociation constants of at most about 10 μM, at most about 1 μM, with the most preferred embodiments having dissociation constants of at most about 100 nM.

In the preferred embodiment, the cysteine protease inhibitors are chiral. By the term "chiral" or grammatical equivalents herein is meant a compound that exhibits asymmetry. That is, the chiral compound is not identical with its mirror image. Thus in the preferred embodiment, the compounds of the present invention are pure diasteromers. Chiral compounds, and particularly chiral cysteine protease inhibitors, are useful in the present invention because biological systems, and enzymes in particular, are stereospecific, preferring the (S) or L-form of amino acids. Thus in the preferred embodiment, the A and X groups of the cysteine protease inhibitors of the present invention will have amino acid side chains in the (S) or L-configuration, although some inhibitors may utilize amino acid side chains in the (R) or D-configuration.

In alternative embodiments, the compositions of the present invention are not pure epimers, but are mixtures that contain both epimers.

The synthesis of the cysteine protease inhibitors of the present invention proceeds as follows.

Synthesis of cysteine protease inhibitors with A and X groups linked via substituted ethylenediamine linkages is depicted generally in FIGS. 2 and 3. For unsubstituted ethylenediamine linkages, R$_1$ and R$_2$ are hydrogen. FIG. 3 depicts the R$_1$ synthesis, FIG. 4 depicts the R$_2$ synthesis. Both schemes are depicted using a peptidyl group as a representative "A" moiety and a sulfonyl group as a representative "X" moiety; however, those in the art will appreciate that these schemes may be used to synthesize cysteine protease inhibitors with other A and X groups.

Synthesis of cysteine protease inhibitors with R$_2$ and R. substituted piperazine as the linkage is depicted generally in FIG. 4. For unsubstituted piperazine, R$_2$ and R$_5$ are hydrogen. As above, a peptidyl group is shown as a representative "A" group and a sulfonyl group as the representative "X" group; as above, those in the art will appreciate that this scheme may be used to synthesize cysteine protease inhibitors with other A and X groups.

Synthesis of cysteine protease inhibitors with R$_1$ and R$_6$ substituted piperazine as the linkage is depicted generally in FIG. 5. For unsubstituted piperazine, R$_1$ and R$_6$ are hydrogen. As above, a peptidyl group is shown as a representative "A" group and a sulfonyl group as the representative "X" group; as above, those in the art will appreciate that this scheme may be used to synthesize cysteine protease inhibitors with other A and X groups.

Intermediates useful for the preparation of compounds of the invention in which R$_1$ or R$_2$ is carboxy, carbamoyl, alkylcarbamoyl, dialkylcarbamoyl, alkoxy(alkyl)carbamoyl or aminoalkylcarbamoyl are commercially available or can be readily prepared by one of ordinary skill in the art. For example, reactive piperazine intermediates in which R$_1$ or R$_2$ forms an amide derivative can be prepared by acylation of an appropriate amine, or protected derivative thereof, with an appropriate protected carboxylic acid (e.g. N-protected 2-piperazinecarboxylic acid) and then deprotecting. The protected piperazine carboxylic acid is prepared from commercially available starting material via standard protection chemistry.

As will be appreciated in the art, the above synthetic techniques may be used to synthesize the cysteine protease inhibitors of the invention. Representative examples of such syntheses are outlined in the Examples.

In one embodiment, the cysteine protease inhibitors of the present invention are further purified if necessary after synthesis, for example to remove unreacted materials. For example, the cysteine protease inhibitors of the present invention may be crystallized, or passed through chromatography columns using solvent mixtures to elute the pure inhibitors.

Once produced, the cysteine protease inhibitors of the present invention may be easily screened for their inhibitory effect. The inhibitor is first tested against the cysteine protease for which the targeting group of the inhibitor was chosen, as outlined above. Alternatively, many cysteine proteases and their corresponding chromogenic substrates are commercially available. Thus, a variety of cysteine proteases are routinely assayed with synthetic chromogenic substrates in the presence and absence of the cysteine protease inhibitor, to confirm the inhibitory action of the compound, using techniques well known in the art. The effective inhibitors are then subjected to kinetic analysis to calculate the K$_I$ values, and the dissociation constants determined.

If a compound inhibits at least one cysteine protease, it is a cysteine protease inhibitor for the purposes of the invention. Preferred embodiments have inhibitors that exhibit the correct kinetic parameters against at least the targeted cysteine protease.

In some cases, the cysteine protease is not commercially available in a purified form. The cysteine protease inhibitors of the present invention may also be assayed for efficacy using biological assays. For example, the inhibitors may be added to cells or tissues that contain cysteine proteases, and the biological effects measured.

In one embodiment, the cysteine protease inhibitors of the present invention are synthesized or modified such that the in vivo and in vitro proteolytic degradation of the inhibitors is reduced or prevented. Generally, this is done through the incorporation of synthetic amino acids, derivatives, or substituents into the cysteine protease inhibitor. Preferably, only one non-naturally occurring amino acid or amino acid side chain is incorporated into the cysteine protease inhibitor, such that the targeting of the inhibitor to the enzyme is not significantly affected. However, some embodiments that use longer cysteine protease inhibitors containing a number of targeting residues may tolerate more than one synthetic derivative. In addition, non-naturally occurring amino acid substituents may be designed to mimic the binding of the naturally occurring side chain to the enzyme, such that more than one synthetic substituent is tolerated. Alternatively, peptide isosteres are used to reduce or prevent inhibitor degradation.

In this embodiment, the resistance of the modified cysteine protease inhibitors may be tested against a variety of known commercially available proteases in vitro to determine their proteolytic stability. Promising candidates may then be routinely screened in animal models, for example using labelled inhibitors, to determine the in vivo stability and efficacy.

In one embodiment, the cysteine protease inhibitors of the present invention are labelled. By a "labelled cysteine protease inhibitor" herein is meant a cysteine protease inhibitor that has at least one element, isotope or chemical compound attached to enable the detection of the cysteine protease inhibitor or the cysteine protease inhibitor bound to a cysteine protease. In general, labels fall into three classes: a) isotopic labels, which may be radioactive or heavy isotopes; b) immune labels, which may be antibodies or antigens; and c) colored or fluorescent dyes. The labels may be incorporated into the cysteine protease inhibitor at any position. Examples of useful labels include $^{14}C$, $^3H$, biotin, and fluorescent labels as are well known in the art.

In the preferred embodiment, the cysteine protease inhibitors of the present invention are administered to a patient to treat cysteine protease-associated disorders. By "cysteine protease-associated disorders" or grammatical equivalents herein is meant pathological conditions associated with cysteine proteases. In some disorders, the condition is associated with increased levels of cysteine proteases; for example, arthritis, muscular dystrophy, inflammation, tumor invasion, and glomerulonephritis are all associated with increased levels of cysteine proteases. In other disorders or diseases, the condition is associated with the appearance of an extracellular cysteine protease activity that is not present in normal tissue. In other embodiments, a cysteine protease is associated with the ability of a pathogen, such as a virus, to infect or replicate in the host organism.

Specific examples of cysteine protease associated disorders or conditions include, but are not limited to, arthritis, muscular dystrophy, inflammation, tumor invasion, glomerulonephritis, malaria, Alzheimer's disease, disorders associated with autoimmune system breakdowns, periodontal disease, cancer metastasis, trauma, inflammation, gingivitis, leishmaniasis, filariasis, osteoporosis and osteoarthritis, and other bacterial and parasite-borne infections, and others outlined above.

In particular, disorders associated with interleukin 11t3 converting enzyme (ICE) are included, as outlined above.

In this embodiment, a therapeutically effective dose of a cysteine protease inhibitor is administered to a patient. By "therapeutically effective dose" herein is meant a dose that produces the effects for which it is administered. The exact dose will depend on the disorder to be treated and the amount of cysteine protease to be inhibited, and will be ascertainable by one skilled in the art using known techniques. In general, the cysteine protease inhibitors of the present invention are administered at about 1 to about 1000 mg per day. For example, as outlined above, some disorders are associated with increased levels of cysteine proteases. Due to the 1:1 stoichiometry of the inhibition reaction, the dose to be administered will be directly related to the amount of the excess cysteine protease. In addition, as is known in the art, adjustments for inhibitor degradation, systemic versus localized delivery, and rate of new protease synthesis, as well as the age, body weight, general health, sex, diet, time of administration, drug interaction and the severity of the disease may be necessary, and will be ascertainable with routine experimentation by those skilled in the art.

A "patient" for the purposes of the present invention includes both humans and other animals and organisms. Thus the methods are applicable to both human therapy and veterinary applications. For example, the veterinary applications include, but are not limited to, canine, bovine, feline, porcine, caprine, equine, and ovine animals, as well as other domesticated animals including reptiles, such as iguanas, turtles and snakes, birds such as finches and members of the parrot family, lagomorphs such as rabbits, rodents such as rats, mice, guinea pigs and hamsters, amphibians, fish, and arthropods. Valuable non-domesticated animals, such as zoo animals, may also be treated. In the preferred embodiment the patient is a mammal, and in the most preferred embodiment the patient is human.

The administration of the cysteine protease inhibitors of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the cysteine protease inhibitors may be directly applied as a solution or spray.

The pharmaceutical compositions of the present invention comprise a cysteine protease inhibitor in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Synthesis of Cysteine Protease Inhibitor with a Carbamoyl Peptidyl A Group, a Sulfonyl X Group, and Ethylenediamine Backbone Unless otherwise indicated, all reactions were performed under an inert atmosphere of argon at room temperature.

THF was distilled from sodium benzophenone ketyl. All other solvents and commercially available material were used without further purification. Unless otherwise noted, all reagents were obtained from Aldrich, Inc.

(4-morpholinecarbonylphenylalanyl)-2-phenethyl-1-phenylsulfonyl ethylenediamine (Mu-Phe-retro-(D,L)-Hph-SO$_2$Ph)

To a suspension of homophenylalanine (Synthetech) (7 g, 39.1 mmol) in distilled water (21.5 mL) was added a 2 M aqueous NaOH (21.5 mL). After 5 minutes, the suspension had cleared and phenylsulfonyl chloride (5.48 mL, 43 mmol) was added. After 2 hours, the reaction mixture's pH was adjusted to 12 with 2 M aqueous NaOH (5 mL), and extracted with Et$_2$O (2×100 mL). The aqueous layer's pH was adjusted to 1 with 6 M HCl (10 mL), and the product was extracted with EtOAc (100 mL), dried over MgSO$_4$ filtered, and the solvent was removed under reduced pressure. The residue was triturated with Et$_2$O (2×100 mL), filtered, and pumped to dryness, giving 8.74 g (70%) of phenylsulfonylhomophenylalanine.

To a solution of 4-morpholinecarbonylphenylalanine (Mu-PheOH, 0.14 g, 0.48 mmol, prepared according to the method described in Esser, R. et.al., Arthritis & Rheumatism (1994), 37, 236) in THF (10 mL)) at −10° C. were added 4-methylmorpholine (0.11 mL, 0.96 mmol), followed by isobutyl chloroformate (64 μL, 0.48 mmol). After 5 minute activation, 2-phenethyl-1-phenylsulfonylethylenediamine hydrochloride (0.15 g, 0.44 mmol, prepared by conversion of the N-phenylsulfonylhomophenylalanine to the amide via CDI/NH$_3$/THF reaction, then by reduction of the carbonyl amide to its corresponding amine with lithium aluminium hydride, followed by treatment with HCl in dioxane) was added. After 1 hour, the reaction mixture was diluted with CH$_2$Cl$_2$ (50 mL) and washed with 1 M HCl (50 mL) followed by saturated aqueous NaHCO$_3$ (50 mL), dried over MgSO$_4$, filtered, and the solvent was removed under reduced pressure. The residue was diluted with CH$_2$Cl$_2$ (5 mL) and precipated from hexane (200 mL), filtered, and dried in vacuo yielding 0.22 g (89%) of the desired product.

Thin-layer chromatography (TLC) was performed on each sample. Visualization was accomplished by means of a UV light at 254 nm, followed by ninhydrin, bromocreosol green, or p-anisaldehyde stain. The retention factor (R.) of the Mu-Phe-retro-(D,L)-Hph-SO$_2$Ph was 0.67 (10% MeOHt/CH$_2$Cl$_2$).

Example 2

Synthesis of a Cysteine Protease Inhibitor with an Acyl Peptidyl A Group, a Sulfonyl X Group, and an Ethylenediamine Backbone Synthesis of 2-butyl-4-(pivaloyl-2-naphthylalanyl)-1-phenylsulfonyl ethylenediamine (abbreviated Piv-Np2-retro-(D,L)-NleSO$_2$Ph). To a solution of HCl*norleucine methyl ester (4.87 9, 26.8 mmol) in THF (20 mL) were added triethylamine (8.22 mL, 59 mmol) and phenylsulfonyl chloride (3.76 mL, 30 mmol). After 16 hours, the solvent was removed under reduced pressure. The residue was dissolved in EtOAc (100 mL) and washed with 1 M HCl, saturated aqueous NaHCO$_3$, dried over MgSO$_4$, and filtered. The solvent was removed under reduced pressure giving 6.04 g (79%) of N-phenylsulfonylnorleucine methyl ester.

To a solution of t-butoxycarbonyl-2-naphthylalanine (Synthetech) (0.59 9, 1.88 mmol) in THF (25 mL) at −10° C. were added 4-methylmorptnoline (0.41 mL, 3.8 mmol), followed by isobutyl chloroformate (0.25 mL, 1.88 mmol). After 5 minute activation, 2-(D,L)-butyl-1-phenyl sulfonyl-ethylenediamine hydrochloride (0.5 g, 1.7 mmol, prepared by conversion of the N-phenylsulfonylnorleucine methyl ester to its corresponding acid, by aqueous sodium hydroxide treatment; amide formation, CDI/NH$_3$; reduction of the carbonyl amide to its corresponding amine; followed by HCl dioxane treatment) was added. After 1 hour, the reaction was diluted with EtOAc (100 mL) and washed with 1 M HCl (50 mL), saturated aqueous NaHCO$_3$ (50 mL), dried over MgSO$_4$, and filtered. The solvent was removed under reduced pressure, triturated with hexane (15 mL) and dried in vacuo, giving 0.40 g (76%) of Boc-Np2-retro-(D,L)-NleSO$_2$Ph.

To a solution of HCl*Np2-retro-(D,L)-NleSO$_2$Ph (0.97 9, 1.98 mmol, prepared by conversion of Boc-Np2-retro-(D,L)-NleSO$_2$Ph to HCl*Np2-retro-(D,L)-NleSO$_2$Ph via HCl/dioxane) in THF (25 mL) at −10° C. were added pivaloyl chloride (0.27 mL, 2.2 mmol) and 4-methylmorpholine (0.48 mL, 4.4 mmol). After 1 hour, the reaction mixture was diluted with CH$_2$Cl$_2$ (100 mL) and washed with 1 M HCl (100 mL), saturated aqueous NaHCO$_3$(100 mL), dried over MgSO$_4$, and filtered. The solvent was removed under reduced pressure yielding 0.66 g (66%) of Piv-Np2-retro-(D,L)-NleSO$_2$Ph TLC: Rf=0.3 (20% EtOAc/CH$_2$Cl$_2$).

Example #3

Synthesis of a Cysteine Protease Inhibitor containing a Sulfonyl Peptidyl A Group, a Sulfonyl X Group, and a Piperazine Backbone Synthesis of 2-butyl-1-(2-naphthylsulfonyl)-4-(phenylsulfonyl-2-naphthylalanyl)-1,4-piperazine, abbreviated PhSO$_2$-Np2-pip-retro-(D,L)-NleSO$_2$2Np.

To a solution, Z-Nle-OH (10 g, 38 mmol) in THF (100 mL) at −10° C. were added pyridine (6.7 mL, 83 mmol), and thionyl chloride (3.02 mL, 42 mmol). After 30 minutes, triethylamine (11.6 mL, 83 mmol) and N-benzylglycine ethyl ester (5.4 mL, 42 mmol) were added. After 2 hours, the reaction mixture was diluted with EtOAc (200 mL) and washed with 1 M HCl (150 mL), saturated aqueous NaHCO$_3$ (150 mL), dried over MgSO$_4$, and filtered. The solvent was removed under reduced pressure, yielding 16.61 (100%) of Z-norleucyl-N-benzylglycine ethyl ester.

To a solution of HBr*notreucyl-N-benzylglycine ethyl ester (14.6 9, 38 mmol, prepared by conversion of the Z-norleucyl-N-benzylglycine ethyl ester to its HBr salt with 30% HBr in AcOH.) in EtOH (50 mL) was added triethylamine (13.2 mL, 94 mmol). After 2 hours the solvent was removed under reduced pressure. The residue was dissolved in EtOAc (100 mL) and washed with 1 M HCl (100 mL), saturated aqueous NaHCO$_3$ (100 mL), dried over MgSO$_4$, and filtered. Diluted with Et$_2$O ( 300 mL) and placed at 0° C. for 2 hours. The solution was filtered and the solid was dried in vacuo yielding 6.3 g (64%) 1-benzyl-3-butyldiketo-1,4-piperazine.

To a solution of 2(HCl)*1-benzyl-3-butyl-1,4-piperazine (2.2 g, 8.2 mmol, prepared by conversion of 1-benzyl-3-butyldiketo-1,4-piperazine to 4-benzyl-3-butyl-1,4-piperazine via reduction with lithium aluminum hydride followed by HCl/dioxane treatment) in THF (50 mL) were added, BSA (4.4 mL, 18 mmol), triethylamine (2.5 mL, 18 mmol), and 2-naphthylsulfonyl chloride (2 g, 9 mmol). After 16 hours, the reaction mixture was diluted with EtOAc (100 mL) and washed with 1 M HCl (100 mL), saturated aqueous NaHCO$_3$ (100 mL), dried over MgSO$_4$, and filtered. The solvent was removed under reduced pressure and the residue was diluted with CH$_2$Cl$_2$ (100 mL). A mixture of MgSO$_4$/ activated carbon/silica (1:1:1, 5 g) was added to the solution, heated to reflux for 5 minutes, and filtered. The solvent was removed under reduced pressure yielding 2.7 g (80%) of 4-benzyl-2-butyl-1-(2-naphthylsulfonyl)-1,4-piperazine.

To a solution of Z-(2-naphthylalanine) (2.1 g , 5.9 mmol, prepared by conversion of 2-naphthylalanine (Synthetech) to its Z-derivative with benzyloxycarbonyl chloride.) in THF (50 mL) at −10° C. were added pyridine (0.96 mL, 12 mmol), thionyl chloride (0.43 mL, 5.9 mmol). After 30 minutes, a solution of 2-butyl-1-(2-naphthylsulfonyl)-1,4-piperazine hydrochloride (2.4 g, 5.4 mmol, prepared by conversion of 1-benzyl-3-butyl-1-(2-naphthylsulfonyl)-1,4-piperazine to 2-butyl-1-(2-naphthylsulfonyl)-1,4-piperazine with $H_2$/5% Pd/C/IPA (isopropanol) in a Parr apparatus, and followed by HCl/dioxane treatment) BSA (1.5 mL, 5.9 mmol), and triethylamine (1.7 mL, 12 mmol) in $CH_2Cl_2$ (50 mL) was added. After 1 hour, the reaction mixture was diluted in $CH_2Cl_2$ (100 mL) and washed with 1 M HCl (100 mL), saturated aqueous $NaHCO_3$, dried over $MgSO_4$, and filtered. The solvent was removed under reduced pressure, diluted with $Et_2O$ (10 mL), precipitated from hexane (100 mL), filtered, and dried in vacuo giving 1.7 g (43%) of 4-(Z-(2-naphthyl-alanyl))-2-butyl-1-(2-naphthylsulfonyl)-1,4-piperazine.

To a solution of 4-(2-naphthylalanyl)-2-butyl-1-(2-naphthylsulfonyl)-1,4-piperazine hydrobromide (0.2 g, 0.35 mmol prepared from the Z derivative via 30% HBr in AcOH) in THF (20 mL) at −10° C. were added BSA (0.19 mL, 0.76 mmol), phenylsulfonyl chloride (50 µL, 0.38 mmol), and triethylamine (0.11 mL, 0.76 mmol). After 1 hour, the reaction mixture was diluted with EtOAc (50 mL), washed with 1 M HCl (50 mL), saturated aqueous $NaHCO_3$ (100 mL), dried over $MgSO_4$, and filtered. The solvent was removed under reduced pressure, and the residue was diluted with $CH_2Cl_2$ (5 mL), precipitated with diisopropyl ether (50 mL), filtered, and dried in vacuo giving 0.1 g (43%) of final product. TLC: $R_f$=0.78 (50% EtOAc/$CH_2Cl_2$)

Example #4

Synthesis of Cysteine Protease Inhibitor Containing a Alkyloxycarbonyl Peptidyl A Group, a Sulfonyl X Group, and a Piperazine Backbone Synthesis of 4-(benzyloxycarbonyl-2-naphthylalanyl)-1-(2-naphthylsulfonyl)-1,4-piperazine, abbreviated Z-Np2-pip-GlySO$_2$Np.

To a suspension of piperazine (3.4 g, 40 mmol) in the THF (100 mL) at 0° C. were added BSA (9.8 mL, 40 mmol) and 2-naphthylsulfonyl chloride (3 g, 13 mmol). After 30 minutes, the reaction was filtered and the solvent was removed under reduced pressure. The residue was diluted in $CH_2Cl_2$ (100 mL), washed with saturated aqueous $NaHCO_3$ (100 mL), dried over $MgSO_4$., and filtered. The solvent was removed under reduced pressure, triturated with $Et_2O$ (20 mL)/hexane (20 mL), and dried in vacuo giving 3.4 g (92%) 1-(2-naphthylsulfonyl)-1,4-piperazine.

To a solution of Z-(2-naphthylalanine) (2.1 g, 5.8 mmol) in THF (50 mL) at 0° C. were added pyridine (0.97 mL, 11 mmol) and thionyl chloride (0.43 mL, 6 mmol). After 30 minutes, 1-(2-naphthylsulfonyl)-1,4-piperazine (1.5 g, 5.4 mmol) and triethylamine (1.7 mL, 12 mmol) were added. After 1 hour the reaction was diluted with EtOAc (100 mL), washed with 1 M HCl (100 mL), saturated aqueous $NaHCO_3$ (100 mL), dried over $MgSO_4$, filtered The solvent was removed under reduced pressure and diluted with $CH_2Cl_2$ (20 mL), precipated from hexane (200 mL), filtered, and dried in vacuo giving 1.8 g (55%) of the desired product. TLC: $R_f$=0.39 (50% EtOAc/hexane).

Example #5

Synthesis of Cysteine Protease Inhibitor Containing an Acyl Peptidyl A Group, a Sulfonyl X Group, and a Piperazine Backbone Synthesis of 1-benzylsulfonyl-4-(phenylacetyl-(2-naphthyl alanyl))-1,4-piperazine, abbreviated Phac-Np2-pip-GlySO$_2$Bzl.

To a suspension of piperazine (4 g, 46 mmol) in THF (100 mL) at −10° C. were added BSA (11.5 mL, 46 mmol) and α-toluenesulfonyl chloride (3 g, 15 mmol). After 1 hour the reaction was filtered, diluted with EtOAc (100 mL), washed with saturated aqueous $NaHCO_3$, dried over $MgSO_4$, and filtered. The solvent was removed under reduced pressure, and the residue was triturated with $Et_2O$ (20 mL)/hexane (20 mL), and pumped to a solid giving 2.5 g (67%) of 1-benzylsulfonyl-1,4-piperazine.

To a solution of Z-(2-naphthylalanine) (0.81 g, 6.9 mmol) in THF (50 mL) were added pyridine (1.12 mL, 13.7 mmol) and thionyl chloride (0.5 mL, 6.9 mmol). After 30 minutes, a solution of 1-benzylsulfonyl-1,4-piperazine (1.5 g, 6.2 mmol), BSA (3.4 mL, 13.7 mmol), and triethylamine (1.9 mL, 13.7 mmol) in THF (50 mL) was added. After 2 hours, the reaction mixture was diluted with EtOAc (200 mL), washed with 1 M HCl (200 mL), saturated aqueous $NaHCO_3$ (200 mL) dried over $MgSO_4$, and filtered. The solvent was removed under reduced pressure. The residue was dissolved in $CH_2Cl_2$ (30 mL), precipitated from hexane (200 mL), filtered, and dried in vacuo giving 1.5 g (70%) of 4-(benzyloxycarbonyl-(2-naphthylalanyl)-1-benzylsulfonyl-1,4-piperazine, Z-Np2-pip-GlySO$_2$Bzl.

To a solution of 4-(2-napthylalanyl)-1-benzylsulfonyl-1,4-piperazine (0.40 g, 0.77 mmol, prepared by conversion of Z-Np2-pip-GlySO$_2$Bzl to its HBr salt with 30% HBr in AcOH) in THF (50 mL) at −10° C. were added phenylacetyl chloride (0.11 mL, 0.84 mmol) and triethylamine (0.23 mL, 1.7 mmol). After 1 hour, the reaction was diluted with EtOAc (100 mL), washed with 1 M HCl (100 mL), saturated aqueous $NaHCO_3$ (100 mL), dried over $MgSO_4$, and filtered. The solvent was removed under reduced pressure, and the residue was dissolved in $CH_2Cl_2$ (10 mL), precipitated from hexane (100 mL), filtered, and dried in vacuo yielding 0.28 g (65%) of the desired product. TLC: $R_f$=0.39 (20% EtOAC/$CH_2Cl_2$)

The remainder of the compounds depicted in FIG. 1 were synthesized using the above techniques.

Example 6

Inhibition Kinetics

Conditions for cathepsin B: 50 mM phosphate, pH 6.0, 2.5 mM EDTA, 2.5 mM DTT. Substrate: [Z-Arg-Arg-AMC]=50 µM (Km=190 µM). The assay at 250 was started by the addition of cat B (final concentration approx 10 nM) and the increase in fluorescence at 450 nm with excitation at 380 nm was followed over 2 min. The depression in the rate of substrate hydrolysis following addition of varying concentrations of inhibitors was noted. The assay was linear throughout the range observed. Duplicate runs were measured.

Conditions for cathepsin L: 50 mM acetate, pH 5.5, 2.5 mM EDTA, 2.5 mM DTT. Substrate: [Z-PhteArg-AMC]=5 µM (Km=2 µM). The assay at 25° was started by the addition of cat L (final concentration approx 1 nM) and the increase in fluorescence at 450 nm with excitation at 380 nm was followed over 2 min. The depression in the rate of substrate hydrolysis following addition of varying concentrations of inhibitors was noted. The assay was linear throughoutt-the range observed. Duplicate runs were measured.

Conditions for cathepsin S: 50 mM phosphate, pH 6.5, 2.5 mM EDTA, 2.5 mM DTT. Substrate: [Z-Val-Val-Arg-AMC]=10 μM (Km=18 μM). The assay at 25° was started by the addition of cat S (final concentration approx. 30 pM0 and the increase in fluorescence at 450 nm with excitation at 380 nm was followed over 2 min. The depression in the rate of substrate hydrolysis following addition of varying concentrations of inhibitors was noted. The assay was linear throughout the range observed. Duplicate runs were measured.

Conditions for cruzain were the same as for cathepsin L with the exception that the Km for the substrate was 1 μM.

The respective $K_I$ values were estimated by using the Dixon plot as described by Irwin Segel in Enzyme Kinetics: Behavior and analysis of rapid equilibrium and steady-state enzyme systems, 1975, Wiley-lnterscience Publication, John Wiley & Sons, New York, or for competitive binding inhibitors from the following calculation:

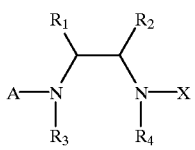

$v_o$ is the rate of substrate hydrolysis in the absence of inhibitor, whereas $v_i$ is the rate in the presence of competitive inhibitor.

We claim:

1. A reversible cysteine protease inhibitor having two N-substituents linked via an ethylenediamine or a substituted ethylenediamine, wherein the dissociation constant for inhibition, $K_I$, of a protease with the inhibitor, is no greater than about 100 μM, and wherein said N-substituents are selected from the group consisting of acyl, acyl peptidyl, alkyloxycarbonyl, alkyloxycarbonyl peptidyl, sulfonyl, peptidyl, sulfamoyl, sulfamoyl peptidyl, sulfinyl, sulfinyl peptidyl, carbamoyl, and carbamoyl peptidyl; wherein said ethylenediamine substituent is an amino acid side chain.

2. A reversible cysteine protease inhibitor having the formula:

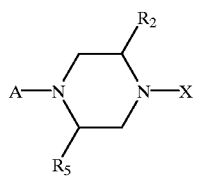

wherein

A and X are N-substituents selected from the group consisting of acyl, acyl peptidyl, alkyloxycarbonyl, alkyloxycarbonyl peptidyl, sulfonyl, peptidyl, sulfamoyl, sulfamoyl peptidyl, sulfinyl, sulfinyl peptidyl, carbamoyl, and carbamoyl peptidyl;

$R_1$ is (a) an amino acid side chain or (b) hydrogen;

$R_2$ is (a) an amino acid side chain or (b) hydrogen, wherein either (1) both $R_1$ and $R_2$ are hydrogen, or (2) one of $R_1$ or $R_2$ is an amino acid side chain and the other one of $R_1$ and $R_2$ is hydrogen; and $R_3$ and $R_4$ are hydrogen, or are bonded together to form ethylene or substituted ethylene;

wherein said ethylene substituent is an amino acid side chain;

wherein the dissociation constant for inhibition, $K_I$, of a protease with the inhibitor, is no greater than about 100 μM.

3. A reversible cysteine protease inhibitor according to claim 2 wherein $R_2$ is an amino acid side chain.

4. A reversible cysteine protease inhibitor according to claim 2 having the formula:

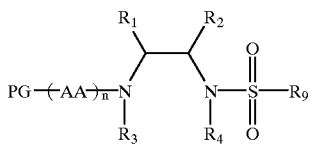

wherein $R_5$ is (a) an amino acid side chain or (b) hydrogen, wherein either both $R_2$ and $R_5$ are hydrogen, or one of $R_2$ or $R_5$ is an amino acid side chain and the other one of $R_2$ and $R_5$ is hydrogen.

5. A cysteine protease inhibitor according to claim 2 having the formula:

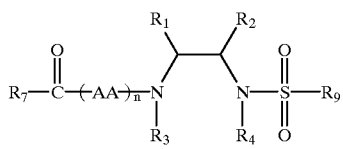

wherein n is from 1 to 10;

PG is a protecting group;

$R_9$ is selected from the group consisting of alkyl (optionally substituted with a member of the group consisting of hydroxy, alkoxy, amino, and halogens), cycloalkyl, cyloalkylalkyl, cyloalkylalkenyl, aryl, substituted aryl, aralkyl, and substituted aralkyl; wherein said substituents of said substituted aralkyl, and substituted aralkyl are 1 or 2 members of the group consisting of alkyl, alkoxy, halogens, hydroxy, and amino; and AA is an amino acid.

6. A cysteine protease inhibitor according to claim 2 having the formula:

wherein n is from 1 to 10;

AA is an amino acid;

$R_7$ is selected from the group consisting of alkyl, cycloalkyl, cycloalkylalkyl, cycloalkylalkenyl, heterocylcoalkyl, aryl, and aralkyl; wherein said aryl and aralkyl moieties are optionally substituted with one or two groups of alkyl of 1 to 5 carbon atoms, alkoxy of 1 to 5 carbon atoms, halogen of atomic number of from 9 to 35, hydroxy and/or amino, optionally protected with nitro, alkyl or arylsulfonyl, or halogen-substituted alkyl of 1 to 5 carbon atoms, or perfluoro group; wherein said heterocycloalkyl is optionally substituted with a radical selected from hydroxy, alkyl, heterocycloalkyl, alkanoyl, alkyloxycarbonyl, arylalkyloxycarbonyl and heterocycloalkylcarbonyl; and R₉ is selected from the group consisting of alkyl (optionally substituted with a member of the group consisting of hydroxy, alkoxy, amino, and halogens), cycloalkyl, cyloalkylalkyl, cyloalkylalkenyl, aryl, substituted aryl, aralkyl, and substituted aralkyl;

wherein said substituents of said substituted aryl and substituted aralkyl are 1 or 2 members of the group consisting of alkyl, alkoxy, halogens, hydroxy, and amino.

7. A pharmaceutical composition comprising a reversible cysteine protease inhibitor having the formula:

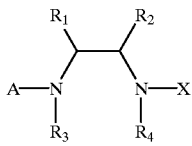

wherein
A and X are N-substituents selected from the group consisting of acyl, acyl peptidyl, alkyloxycarbonyl, alkyloxycarbonyl peptidyl, sulfonyl, peptidyl, sulfamoyl, sulfamoyl peptidyl, sulfinyl, sulfinyl peptidyl, carbamoyl, and carbamoyl peptidyl;

R₁ is (a) an amino acid side chain or (b) hydrogen;

R₂ is (a) an amino acid side chain or (b) hydrogen, wherein either both R₁ and R₂ are hydrogen, or one of R₁ or R₂ is an amino acid side chain and the other one of R₁ and R₂ is hydrogen; and R₃ and R₄ are hydrogen, or are bonded together to form ethylene or substituted ethylene;

wherein said ethylene substituent is an amino acid side chain;

wherein the dissociation constant for inhibition, $K_I$, of a protease with the inhibitor, is no greater than about 100 μM; and a pharmaceutically acceptable carrier.

8. A cysteine protease inhibitor of Formula I:

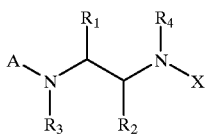

in which:
A and X are independently R₁₃—X₁—; wherein R₁₃ is hydrogen, alkyloxycarbonylalkanoyl, alkyloxycarbonyl, alkanoyl (optionally substituted with a radical selected from carboxy, alkyloxycarbonyl and heterocycloalkylalkanoylamino), cycloalkylcarbonyl, heterocycloalkylcarbonyl (optionally substituted with a radical selected from hydroxy, alkyl, heterocycloalkyl, alkanoyl, alkyloxycarbonyl, arylalkyloxycarbonyl and heterocycloalkylcarbonyl), arylalkyloxycarbonyl, carbamoyl, alkylcarbamoyl, dialkylcarbamoyl, arylcarbamoyl, arylalkylcarbamoyl, arylalkanoyl, aroyl, alkylsulfonyl, arylsulfonyl, arylalkylsulfonyl, alkylsulfamoyl, dialkylsulfamoyl, arylsulfamoyl, alkylsulfinyl, dialkylaminosulfinyl or arylsulfinyl; and X₁ is a bond or a divalent radical of Formulae (a) or (b):

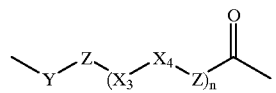

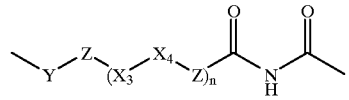

in which n is 0 to 9; X₃–X₄ represents a linkage selected from —C(O)NR₁₄—, —CH₂NR₁₄—, —C(O)CH₂— and —NR₁₄C(O)—; Y is —CH(R₁₄)— or —NR₁₄—; and Z is —(CH₂)₂—, —C(R₁₅)(R₁₆)— or —N(R₁₆)—; wherein R₁₄ is hydrogen or as defined below; R₁₅ is hydrogen or methyl; and each R₁₆ is independently hydrogen, alkyl (optionally substituted with a radical selected from hydroxy, alkyloxy, amino, alkylamino, dialkylamino, ureido, alkylureido, mercapto, alkylthio, carboxy, carbamoyl, alkylcarbamoyl, dialkylcarbamoyl, alkylsulfinyl, alkylsulfonyl, guanidino, —P(O)(OR₁₂)₂, —OP(O)(OR₁₂)₂ or —OP(O)(R₁₂)₂, wherein each R₁₂ is independently hydrogen or alkyl, or a protected derivative thereof), cycloalkyl, cycloalkylalkyl, aryl or arylalkyl (wherein said aryl ring is optionally substituted with one to three radicals selected from hydroxy, amino, guanidino, halo, optionally halo-substituted alkyl, alkyloxy and aryl, or a protected derivative thereof) or together with an adjacent R₁₄ forms a divalent radical selected from (C₃₋₄)methylene and 1,2-phenylenedimethylene (which radical is optionally substituted with hydroxy, or a protected derivative thereof, or oxo), with the proviso X and A are not both hydrogen;

R₁ and R₂ are both hydrogen or one of R₁ or R₂ is cyano, carboxy, alkyloxycarbonyl, alkanoyl, carbamoyl, alkylcarbamoyl, dialkylcarbamoyl, alkyloxy(alkyl)carbamoyl, aminoalkylcarbamoyl, R₁₆, as defined above, or R₁₃—X₂—, wherein R₁₃ is as defined above and X₂ is a divalent radical of Formulae (a) or (b), as defined above; and R₃ and R₄ are hydrogen or together form —CHR₅, —CHR₆, wherein R₅ and R₆ are both hydrogen or one of R₅ or R₆ is R₁₆ or R₁₃—X₂—, wherein R₁₆, R₁₃, and X₂ are as defined above, with the proviso that R₅ is hydrogen, when R₃ is R₁₆ or R₁₃—X₂—, and R₆ is hydrogen when R₄ is R₁₆ or R₁₃—X₂—; and the pharmaceutically acceptable salts, individual isomers and mixtures of isomers thereof.

9. The compound of claim 8 in which A is R₁₃—X₁—; wherein R₁₃ is hydrogen, alkyloxycarbonylalkanoyl of overall 3 to 10 carbon atoms, (C₁₋₉)alkoxycarbonyl, (C₂₋₁₀)alkanoyl (optionally substituted with a radical selected from carboxy, (C₁₋₉)alkyloxycarbonyl and hetero(C₄₋₈)cycloalkyl (C₂₋₁₀)alkanoylamino), (C₄₋₈)cycloalkylcarbonyl, hetero (C₄₋₈)cycloalkylcarbonyl (optionally substituted with a radical selected from hydroxy, (C₁₋₅)alkyl, hetero(C₄₋₈)cycloalkyl, (C₁₋₅)alkanoyl, (C₁₋₅)alkyloxycarbonyl, (C₆₋₁₀)aryl(C₁₋₅)alkyloxycarbonyl and hetero(C₄₋₈)cycloalkylcarbonyl), (C₆₋₁₀)aryl(C₁₋₅)alkyloxycarbonyl, carbamoyl, (C₁₋₅)alkylcarbamoyl, di(C₁₋₅)alkylcarbamoyl, (C₆₋₁₀)arylcarbamoyl, (C₆₋₁₀)aryl(C₁₋₅)alkylcarbamoyl, (C₆₋₁₀)aryl(C₁₋₅)alkanoyl, (C₇₋₁₁)aroyl, (C₁₋₁₀)alkylsulfonyl, di(C₁₋₅)alkylsulfamoyl, (C6-10)arylsulfonyl, (C₆₋₁₀)aryl(C₁₋₅)alkylsulfonyl or hetero(C₄₋₈)arylsulfonyl; and X₁ is a divalent radical of Formula (a), wherein n is 0 to 5; X₃–X₄ represents —C(O)NR₁₄—; Y is —N(R₁₄)—; Z is —CH ($R_{16}$)—; each $R_{16}$ is independently hydrogen, ($C_{3-7}$) cycloalkyl, ($C_{3-7}$)cycloalkyl($C_{1-5}$)alkyl, pyridyl, thienyl, furyl, imidazolyl, indolyl, pyridyl($C_{1-6}$)alkyl, thienyl($C_{1-6}$) alkyl, furyl($C_{1-6}$)alkyl, imidazolyl($C_{1-6}$)alkyl, indolyl($C_{1-6}$) alkyl, ($C_{1-5}$)alkyl (optionally substituted with a radical selected from mercapto, carboxy, amino, methylthio, methylsulfonyl, carbamoyl, dimethylcarbamoyl, guanidino and hydroxy, or a protected derivative thereof) phenyl, naphthyl, phenyl($C_{1-6}$)alkyl, naphthyl($C_{1-6}$)alkyl, (which group is optionally substituted at its aryl ring with one to three radicals selected from amino, hydroxy, chloro, bromo, fluoro, iodo, methyl, trifluoromethyl, methoxy and phenyl, or a protected derivative thereof) or together with an adjacent $R_{14}$ forms a divalent radical selected from ($C_{3-4}$) methylene and 1,2-phenylenedimethylene (which radical is optionally substituted with hydroxy, or a protected derivative thereof, or oxo);

X is —S(O)$_2$R$_9$; wherein R$_9$ is ($C_{1-5}$)alkyl (optionally substituted with one or two radicals selected from amino, chloro, bromo, fluoro, hydroxy and methoxy, or a protected derivative thereof), perhalo($C_{1-5}$) alkylsulfonyl, ($C_{3-7}$)cycloalkyl, ($C_{3-7}$)cycloalkyl($C_{1-5}$) alkyl, phenyl, pentafluorophenyl, naphthyl or phenyl ($C_{1-6}$)alkyl (which group is optionally substituted at its aryl ring with one to two radicals selected from amino, chloro, bromo, fluoro, hydroxy, methoxy and optionally halo-substituted methyl, or a protected derivative thereof);

R$_1$ is hydrogen and R$_2$ is R$_{16}$, as defined above.

10. The compound of claim 9 wherein n is 0 to 2; R$_2$ is R$_{16}$ as defined below; R$_{13}$ is hydrogen, ($C_{4-8}$) alkoxycarbonyl, ($C_{2-6}$)alkanoyl (optionally substituted with a radical selected from carboxy, ($C_{1-5}$)alkyloxycarbonyl and hetero($C_{4-8}$)cycloalkyl($C_{4-6}$)alkanoylamino), or —C(O) NR$_{10}$R$_{11}$; wherein R$_{10}$ and R$_{11}$ together form aza($C_{2-6}$) methylene, oxa($C_{2-6}$)methylene, ($C_{3-7}$)methylene, ($C_{4-8}$) cycloalkylcarbonyl, benzyloxycarbonyl, acetyl, benzoyl or dimethylsulfamoyl; R$_{16}$ ($C_{5-6}$)cycloalkyl, ($C_{5-6}$) cycloalkylmethyl, 3-pyridyl, 2-thienyl, 2-furyl, 4-imidazolyl, 3-indolyl, 3-pyridylmethyl, 2-thienylmethyl, 2-furylmethyl, 4-imidazolylmethyl, 3-indolylmethyl, methoxy, acetoxy, ($C_{1-5}$)alkyl (optionally substituted with a radical selected from mercapto, carboxy, amino, methylthio, methylsulfonyl, carbamoyl, dimethylcarbamoyl, guanidino and hydroxy, or a protected derivative thereof), phenyl, 1-naphthyl, 2-naphthyl, benzyl, 1-naphthylmethyl, 2-naphthylmethyl, 2-phenylethyl (which group is optionally substituted at its aryl ring with one radical selected from hydroxy, amino, chloro, bromo and fluoro, or a protected form thereof) or together with an adjacent R$_{14}$ forms a divalent radical selected from ($C_{3-4}$)methylene and 1,2-phenylenedimethylene (which radical is optionally substituted with hydroxy, or a protected derivative thereof, or oxo); and R$_9$ is ($C_{1-5}$)alkyl (optionally substituted with one or two radicals selected from amino, chloro, bromo, fluoro and hydroxy, or a protected derivative thereof), perfluoro ($C_{1-5}$)alkyl, ($C_{5-6}$)cycloalkyl, ($C_{5-6}$)cycloalkylmethyl, phenyl, naphthyl or benzyl (which group is optionally substituted with one radical selected from amino hydroxy, chloro, bromo and fluoro, or a protected derivative thereof).

11. The compound of claim 10 in which n is 0 to 1; R$_2$ is butyl, 2-phenylethyl, 2-methylsulfonylethyl, 2-tert-butoxycarbonylethyl, 2-tert-butoxycarbonylmethyl, 4-tert-butoxycarbonylaminobutyl, 4-benzoylaminobutyl or benzyloxymethyl; R$_{13}$ is hydrogen, tert-butoxycarbonyl, benzyloxycarbonyl, acetyl, 3-carboxypropionyl, 3-methoxycarbonylpropionyl, biotinylaminohexanoyl, phenylacetyl, benzoyl, dimethylsulfamoyl, benzylsulfonyl, 1-piperizinylcarbonyl, 4-methyl-1-piperazinylcarbonyl or 4-morpholinylcarbonyl; R$_{16}$ is 3-pyridylmethyl, 2-thienylmethyl, 2-furylmethyl, 4-imidazolylmethyl, 3-indolylmethyl, ($C_{1-5}$)alkyl (optionally substituted with a radical selected from mercapto, carboxy, amino, methylthio, methylsulfonyl, carbamoyl, dimethylcarbamoyl, guanidino and hydroxy, or a protected derivative thereof), benzyl, 1-naphthylmethyl, 2-naphthylmethyl and 2-phenylethyl (which group is optionally substituted at its aryl ring with one radical selected from hydroxy, amino, chloro, bromo and fluoro, or a protected form thereof) or together with an adjacent R$_3$ or R$_{13}$ forms a divalent radical selected from ($C_{3-4}$)methylene and 1,2-phenylenedimethylene (which radical is optionally substituted with hydroxy, or a protected derivative thereof, or oxo); and R$_9$ is methyl, trifluoromethyl, optionally substituted phenyl, 2-naphthyl or 2-phenylethyl.

12. The compound of claim 11 in which n is 0; R$_2$ is butyl, 2-phenylethyl or 2-methylsulfonylethyl; R$_{13}$ is hydrogen, tert-butxoycarbonyl, benzyloxycarbonyl, biotinylaminohexanoyl, benzoyl, 1-piperiziny-carbonyl, 4-methyl-1-piperazinylcarbonyl or 4-morpholinylcarbonyl; R$_{16}$ is ($C_{1-5}$)alkyl, optionally substituted benzyl, 1-naphthylmethyl, 2-naphthylmethyl, 3-pytrdinylmethyl or 2-methylsulfonylethyl; and R$_9$ is phenyl, 1-naphthyl or 2-phenylethyl.

13. A cysteine protease inhibitor according to claim 2 wherein at least one of R$_1$ and R$_2$ is an amino acid side chain.

14. A compound according to claim 8 wherein at least one of R$_1$ and R$_2$ is cyano, carboxy, alkyloxycarbonyl, alkanoyl, carbamoyl, alkylcarbamoyl, dialkylcarbamoyl, alkyloxy (alkyl)carbamoyl, aminoalkylcarbamoyl, R$_{16}$, as defined above, or R$_{13}$—X$_2$—, wherein R$_{13}$ is as defined above and X$_2$ is a divalent radical of Formulae (a) or (b).

15. A reversible cysteine protease inhibitor having the formula:

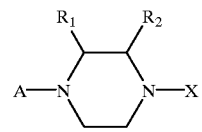

wherein

A is a N-substituent selected from the group consisting of acyl peptidyl, alkyloxycarbonyl peptidyl, peptidyl, sulfamoyl peptidyl, sulfinyl peptidyl, and carbamoyl peptidyl; X is a N-substituent selected from the group consisting of acyl, acyl peptidyl, alkyloxycarbonyl, alkyloxycarbonyl peptidyl, sulfonyl, sulfonyl peptidyl, peptidyl, sulfamoyl, sulfamoyl peptidyl, sulfinyl, sulfinyl peptidyl, carbamoyl, and carbamoyl peptidyl;

R$_1$ is hydrogen;

R$_2$ is an amino acid side chain;

wherein the dissociation constant for inhibition, K$_I$, of a protease with the inhibitor, is no greater than about 100 µM.

16. A pharmaceutical composition comprising a reversible cysteine protease inhibitor having the formula:

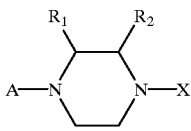

wherein

A is a N-substituent selected from the group consisting of acyl peptidyl, alkyloxycarbonyl peptidyl, peptidyl, sulfamoyl peptidyl, sulfinyl peptidyl, and carbamoyl peptidyl; X is a N-substituent selected from the group consisting of acyl, acyl peptidyl, alkyloxycarbonyl, alkyloxycarbonyl peptidyl, sulfonyl, sulfonyl peptidyl, peptidyl, sulfamoyl, sulfamoyl peptidyl, sulfinyl, sulfinyl peptidyl, carbamoyl, and carbamoyl peptidyl;

$R_1$ is hydrogen;

$R_2$ is an amino acid side chain;

wherein the dissociation constant for inhibition, $K_I$, of a protease with the inhibitor, is no greater than about 100 $\mu M$; and a pharmaceutically acceptable carrier.

17. A reversible cysteine protease inhibitor having the formula:

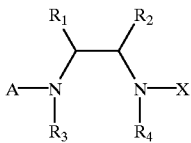

wherein

A and X are N-substituents selected from the group consisting of $C(O)R_7$ (acyl), acyl peptidyl, $C(O)OR_8$ (alkyloxycarbonyl), alkyloxycarbonyl peptidyl, $S(O)_2R_9$ (sulfonyl), peptidyl, $S(O)_2NR_{10}R_{11}$ (sulfamoyl), sulfamoyl peptidyl, $S(O)R_9$ (sulfinyl), sulfinyl peptidyl, $C(O)NR_{10}R_{11}$ (carbamoyl), and carbamoyl peptidyl;

$R_7$ is selected from the group consisting of $(C_{1-5})$alkyl, $(C_{3-7})$cycloalkyl, $(C_{3-7})$cycloalkyl$(C_{1-5})$alkyl, $(C_{3-7})$cycloalkyl$(C_{1-5})$alkenyl, hetero$(C_{3-7})$cycloalkyl, $(C_{5-14})$aryl, substituted$(C_{5-14})$aryl, $(C_{7-12})$aralkyl, and substituted$(C_{7-12})$aralkyl; wherein said hetero group is selected from the group consisting of hydroxy, $(C_{1-5})$ alkyl, hetero$(C_{3-7})$cycloalkyl, $(C_{1-5})$alkanoyl, $(C_{1-5})$ alkoxycarbonyl, $(C_{5-14})$aryl$(C_{1-5})$alkoxycarbonyl, and hetero$(C_{3-7})$cycloalkylcarbonyl;

$R_8$ is selected from the group consisting of $(C_{1-5})$alkyl (optionally substituted with a member of the group consisting of hydroxy, $(C_{1-5})$alkoxy, amino, and halogens of atomic number 9–35), $(C_{3-7})$cycloalkyl, $(C_{3-7})$cycloalkyl$(C_{1-5})$alkyl, $(C_{3-7})$cycloalkyl$(C_{1-5})$alkenyl, $(C_{5-14})$aryl, substituted$(C_{5-14})$aryl, $(C_{7-12})$aralkyl, and substituted$(C_{7-12})$aralkyl;

$R_9$ is selected from the group consisting of $(C_{1-5})$alkyl (optionally substituted with a member of the group consisting of hydroxy, $(C_{1-5})$alkoxy, amino, and halogens of atomic number 9–35), $(C_{3-7})$cycloalkyl, $(C_{3-7})$cycloalkyl$(C_{1-5})$alkyl, $(C_{3-7})$cycloalkyl$(C_{1-5})$alkenyl, $(C_{5-14})$aryl, substituted$(C_{5-14})$aryl, $(C_{7-12})$aralkyl, and substituted$(C_{7-12})$aralkyl;

$R_{10}$ and $R_{11}$ are independently selected from the group consisting of hydrogen, $(C_{1-5})$alkyl, $(C_{3-7})$cycloalkyl, $(C_{3-7})$cycloalkyl$(C_{1-5})$alkyl, $(C_{5-14})$aryl, substituted $(C_{5-14})$aryl, $(C_{7-12})$aralkyl, substituted$(C_{7-12})$aralkyl; di$(C_{1-5})$alkyl, $(C_{1-5})$alkyl$(C_{7-12})$aralkyl; or $R_{10}$ and $R_{11}$ are bonded to form a 5 or 6 membered alicyclic or heteroalicylic ring moieties;

Peptidyl is 1–10 amino acids;

said substituents of said substituted aryl and substituted aralkyl are 1 or 2 members of the group consisting of $(C_{1-5})$alkyl, $(C_{1-5})$alkoxy, halogens of atomic number 9–35, hydroxy, and amino;

$R_1$ is (a) an amino acid side chain or (b) hydrogen;

$R_2$ is (a) an amino acid side chain or (b) hydrogen, wherein either (1) both $R_1$ and $R_2$ are hydrogen, or (2) one of $R_1$ or $R_2$ is an amino acid side chain and the other one of $R_1$ and $R_2$ is hydrogen;

$R_3$ and $R_4$ are hydrogen, or are bonded together to form ethylene or substituted ethylene wherein said ethylene substituent is an amino acid side chain; and wherein the dissociation constant for inhibition, $K_I$, of a protease with the inhibitor, is no greater than about 100 $\mu M$.

18. A pharmaceutical composition comprising a reversible cysteine protease inhibitor having the formula:

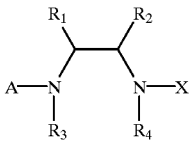

wherein

A and X are N-substituents selected from the group consisting of $C(O)R_7$ (acyl), acyl peptidyl, $C(O)OR_8$ (alkyloxycarbonyl), alkyloxycarbonyl peptidyl, $S(O)_2R_9$ (sulfonyl), peptidyl, $S(O)_2NR_{10}R_{11}$ (sulfamoyl), sulfamoyl peptidyl, $S(O)R_9$ (sulfinyl), sulfinyl peptidyl, $C(O)NR_{10}R_{11}$ (carbamoyl), and carbamoyl peptidyl;

$R_7$ is selected from the group consisting of $(C_{1-5})$alkyl, $(C_{3-7})$cycloalkyl, $(C_{3-7})$cycloalkyl$(C_{1-5})$alkyl, $(C_{3-7})$ cycloalkyl$(C_{1-5})$alkenyl, hetero$(C_{3-7})$cycloalkyl, $(C_{5-14})$aryl, substituted$(C_{5-14})$aryl, $(C_{7-12})$aralkyl, substituted$(C_{7-12})$aralkyl; wherein said hetero group is selected from the group consisting of hydroxy, $(C_{1-5})$ alkyl, hetero$(C_{3-7})$cycloalkyl, $(C_{1-5})$alkanoyl, $(C_{1-5})$ alkoxycarbonyl, $(C_{5-14})$aryl$(C_{1-5})$alkoxycarbonyl, and hetero$(C_{3-7})$cycloalkylcarbonyl;

$R_8$ is selected from the group consisting of $(C_{1-5})$alkyl (optionally substituted with a member of the group consisting of hydroxy, $(C_{1-5})$alkoxy, amino, and halogens of atomic number 9–35), $(C_{3-7})$cycloalkyl, $(C_{3-7})$ cycloalkyl$(C_{1-5})$alkyl, $(C_{3-7})$cycloalkyl$(C_{1-5})$alkenyl, $(C_{5-14})$aryl, substituted$(C_{5-14})$aryl, $(C_{7-12})$aralkyl, and substituted$(C_{7-12})$aralkyl;

$R_9$ is selected from the group consisting of $(C_{1-5})$alkyl (optionally substituted with a member of the group consisting of hydroxy, $(C_{1-5})$alkoxy, amino, and halogens of atomic number 9–35), $(C_{3-7})$cycloalkyl, $(C_{3-7})$ cycloalkyl$(C_{1-5})$alkyl, $(C_{3-7})$cycloalkyl$(C_{1-5})$alkenyl, $(C_{5-14})$aryl, substituted$(C_{5-14})$aryl, $(C_{7-12})$aralkyl, and substituted$(C_{7-12})$aralkyl;

$R_{10}$ and $R_{11}$ are independently selected from the group consisting of hydrogen, $(C_{1-5})$alkyl, $(C_{3-7})$cycloalkyl, $(C_{3-7})$cycloalkyl$(C_{1-5})$alkyl, $(C_{5-14})$aryl, substituted $(C_{5-14})$aryl, $(C_{7-12})$aralkyl, substituted$C_{7-12})$aralkyl, di$(C_{1-5})$alkyl, $(C_{1-5})$alkyl$(C_{7-12})$aralkyl; or $R_{10}$ and $R_{11}$ are bonded to form a 5 or 6 membered alicyclic or heteroalicylic ring moieties;

Peptidyl is 1–10 amino acids;

said substituents of said substituted aryl and substituted aralkyl are 1 or 2 members of the group consisting of $(C_{1-5})$alkyl, $(C_{1-5})$alkoxy, halogens of atomic number 9–35, hydroxy, and amino;

$R_1$ is (a) an amino acid side chain or (b) hydrogen;

$R_2$ is (a) an amino acid side chain or (b) hydrogen, wherein either (1) both $R_1$ and $R_2$ are hydrogen, or (2) one of $R_1$ or $R_2$ is an amino acid side chain and the other one of $R_1$ and $R_2$ is hydrogen;

$R_3$ and $R_4$ are hydrogen, or are bonded together to form ethylene or substituted ethylene wherein said ethylene substituent is an amino acid side chain;

wherein the dissociation constant for inhibition, $K_I$, of a protease with the inhibitor, is no greater than about 100 μM; and a pharmaceutically acceptable carrier.

19. A cysteine protease inhibitor of Formula I:

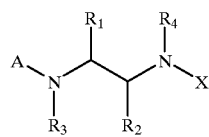

I wherein

A and X are independently $R_{13}-X_1-$;

$R_{13}$ is selected from the group consisting of hydrogen, alkyloxycarbonylalkanoyl of overall 3–10 carbon atoms, $(C_{1-9})$alkyloxycarbonyl, $(C_{2-10})$alkanoyl (optionally substituted with a radical selected from carboxy, $(C_{1-9})$alkyloxycarbonyl and hetero$(C_{4-8})$cycloalkyl$(C_{2-10})$alkanoylamino), $(C_{4-8})$cycloalkylcarbonyl, hetero$(C_{4-8})$cycloalkylcarbonyl (optionally substituted with a radical selected from hydroxy, $(C_{1-5})$alkyl, hetero$(C_{4-8})$cycloalkyl, $(C_{1-5})$alkanoyl, $(C_{1-5})$alkyloxycarbonyl, $(C_{6-10})$aryl$(C_{1-5})$alkyloxycarbonyl and hetero$(C_{4-8})$cycloalkylcarbonyl), $(C_{6-10})$aryl$(C_{1-5})$alkyloxycarbonyl, carbamoyl, $(C_{1-5})$alkylcarbamoyl, di$(C_{1-5})$alkylcarbamoyl, $(C_{6-10})$arylcarbamoyl, (C6-10)aryl$(C_{1-5})$alkylcarbamoyl, $(C_{6-10})$aryl$(C_{1-5})$alkanoyl, $(C_{7-11})$aroyl, $(C_{1-10})$alkylsulfonyl, $(C_{6-10})$arylsulfonyl, $(C_{6-10})$aryl$(C_{1-5})$alkylsulfonyl, $(C_{1-5})$alkylsulfamoyl, di$(C_{1-5})$alkylsulfamoyl, $(C_{6-10})$arylsulfamoyl, $(C_{1-5})$alkylsulfinyl, di$(C_{1-5})$alkylaminosulfinyl, and $(C_{6-10})$arylsulfinyl;

$X_1$ is a bond or a divalent radical of Formulae (a) or (b):

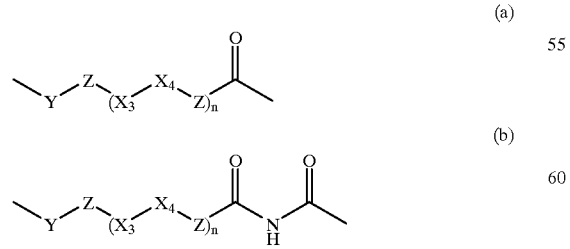

n is 0 to 9;

$X_3-X_4$ represents a linkage selected from $-C(O)NR_{14}-$, $-CH_2NR_{14}-$, $-C(O)CH_2-$ and $-NR_{14}C(O)-$;

Y is $-CH(R_{14})-$ or $-NR_{14}-$;

Z is $-(CH_2)_2'$, $-C(R_{15})(R_{16})-$ or $-N(R_{16})-$;

$R_{14}$ is hydrogen or as defined below;

$R_{15}$ is hydrogen or methyl;

each $R_{16}$ is independently hydrogen, $(C_{1-5})$alkyl (optionally substituted with a radical selected from hydroxy, $(C_{1-5})$alkyloxy, amino, $(C_{1-5})$alkylamino, di$(C_{1-5})$alkylamino, uriedo, $(C_{1-5})$ alkyluriedo, mercapto, $(C_{1-5})$alkylthio, carboxy, carbamoyl, $(C_{1-5})$alkylcarbamoyl, di$(C_{1-5})$alkylcarbamoyl, $(C_{1-5})$alkylsulfinyl, $(C_{1-5})$alkylsulfonyl, guanidino, $-P(O)(OR_{12})_2$, $-OP(O)(OR_{12})_2$ or $-OP(O)(R_{12})_2$, $(C_{3-7})$cycloalkyl, $(C_{3-7})$cycloalkyl$(C_{1-5})$alkyl, $(C_{5-14})$aryl, $(C_{5-14})$aryl$(C_{1-5})$alkyl (which group is optionally substituted at its aryl ring with one to three radicals selected from hydroxy, amino, guanidino, a halogen, optionally halogen substituted $(C_{1-5})$alkyl, $(C_{1-5})$alkyloxy and $(C_{5-14})$aryl, or a protected derivative thereof) or together with an adjacent $R_{14}$ forms a divalent radical selected from $(C_{3-4})$methylene and 1,2-phenylenedimethylene (which radical is optionally substituted with hydroxy, or a protected derivative thereof, or oxo), with the proviso X and A are not both hydrogen;

each $R_{12}$ is independently hydrogen or $(C_{1-5})$alkyl or a protected derivative thereof;

$R_1$ and $R_2$ are both hydrogen or one of $R_1$ or $R_2$ is cyano, carboxy, $(C_{1-5})$alkyloxycarbonyl, $(C_{1-5})$alkanoyl, carbamoyl, $(C_{1-5})$alkylcarbamoyl, di$(C_{1-5})$alkylcarbamoyl, $(C_{1-5})$alkyloxy($(C_{1-5})$alkyl)carbamoyl, amino$(C_{1-5})$alkylcarbamoyl, $R_{16}$, as defined above, or $R_{13}-X_2-$, wherein $R_{13}$ is as defined above and $X_2$ is a divalent radical of Formulae (a) or (b), as defined above;

$R_3$ and $R_4$ are hydrogen or together form optionally substituted ethylene, wherein said ethylene substituent is an amino acid side chain or are independently $R_{14}$, as defined above; and the pharmaceutically acceptable salts, individual isomers and mixtures of isomers thereof.

20. The compound of claim 19, wherein

A is $R_{13}-X_1-$;

$R_{13}$ is hydrogen, alkyloxycarbonylalkanoyl of overall 3 to 10 carbon atoms, $(C_{1-9})$alkoxycarbonyl, $(C_{2-10})$alkanoyl (optionally substituted with a radical selected from carboxy, $(C_{1-9})$alkyloxycarbonyl and hetero$(C_{4-8})$cycloalkyl$(C_{2-10})$alkanoylamino), $(C_{4-8})$cycloalkylcarbonyl, hetero$(C_{4-8})$cycloalkylcarbonyl (optionally substituted with a radical selected from hydroxy, $(C_{1-5})$alkyl, hetero$(C_{4-8})$cycloalkyl, $(C_{1-5})$alkanoyl, $(C_{1-5})$alkyloxycarbonyl, $(C_{6-10})$aryl$(C_{1-5})$alkyloxycarbonyl and hetero$(C_{4-8})$cycloalkylcarbonyl), $(C_{6-10})$aryl$(C_{1-5})$alkyloxycarbonyl, carbamoyl, $(C_{1-5})$alkylcarbamoyl, di$(C_{1-5})$alkylcarbamoyl, $(C_{6-10})$arylcarbamoyl, $(C_{6-10})$aryl$(C_{1-5})$alkylcarbamoyl, $(C_{6-10})$aryl$(C_{1-5})$alkanoyl, $(C_{7-11})$aroyl, $(C_{1-10})$alkylsulfonyl, di$(C_{1-5})$alkylsulfamoyl, $(C_{6-10})$arylsulfonyl, $(C_{6-10})$aryl$(C_{1-5})$alkylsulfonyl or hetero$(C_{4-8})$arylsulfonyl;

$X_1$ is a divalent radical of Formula (a);

n is 0 to 5;

$X_3-X_4$ represents $-C(O)NR_{14}-$;

Y is $-N(R_{14})-$;

Z is $-CH(R_{16})-$;

$R_{14}$ is hydrogen or as defined below;

each $R_{16}$ is independently hydrogen, $(C_{3-7})$cycloalkyl, $(C_{3-7})$cycloalkyl$(C_{1-5})$alkyl, pyridyl, thienyl, furyl, imidazolyl, indolyl, pyridyl$(C_{1-6})$alkyl, thienyl$(C_{1-6})$alkyl, furyl$(C_{1-6})$alkyl, imidazolyl$(C_{1-6})$alkyl, indolyl $(C_{1-6})$alkyl, $(C_{1-5})$alkyl (optionally substituted with a radical selected from mercapto, carboxy, amino, methylthio, methylsulfonyl, carbamoyl, dimethylcarbamoyl, guanidino and hydroxy, or a protected derivative thereof), phenyl, naphthyl, phenyl$(C_{1-6})$alkyl, naphthyl$(C_{1-6})$alkyl, (which group is optionally substituted at its aryl ring with one to three radicals selected from amino, hydroxy, chloro, bromo, fluoro, iodo, methyl, trifluoromethyl, methoxy and phenyl, or a protected derivative thereof) or together with an adjacent $R_{14}$ forms a divalent radical selected from $(C_{3-4})$methylene and 1,2-phenylenedimethylene (which radical is optionally substituted with hydroxy, or a protected derivative thereof, or oxo);

X is —S(O)$_2$R$_9$;

$R_9$ is $(C_{1-5})$alkyl (optionally substituted with one or two radicals selected from amino, chloro, bromo, fluoro, hydroxy and methoxy, or a protected derivative thereof), perhalo$(C_{1-5})$alkylsulfonyl, $(C_{3-7})$cycloalkyl, $(C_{3-7})$cycloalkyl$(C_{1-5})$alkyl or a group selected from phenyl, pentafluorophenyl, naphthyl and phenyl$(C_{1-6})$ alkyl (which group is optionally substituted at its aryl ring with one to two radicals selected from amino, chloro, bromo, fluoro, hydroxy, methoxy and optionally halo-substituted methyl, or a protected derivative thereof);

$R_1$ is hydrogen;

$R_2$ is $R_{16}$; and $R_3$ and $R_4$ are each hydrogen or together form optionaly substituted ethylene.

21. The compound of claim 20 wherein n is 0 to 2;

$R_2$ is $R_{16}$, as defined below;

$R_3$ and $R_4$ together form optionally substituted ethylene;

$R_{13}$ is hydrogen, $(C_{4-8})$alkoxycarbonyl, $(C_{2-6})$alkanoyl (optionally substituted with a radical selected from carboxy, $(C_{1-5})$alkyloxycarbonyl and hetero$(C_{4-8})$ cycloalkyl$(C_{4-6})$alkanoylamino), —C(O)NR$_{10}$R$_{11}$;

$R_{10}$ and $R_{11}$ together form aza$(C_{2-6})$methylene, oxa$(C_{2-6})$methylene or $(C_{3-7})$methylene, $(C_{4-8})$ cycloalkylcarbonyl, benzyloxycarbonyl, acetyl, benzoyl or dimethylsulfamoyl;

$R_{16}$ is $(C_{5-6})$cycloalkyl, $(C_{5-6})$cycloalkylmethyl, 3-pyridyl, 2-thienyl, 2-furyl, 4-imidazolyl, 3-indolyl, 3-pyridylmethyl, 2-thienylmethyl, 2-furylmethyl, 4-imidazolylmethyl, 3-indolylmethyl, methoxy, acetoxy, $(C_{1-5})$alkyl (optionally substituted with a radical selected from mercapto, carboxy, amino, methylthio, methylsulfonyl, carbamoyl, dimethylcarbamoyl, guanidino and hydroxy, or a protected derivative thereof), phenyl, 1-naphthyl, 2-naphthyl, benzyl, 1-naphthylmethyl, 2-naphthylmethyl, 2-phenylethyl (which group is optionally substituted at its aryl ring with one radical selected from hydroxy, amino, chloro, bromo and fluoro, or a protected form thereof) or together with an adjacent $R_{14}$ forms a divalent radical selected from $(C_{3-4})$methylene and 1,2-phenylenedimethylene (which radical is optionally substituted with hydroxy, or a protected derivative thereof, or oxo); and $R_9$ is $(C_{1-5})$alkyl (optionally substituted with one or two radicals selected from amino, chloro, bromo, fluoro and hydroxy, or a protected derivative thereof), perfluoro $(C_{1-5})$alkyl, $(C_{5-6})$cycloalkyl, $(C_{5-6})$cycloalkylmethyl or a group selected from phenyl, naphthyl and benzyl (which group is optionally substituted with one radical selected from amino hydroxy, chloro, bromo and fluoro, or a protected derivative thereof).

* * * * *